United States Patent
Mikoshiba et al.

(10) Patent No.: US 6,180,818 B1
(45) Date of Patent: Jan. 30, 2001

(54) SILVER HALIDE PHOTOGRAPHIC MATERIAL AND HYDROXAMIC ACID-BASE COMPOUND FOR USE THEREIN

(75) Inventors: Hisashi Mikoshiba; Hiroo Takizawa; Junichiro Hosokawa; Yoshio Ishii; Keiji Mihayashi; Masakazu Morigaki; Mamoru Sakurazawa, all of Kanagawa (JP)

(73) Assignee: Fuji Photo Film Co., Ltd., Kanagawa (JP)

( * ) Notice: Under 35 U.S.C. 154(b), the term of this patent shall be extended for 0 days.

(21) Appl. No.: 09/432,770

(22) Filed: Nov. 3, 1999

Related U.S. Application Data

(62) Division of application No. 09/146,041, filed on Sep. 2, 1998, now Pat. No. 6,114,570, which is a division of application No. 08/659,722, filed on Jun. 6, 1996, now Pat. No. 5,851,754.

(30) Foreign Application Priority Data

| Jun. 7, 1995 | (JP) | 7-163085 |
| Jun. 12, 1995 | (JP) | 7-167836 |
| Sep. 5, 1995 | (JP) | 7-250141 |

(51) Int. Cl.$^7$ ................................................ C07C 69/74
(52) U.S. Cl. ............... 560/128; 560/120; 560/170; 560/312; 560/315; 562/621; 562/622; 544/162; 546/205; 548/469; 548/503; 548/510; 548/530; 548/539; 548/571; 558/428
(58) Field of Search .................... 560/120, 312, 560/315, 125, 128, 170; 562/621, 622

(56) References Cited

U.S. PATENT DOCUMENTS

| 4,330,606 | 5/1982 | Sobel et al. . |
| 4,339,515 | 7/1982 | Schranz et al. . |
| 4,680,257 | 7/1987 | Sato et al. . |
| 5,206,131 | 4/1993 | Matsuda et al. . |

FOREIGN PATENT DOCUMENTS

| 3520896 | 6/1985 | (DE) . |
| 2 0698814 | 2/1996 | (EP) . |
| 59-198453 | 11/1984 | (JP) . |
| 5-194589 | 8/1993 | (JP) . |

OTHER PUBLICATIONS

Midyanko et al, Transition Met. Chem. 15(2), abstract only, 1990.
Nakamura et al, Anal. Chem., 61(18), 2121–4, 1989.
Horvat et al, Int. J. Pept, Protein Res., 31(5), abstract only, 1988.
RN 174414–50–7, 1995.*

* cited by examiner

Primary Examiner—Shailendra Kumar
(74) Attorney, Agent, or Firm—Sughrue, Mion, Zinn, Macpeak & Seas, PLLC

(57) ABSTRACT

A silver halide photographic material is disclosed, comprising a support having thereon at least one light-sensitive silver halide emulsion layer, wherein said silver halide photographic material contains a compound by formula (IA), or which contains at least one hydroxamic acid compound having a bicyclo ring as a partial structure and represented by formula (IB).

3 Claims, No Drawings

SILVER HALIDE PHOTOGRAPHIC MATERIAL AND HYDROXAMIC ACID-BASE COMPOUND FOR USE THEREIN

This is a divisional of application Ser. No. 09/146,041 filed Sep. 2, 1998, now U.S. Pat. No. 6,114,780, which is a divisional of application Ser. No. 08/659,722 filed Jun. 6, 1996 and issued as U.S. Pat. No. 5,851,754, the disclosure of which is incorporated herein by reference.

FIELD OF THE INVENTION

The present invention relates to a light-sensitive silver halide photographic material, more specifically, the present invention relates to a photographic material less changeable in the photographic capability after storage and less changeable in the photographic capability after photographing until development processing.

Further, the present invention relates to a silver halide photographic material causing less generation of fog.

Furthermore, the present invention relates to a novel hydroxamic acid-base compound capable of providing photographically useful effects.

BACKGROUND OF THE INVENTION

Silver halide photographic materials are not only demanded to have high sensitivity but also be less changeable in the photographic capability during storage after the preparation of the photographic material and also less changeable in the photographic capability after photographing until development processing.

Out of changes in the photographic capability after photographing until development processing, with respect to the prevention of latensification, JP-A-59-162546 (the term "JP-A" as used herein means an "unexamined published Japanese patent application") discloses a method of using a hardening agent having an active vinyl group in combination with a triazine-base compound.

However, the above-described method is insufficient in the prevention effect and a further improvement has been demanded.

On the other hand, full color photographic materials use a plurality of emulsions different in the spectral sensitivity as a superposed layer structure, thereby achieving the object of full color photograph. The emulsions used therein have been fairly improved, however, they are still unsatisfactory because fogging of the latent image or intensification/regression is caused. In order to improve storability of the emulsion, for example, 2-hydroxamino-1,3,5-triazines are effective. However, the layers are different in the storability from each other depending upon the emulsion used therein. Accordingly, in recent years, it is being rather strongly demanded to improve storability of a latent image of a specific emulsion layer.

Many of known 2-hydroxylamine-1,3,5-triazines diffuse and act on the emulsion in the layer other than the objective layer and as a result, the balance in the gradation among respective layers is lost. Further, hydroxamic acids having a specific structure described in U.S. Pat. Nos. 4,339,515 and 4,330,606, JP-A-59-198453 and JP-A-3-293666 are used to improve storability of a color image or as a nucleophilic agent and different from the present invention in the use object. Moreover, the above-described hydroxamic acids are insufficient in causing action only on an emulsion in a specific layer. Accordingly, a method for greatly improving the storability of a latent image only in the objective layer has been keenly demanded.

The present invention provides a method for improving storability of an emulsion in a specific layer and stability of a latent image.

In order to overcome the above-described problems, the present inventors have made extensive investigations on the method for improving storability of an emulsion produced and storability of a latent image, in particular, on the structure of compounds, and as a result, they have found a novel hydroxamic acid-base compound having a specific structure for use in the present invention.

The compound for use in the present invention is found, when added to a silver halide photographic material, able to achieve the objects of the present invention without changing the hue of the dye formed, affecting the dye formation speed of couplers, accelerating the decomposition of the coupler or the dye formed, deteriorating the layer strength or fogging the emulsion.

Out of the compounds for use in the present invention, the compounds represented by formulae (IVA), (IVB), (VA) and (VB) are completely novel compounds which have not known in the past. These compounds are first found to be photographically useful after investigations by the present inventors.

SUMMARY OF THE INVENTION

A first object of the present invention is to provide a compound highly effective in improving the storability of a silver halide emulsion and storability of a latent image.

A second object of the present invention is to provide a method for improving storability of a latent image using the above-described compound.

A third object of the present invention is to provide a compound capable of improving storability only of a latent image in a specific layer.

A fourth object of the present invention is to provide a method for improving storability of a latent image using the above-described compound.

A fifth object of the present invention is to provide a compound capable of, when added, improving storability of a latent image without adversely affecting various photographic properties.

A sixth object of the present invention is to provide a method for improving storability of a latent image using the above-described compound.

The objects of the present invention have been achieved by the following materials and compounds:

(1) a silver halide photographic material comprising a support having thereon at least one light-sensitive silver halide emulsion layer, wherein said silver halide photographic material contains a compound represented by formula (IA):

$$R^{2a}-\overset{\overset{\displaystyle O}{\|}}{C}-\underset{\underset{\displaystyle R^{1a}}{|}}{N}-OH \quad \text{(IA)}$$

wherein $R^{1a}$ represents a hydrogen atom, a substituted or unsubstituted alkyl group having from 1 to 20 carbon atoms, a substituted or unsubstituted alkenyl group having from 2 to 20 carbon atoms or a substituted or unsubstituted aryl group having from 6 to 20 carbon atoms;

$R^{2a}$ represents an alkenyl group having a total carbon number of 4 or more or a cycloalkenyl group having a total carbon atom number of 6 or more;

provided that when $R^{2a}$ is a styryl group, $R^{1a}$ is a substituted or unsubstituted alkyl group having from 1 to 20 carbon atoms, a substituted or unsubstituted alkenyl group having from 2 to 20 carbon atoms or a substituted or unsubstituted aryl group having from 6 to 20 carbon atoms; and when $R^{2a}$ is an alkenyl group having a total carbon number of 17 or more, $R^{1a}$ is a hydrogen atom, a substituted or unsubstituted alkyl group having 7 or more carbon atoms, a substituted or unsubstituted alkenyl group having 7 or more carbon atoms or a substituted or unsubstituted aryl group having from 6 to 20 carbon atoms;

(2) a silver halide photographic material as described in item (1), wherein the compound represented by formula (IA) has a structure represented by formula (IIA) or (IIIA):

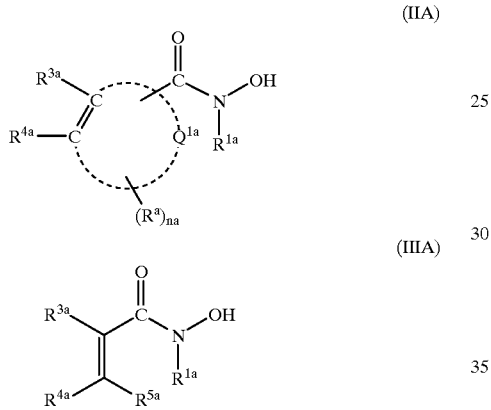

wherein in formula (IIA), $R^{1a}$ represents a hydrogen atom, a substituted or unsubstituted alkyl group having from 1 to 20 carbon atoms or a substituted or unsubstituted alkenyl group having from 2 to 20 carbon atoms;

$Q^{1a}$ represents an atomic group necessary for forming a cycloalkenyl group by combining with the carbon atoms at both terminals;

$R^{3a}$ and $R^{4a}$, which may be the same or different, each represents an alkyl group having from 1 to 22 carbon atoms, an aryl group having from 6 to 20 carbon atoms, an alkenyl group having from 3 to 22 carbon atoms, a carboxyl group, a cyano group, an acyl group having from 2 to 20 carbon atoms, an aminocarbonyl group having from 1 to 37 carbon atoms, an alkoxycarbonyl group having from 2 to 20 carbon atoms, an aryloxycarbonyl group having from 7 to 20 carbon atoms or a heterocyclic group having from 3 to 20 carbon atoms;

$R^a$ represents an alkyl group, an aryl group, an alkoxy group, an aryloxy group, an alkenyl group, a carboxyl group, a cyano group, a sulfamoyl group, an acyl group, a carbamoyl group, an alkoxycarbonyl group, an aryloxycarbonyl group, an acylamino group, an alkoxycarbonylamino group, an aryloxycarbonylamino group, an alkylsulfonylamino group, an arylsulfonylamino group, an aminocarbonylamino group, a sulfamoylamino group, an amino group, a heterocyclic oxy group, an alkylthio group, an arylthio group, a heterocyclic thio group, a heterocyclic group, an alkylsulfonyl group or an arylsulfonyl group; and na represents 0 or a positive integer, and when na is 0, $R^a$ is a hydrogen atom and when na is 2 or greater, the $R^a$ groups in plurality may be the same or different; and in formula (IIIA), $R^{1a}$ represents a hydrogen atom, a substituted or unsubstituted alkyl group having from 1 to 20 carbon atoms or a substituted or unsubstituted alkenyl group having from 2 to 20 carbon atoms, $R^{3a}$, $R^{4a}$ and $R^{5a}$, which may be the same or different, each has the same meaning as $R^{3a}$ or $R^{4a}$ of formula (IIA);

when $R^{4a}$ is a phenyl group, $R^{1a}$ is a substituted or unsubstituted alkyl group having from 1 to 22 carbon atoms, a substituted or unsubstituted alkenyl group having from 2 to 22 carbon atoms or a substituted or unsubstituted aryl group having from 6 to 20 carbon atoms; and $R^{3a}$ and $R^{4a}$ and/or $R^{4a}$ and $R^{5a}$ and/or $R^{5a}$ and $R^{1a}$ may be combined with each other to form a 5- or 6-membered ring structure;

(3) a compound represented by formula (IVA) or (VA):

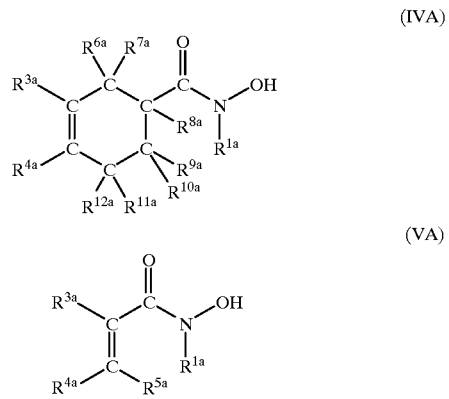

wherein in formula (IVA), $R^{1a}$, $R^{3a}$ and $R^{4a}$ have the same meaning as $R^{1a}$, $R^{3a}$ and $R^{4a}$ of formula (IIA) in item (2), respectively;

$R^{6a}$, $R^{7a}$, $R^{8a}$, $R^{9a}$, $R^{10a}$, $R^{11a}$ and $R^{12a}$, which may be the same or different, each represents a hydrogen atom, an alkyl group having from 1 to 20 carbon atoms, an alkoxycarbonyl group having from 2 to 30 carbon atoms, an aminocarbonyl group having from 1 to 30 carbon atoms or an aryloxycarbonyl group having from 7 to 30 carbon atoms; and in formula (VA), $R^{1a}$ has the same meaning as $R^{1a}$ of formula (IIIA) in item (2);

$R^{3a}$, $R^{4a}$ and $R^{5a}$, which may be the same or different, each represents a hydrogen atom, an alkyl group having from 1 to 20 carbon atoms, an aryl group having from 6 to 22 carbon atoms, an alkoxycarbonyl group having from 2 to 30 carbon atoms, an aryloxycarbonyl group having from 7 to 30 carbon atoms or an aminocarbonyl group having from 1 to 30 carbon atoms; and when $R^{4a}$ is a phenyl group, $R^{1a}$ is a substituted or unsubstituted alkyl group having from 1 to 20 carbon atoms or a substituted or unsubstituted alkenyl group having from 2 to 20 carbon atoms;

(4) a silver halide photographic material comprising a support having thereon at least one silver halide emulsion layer, which contains at least one hydroxamic acid compound having a bicyclo ring as a partial structure;

(5) a silver halide photographic material as described in item (4), wherein said hydroxamic acid compound is represented by the following formula (IB):

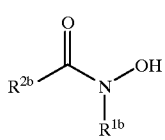
(IB)

wherein $R^{1b}$ represents a hydrogen atom, a substituted or unsubstituted alkyl group having from 1 to 30 carbon atoms, a substituted or unsubstituted cycloalkyl group having from 5 to 30 carbon atoms, a substituted or unsubstituted alkenyl group having from 3 to 30 carbon atoms or a substituted or unsubstituted cycloalkenyl group having from 5 to 30 carbon atoms, and $R^{2b}$ represents a substituted or unsubstituted bicycloalkyl group having from 5 to 40 carbon atoms or a substituted or unsubstituted bicycloalkenyl group having from 5 to 40 carbon atoms;

(6) a silver halide photographic material as described in item (5), wherein the compound represented by formula (IB) has a structure represented by formula (IIB) or (IIIB):

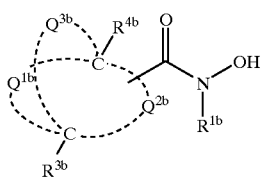
(IIB)

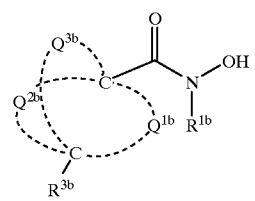
(IIIB)

wherein $R^{1b}$ represents a hydrogen atom, a substituted or unsubstituted alkyl group having from 1 to 30 carbon atoms, a substituted or unsubstituted cycloalkyl group having from 5 to 30 carbon atoms, a substituted or unsubstituted alkenyl group having from 3 to 30 carbon atoms or a substituted or unsubstituted cycloalkenyl group having from 5 to 30 carbon atoms;

$R^{3b}$ and $R^{4b}$, which may be the same or different, each represents a hydrogen atom or a substituted or unsubstituted alkyl group having from 1 to 30 carbon atoms; and $Q^{1b}$, $Q^{2b}$ and $Q^{3b}$ each independently represents an atomic group necessary for forming a bicyclo ring by combining with the carbon atoms at both terminals; and (7) a hydroxamic acid compound represented by formula (IVB) or (VB):

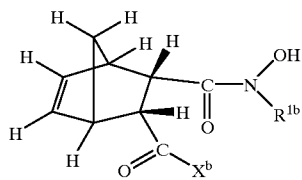
(IVB)

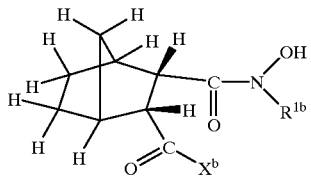
(VB)

wherein $X^b$ represents $-OR^{5b}$ or $-N(R^{5b})(R^{6b})$ (wherein $R^{5b}$ and $R^{6b}$, which may be the same or different, each represents a hydrogen atom, a substituted or unsubstituted alkyl group having from 1 to 30 carbon atoms, a substituted or unsubstituted cycloalkyl group having from 5 to 30 carbon atoms or a substituted or unsubstituted aryl group having from 6 to 30 carbon atoms, and $R^{5b}$ and $R^{6b}$ are combined with each other to form a ring structure); and $R^{1b}$ represents a hydrogen atom or an alkyl group having from 1 to 6 carbon atoms.

DETAILED DESCRIPTION OF THE INVENTION

Formula (IA) is described in detail below.

In formula (IA), $R^{1a}$ represents a hydrogen atom, a substituted or unsubstituted alkyl group having from 1 to 20 carbon atoms, a substituted or unsubstituted alkenyl group having from 2 to 20 carbon atoms or a substituted or unsubstituted aryl group having from 6 to 20 carbon atoms.

Specific examples of $R^{1a}$ include a hydrogen atom and as an alkyl group, methyl, ethyl, n-propyl, isopropyl, n-butyl, sec-butyl, t-butyl, n-pentyl, isopentyl, neopentyl, n-hexyl and n-dodecyl.

Examples of the substituent of the alkyl group include an alkyl group, an alkenyl group, an aryl group, a heterocyclic group, a halogen atom, an alkoxy group, an aryloxy group, an alkylthio group, an arylthio group, a cyano group, a nitro group, an alkoxycarbonyl group, an aryloxycarbonyl group, a hydroxyl group, an acyl group, an acyloxy group, an alkylsulfonyl group, an arylsulfonyl group, an acylamino group, an alkylsulfonamido group and an arylsulfonamido group. Specific examples thereof include 2-chloroethyl, 2-methoxyethyl, 2-cyanoethyl, 2-ethoxycarbonylethyl, 3-methylthiopropyl, 2-acetylaminoethyl, 3-hydroxypropyl, 2-acetyloxyethyl, 3-chloroethyl and 3-methoxyethyl. Specific examples of the alkenyl group include allyl, prenyl, homoprenyl, geranyl and oleyl.

Specific examples of the aryl group represented by $R^{1a}$ include phenyl, o-chlorophenyl, m-methoxyphenyl, naphthyl, p-diethylaminophenyl and p-(n)-dodecylphenyl.

$R^{2a}$ represents an alkenyl group having a total carbon number of 4 or more or a cycloalkenyl group having a total carbon number of 6 or more.

Specific examples of the alkenyl group include a geranyl group, a geranylgeranyl group, an oleyl group, a substituted vinyl group (having from 4 to 30 carbon atoms, e.g., cisoctylvinyl, transoctylvinyl, transdodecylvinyl) and prenyl.

In the nomenclature, the cycloalkenyl group is a monocyclic group containing one double bond, however, in the present invention, the cycloalkenyl group includes a cycloalkadienyl group having a relation to the cycloalkenyl group.

Specific examples of the cycloalkenyl group include 2-cyclohexenyl, 3-cyclohexenyl, 2,4-cyclohexadienyl and 2-cyclopentyl.

The compound for use in the present invention preferably has a structure represented by formula (IIA) or (IIIA).

In formula (IIA), $R^{1a}$ represents a hydrogen atom, a substituted or unsubstituted alkyl group having from 1 to 20 carbon atoms or a substituted or unsubstituted alkenyl group having from 3 to 20 carbon atoms.

Specific examples thereof include those described in formula (IA).

$R^{3a}$ and $R^{4a}$, which may be the same or different, each independently represents a hydrogen atom, a substituted or unsubstituted alkyl group having from 1 to 22 carbon atoms, an aryl group having from 6 to 20 carbon atoms, an alkenyl group having from 3 to 22 carbon atoms, a carboxyl group, a cyano group, an acyl group having from 2 to 20 carbon atoms, an aminocarbonyl group having from 1 to 37 carbon atoms, an alkoxycarbonyl group having from 2 to 20 carbon atoms, an aryloxycarbonyl group having from 7 to 20 carbon atoms or a heterocyclic group having from 3 to 20 carbon atoms.

Specific examples thereof include those described below for $R^a$.

$R^a$ represents an alkyl group, an aryl group, an alkoxy group, an aryloxy group, an alkenyl group, a carboxyl group, a cyano group, a sulfamoyl group, an acyl group, a carbamoyl group, an alkoxycarbonyl group, an aryloxycarbonyl group, an acylamino group, an alkoxycarbonyl group, an aryloxycarbonylamino group, an alkylsulfonylamino group, an arylsulfonylamino group, an aminocarbonylamino group, a sulfamoylamino group, an amino group, a heterocyclic oxy group, an alkylthio group, an arylthio group, a heterocyclic thio group, a heterocyclic group, an alkylsulfonyl group or an arylsulfonyl group.

Examples thereof include an aryl group (inclusive of a substituted aryl group, preferably having from 6 to 20 carbon atoms, e.g., phenyl, m-acetylaminophenyl, p-methoxyphenyl), an alkyl group (inclusive of a substituted alkyl group, preferably having from 1 to 30 carbon atoms, e.g., methyl, ethyl, isopropyl, t-butyl, n-octyl, n-dodecyl), a cyano group, a carboxyl group, an acyl group (preferably having from 1 to 30 carbon atoms, e.g., acetyl, pivaloyl, benzoyl, furoyl, 2-pyridyl), a carbamoyl group (preferably having from 1 to 30 carbon atoms, e.g., methylcarbamoyl, ethylcarbamoyl, dimethylcarbamoyl, n-octylcarbamoyl), an alkoxycarbonyl group (inclusive of a substituted alkoxycarbonyl group, preferably having from 2 to 30 carbon atoms, e.g., methoxycarbonyl, ethoxycarbonyl, isopropoxycarbonyl), an aryloxycarbonyl group (including a substituted aryloxycarbonyl group, preferably having from 7 to 30 carbon atoms, e.g., phenoxycarbonyl, p-methoxyphenoxycarbonyl, m-chlorophenoxycarbonyl, o-methoxyphenoxycarbonyl), an acylamino group [for example, an alkylcarbonylamino group preferably having from 1 to 30 carbon atoms (inclusive of a substituted alkylcarbonylamino group, e.g., formylamino, acetylamino, propionylamino, cyanoacetylamino), an arylcarbonylamino group preferably having from 7 to 30 carbon atoms (inclusive of a substituted arylcarbonylamino group, e.g., benzoylamino, p-toluylamino, pentafluorobenzoylamino, m-methoxybenzoylamino), and a heterylcarbonylamino group preferably having from 4 to 30 carbon atoms (inclusive of a substituted heterylcarbonylamino group, e.g., 2-pyridylcarbonylamino, 3-pyridylcarbonylamino, furoylamino)], an alkoxycarbonylamino group (inclusive of a substituted alkoxycarbonylamino group, preferably having from 2 to 30 carbon atoms, e.g., methoxycarbonylamino, ethoxycarbonylamino, methoxyethoxycarbonylamino), an aryloxycarbonylamino group (inclusive of a substituted aryloxycarbonylamino group, preferably having from 7 to 30 carbon atoms, e.g., phenoxycarbonylamino, p-methoxyphenoxycarbonylamino, p-methylphenoxycarbonylamino, m-chlorophenoxycarbonylamino, o-chlorophenoxycarbonylamino), an aminocarbonylamino group (preferably having from 1 to 30 carbon atoms, e.g., methylaminocarbonylamino, ethylaminocarbonylamino, anilinocarbonylamino, dimethylaminocarbonylamino), a sulfamoylamino group (preferably having from 1 to 30 carbon atoms, e.g., methylaminosulfonylamino, ethylaminosulfonylamino, anilinosulfonylamino), an amino group (inclusive of an anilino group, preferably having from 0 to 30 carbon atoms, e.g., amino, methylamino, dimethylamino, ethylamino, diethylamino, n-butylamino, anilino), an alkoxy group (inclusive of a substituted alkoxy group, preferably having from 1 to 30 carbon atoms, e.g., methoxy, ethoxy, isopropoxy, n-butoxy, methoxyethoxy, isopropoxy, n-dodecyloxy), an aryloxy group (inclusive of a substituted aryloxy group, preferably having from 6 to 30 carbon atoms, e.g., phenoxy, m-chlorophenoxy, p-methoxyphenoxy, o-methoxyphenoxy), a heteryloxy group (inclusive of a substituted heteryloxy group, preferably having from 3 to 30 carbon atoms, e.g., tetrahydropyranyloxy, 3-pyridyloxy, 2-(1,3-benzimidazolyl)oxy), an alkylthio group (inclusive of a substituted alkylthio group, preferably having from 1 to 30 carbon atoms, e.g., methylthio, ethylthio, n-butylthio, t-butylthio), an arylthio group (inclusive of a substituted arylthio group, preferably having from 6 to 30 carbon atoms, e.g., phenylthio), a heterylthio group (inclusive of a substituted heterylthio group, preferably having from 3 to 30 carbon atoms, e.g., 2-pyridylthio, 2-(1,3-benzoxazolyl)thio, 1-hexadecyl-1,2,3,4-tetrazolyl-5-thio, -1-(3-N-octadecylcarbmoyl)phenyl-1,2,3,4-tetrazolyl-5-thio), a heterocyclic group (inclusive of a substituted heterocyclic group, preferably having from 3 to 30 carbon atoms, e.g., thiadiazolyl, pyrazolyl), an alkenyl group (preferably having from 3 to 18 carbon atoms, e.g., vinyl, allyl, prenyl), a sulfamoyl group (preferably having from 0 to 36 carbon atoms, e.g., methylsulfamoyl, dimethylsulfamoyl, dioctylsulfamoyl), an alkylsulfonylamino group (preferably having from 1 to 18 carbon atoms, e.g., methanesulfonylamino, n-butanesulfonylamino), an arylsulfonylamino group (preferably having from 6 to 18 carbon atoms, e.g., benzenesulfonylamino, p-toluenesulfonylamino), an alkylsulfonyl group (preferably having from 1 to 18 carbon atoms, e.g., methanesulfonyl, ethanesulfonyl, n-octanesulfonyl) and an arylsulfonyl group (preferably having from 6 to 18 carbon atoms, e.g., benzenesulfonyl, p-toluenesulfonyl).

na represents 0 or a positive integer, and when na is 0, $R^a$ is a hydrogen atom and when na is 2 or greater, the $R^a$ groups in plurality may be the same or different.

na is preferably 1 or greater, most preferably 1.

$Q^{1a}$ represents an atomic group necessary for forming a cycloalkenyl group by combining with the carbon atoms at both terminals.

Specific examples thereof are described below.

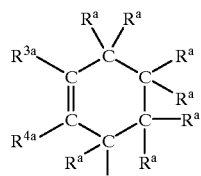
(IIA)-1

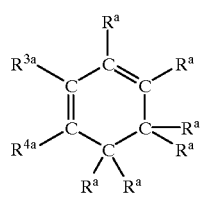
(IIA)-2

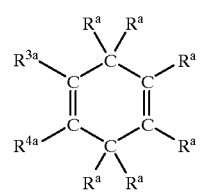
(IIA)-3

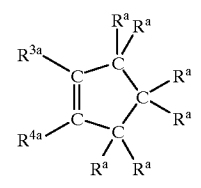
(IIA)-4

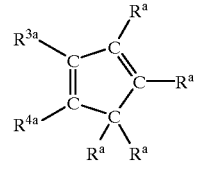
(IIA)-5

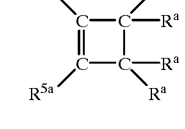
(IIA)-6

The cycloalkenyl group is a monovalent group obtained by removing one $R^a$ group from the structure represented by formula (IIA)-1, (IIA)-2, (IIA)-3, (IIA)-4, (IIA)-5 or (IIA)-6.

The $R^a$ groups may be the same or different and each independently has the same meaning as $R^a$ in formula (IIA).

$R^{3a}$ and $R^{4a}$ have the same meaning as $R^{3a}$ and $R^{4a}$ in formula (IIA), respectively.

Among formulae (IIA)-1 to (IIA)-6, preferred are formulae (IIA)-1 and (IIA)-4.

In a preferred embodiment of formula (IIA), $R^{1a}$ is a hydrogen atom or a substituted or unsubstituted alkyl group having from 1 to 20 carbon atoms, $Q^{1a}$ forms a structure of formula (IIA)-1 or (IIA)-4, $R^{3a}$ and $R^{4a}$, which may be the same or different, each independently is a hydrogen atom, an alkyl group having from 1 to 6 carbon atoms, an alkoxycarbonyl group having from 2 to 23 carbon atoms or an aminocarbonyl group having from 3 to 37 carbon atoms, $R^a$ is an alkyl group having from 1 to 22 carbon atoms, an alkoxycarbonyl group having from 2 to 23 carbon atoms, an aminocarbonyl group having from 3 to 27 carbon atoms or an aryloxycarbonyl group having from 7 to 26 carbon atoms, and na is 0 or 1.

In a more preferred embodiment of formula (IIA), $R^{1a}$ is a substituted or unsubstituted alkyl group having from 1 to 20 carbon atoms, $Q^{1a}$ forms a structure of formula (IIA)-1, $R^{3a}$ and $R^{4a}$, which may be the same or different, each independently is a hydrogen atom or a substituted or unsubstituted alkyl group having from 1 to 6 carbon atoms, $R^a$ is an alkoxycarbonyl group having from 2 to 23 carbon atoms or an aminocarbonyl group having from 3 to 27 carbon atoms, and na is 1.

A still more preferred embodiment of formula (IIA) is the structure represented by formula (IVA):

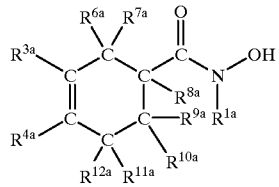
(IVA)

wherein $R^{1a}$ represents a hydrogen atom or a substituted or unsubstituted alkyl group having from 1 to 20 carbon atoms, $R^{3a}$ and $R^{4a}$ have the same meaning as $R^{3a}$ and $R^{4a}$ in formula (IIA), respectively, $R^{6a}$, $R^{7a}$, $R^{8a}$, $R^{9a}$, $R^{10a}$, $R^{11a}$ and $R^{12a}$, which may be the same or different, each independently represents a hydrogen atom or has the same meaning as $R^a$ in formula (IIA), and one of $R^{3a}$, $R^{4a}$, $R^{6a}$, $R^{7a}$, $R^{8a}$, $R^{9a}$ and $R^{10a}$ is an alkoxycarbonyl group having from 1 to 23 carbon atoms or an aminocarbonyl group having from 3 to 37 carbon atoms.

In a preferred embodiment of formula (IVA), $R^{1a}$ is a hydrogen atom or a substituted or unsubstituted alkyl group having from 1 to 20 carbon atoms, $R^{3a}$ and $R^{4a}$, which may be the same or different, each is a hydrogen atom or a substituted or unsubstituted alkyl group having from 1 to 30 carbon atoms, $R^{6a}$, $R^{7a}$, $R^{8a}$, $R^{9a}$, $R^{11a}$ and $R^{12a}$ all are a hydrogen atom, $R^{10a}$ is an alkoxycarbonyl group having from 2 to 23 carbon atoms or an aminocarbonyl group having from 3 to 37 carbon atoms.

In particular, $R^{10a}$ and the —$CON(R^{1a})$—OH group are in a cis relation with each other.

$R^{10a}$ is preferably an alkoxycarbonyl group rather than an aminocarbonyl group.

$R^{1a}$ is preferably an unsubstituted alkyl group having from 1 to 6 carbon atoms.

In a most preferred embodiment of formula (IVA), $R^{1a}$ is an unsubstituted alkyl group having from 1 to 6 carbon atoms, $R^{3a}$, $R^{4a}$, $R^{6a}$, $R^{7a}$, $R^{8a}$, $R^{9a}$, $R^{11a}$ and $R^{12a}$ all are a hydrogen atom, $R^{10a}$ is an unsubstituted alkoxycarbonyl group having from 12 to 23 carbon atoms, and $R^{10a}$ and the —$CON(R^{1a})$—OH group are in a cis relation with each other.

In formula (IIIA), $R^{3a}$, $R^{4a}$ and $R^{5a}$, which may be the same or different, each is the same as $R^{3a}$ or $R^{4a}$ in formula (IIA).

Specific examples thereof include those described above for $R^{3a}$ and $R^{4a}$ in formula (IIA). When $R^{4a}$ is a phenyl group, $R^{1a}$ is a substituted or unsubstituted alkyl group having from 1 to 22 carbon atoms, a substituted or unsubstituted alkenyl group having from 2 to 22 carbon atoms or a substituted or unsubstituted aryl group having from 6 to 20 carbon atoms.

A preferred embodiment of formula (IIIA) is the structure represented by formula (VA).

In formula (VA), $R^{1a}$ has the same meaning as $R^{1a}$ in formula (IIIA), $R^{3a}$, $R^{4a}$ and $R^{5a}$, which may be the same or different, each independently represents a hydrogen atom, an alkyl group having from 1 to 20 carbon atoms, an aryl group having from 6 to 22 carbon atoms, an alkoxycarbonyl group having from 2 to 30 carbon atoms, an aryloxycarbonyl group having from 7 to 30 carbon atoms or an aminocarbonyl group having from 1 to 30 carbon atoms.

When $R^{4a}$ is a phenyl group, $R^{1a}$ is a substituted or unsubstituted alkyl group having from 1 to 20 carbon atoms or a substituted or unsubstituted alkenyl group having from 2 to 22 carbon atoms.

In a preferred embodiment of formula (VA), $R^{1a}$ is a hydrogen atom or a substituted or unsubstituted alkyl group having from 1 to 20 carbon atoms, $R^{4a}$ and $R^{5a}$, which may be the same or different, each independently is a hydrogen atom, an alkoxycarbonyl group having from 2 to 23 carbon atoms or an aminocarbonyl group having from 3 to 37 carbon atoms, and $R^{3a}$ is a hydrogen atom.

In a most preferred embodiment of formula (VA), $R^{1a}$ is a substituted or unsubstituted alkyl group having from 1 to 6 carbon atoms, $R^{3a}$ is a hydrogen atom, and one of $R^{4a}$ and $R^{5a}$ is an alkoxycarbonyl group having from 14 to 23 carbon atoms and the other is a hydrogen atom.

The compound represented by formula (IA) has a molecular weight, when it is used to improve storability of a specific layer, of preferably 300 or more, more preferably 350 or more and most preferably 450 or more.

In this case, the compound for use in the present invention should be substantially insoluble in water so that it does not diffuse into the gelatin layer. The term "substantially insoluble in water" as used herein means that the solubility at 25° C. in water is 5% or less, preferably 1% or less.

Some raw materials (for example, acid anhydrides which will be described later or alcohols) for use in the synthesis of the compound for use in the present invention are available only as a mixture of isomers or homologs, and accordingly, in some cases, it is easy to synthesize the compound for use in the present invention as a mixture of isomers or homologs. In this case, the compound for use in the present invention is preferably added as the mixture to the silver halide photographic material.

Specific examples of the compound for use in the present invention are set forth below, however, the present invention is by no means limited thereto.

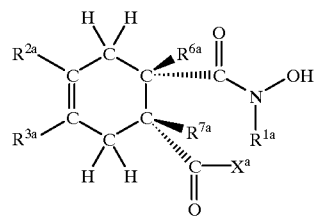

| Compound No. | $R^{1a}$ | $X^a$ | $R^{2a}$ | $R^{3a}$ | $R^{6a}$ | $R^{7a}$ |
|---|---|---|---|---|---|---|
| A-1 | $CH_3$ | —O—$C_{18}H_{37}{}^{-n}$ | H | H | H | H |
| A-2 | $C_2H_5$ | " | " | " | " | " |
| A-3 | $C_3H_7{}^{-n}$ | " | " | " | " | " |
| A-4 | —CH(CH$_3$)$_2$ | —O—$C_{16}H_{33}{}^{-n}$ | " | " | " | " |
| A-5 | $C_5H_{11}{}^{-n}$ | " | " | " | " | " |
| A-6 | —$CH_2CH_2CN$ | " | " | " | " | " |
| A-7 | $C_8H_{17}{}^{-n}$ | " | " | " | " | " |
| A-8 | $CH_3$ | —O—$C_{20}H_{41}{}^{-n}$ | H | H | H | H |
| A-9 | H | —O—$C_{22}H_{45}{}^{-n}$ | " | " | " | " |
| A-10 | $C_3H_7{}^{-n}$ | —O—$C_{14}H_{29}{}^{-n}$ | " | " | " | " |
| A-11 | $C_3H_7{}^{-n}$ | A | " | " | " | " |
| A-12 | $CH_3$ | B | " | " | " | " |
| A-13 | $C_5H_{11}{}^{-n}$ | —O—$C_{10}H_{21}{}^{-n}$ | " | " | " | " |
| A-14 | $CH_3$ | —O—$C_{18}H_{37}{}^{-n}$ | $CH_3$ | $CH_3$ | H | H |
| A-15 | $CH_3$ | —O—$C_{16}H_{33}{}^{-n}$ | $CH_3$ | $CH_3$ | $CH_3$ | $CH_3$ |
| A-16 | $CH_3$ | —N—($C_8H_{17}{}^{-n}$)$_2$ | H | H | H | H |
| A-17 | $C_2H_5$ | —N—(CH$_2$—CH(C$_2$H$_5$)—$C_4H_9{}^{-n}$)$_2$ | " | " | " | " |
| A-18 | $C_8H_{17}{}^{-n}$ | —N—($C_3H_7{}^{-n}$)$_2$ | " | " | " | " |

-continued
A-19 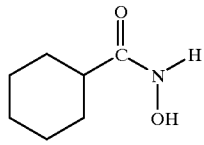
A-20 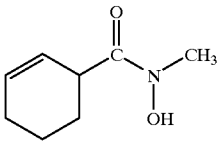
A-21 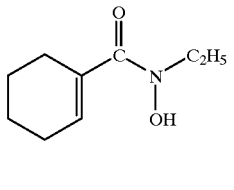
A-22 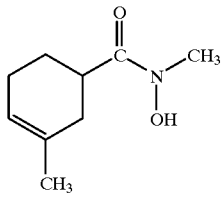
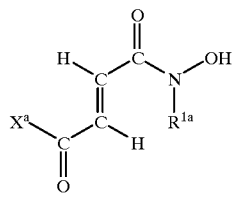
| Compound No. | $R^{1a}$ | $X^a$ |
|---|---|---|
| A-23 | $CH_3$ | $-O-C_{18}H_{37}{}^{-n}$ |
| A-24 | $C_2H_5$ | $-O-C_{16}H_{33}{}^{-n}$ |
| A-25 | $C_3H_7{}^{-n}$ | $-O-C_{14}H_{29}{}^{-n}$ |
| A-26 | $C_4H_9{}^{-n}$ | $-O-C_{22}H_{45}{}^{-n}$ |
| A-27 | 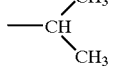 | $-O-C_{18}H_{37}{}^{-n}$ |
| A-28 | $-C_8H_{17}{}^{-n}$ | A |
| A-29 | $-CH_3$ | A |
| A-30 | $-C_2H_5$ | B |
| A-31 | $-H$ | $-N-(C_8H_{17}{}^{-n})_2$ |
| A-32 | $-CH_3$ | $-N-(C_4H_9{}^{-n})_2$ |
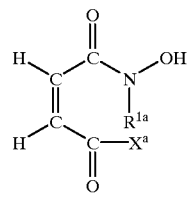
| Compound No. | $R^{1a}$ | $X^a$ |
|---|---|---|
| A-33 | $C_2H_5$ | $-O-C_{18}H_{37}{}^{-n}$ |
| A-34 | $CH_3$ | $-O-C_{16}H_{33}{}^{-n}$ |
| A-35 | | $-O-C_{22}H_{45}{}^{-n}$ |
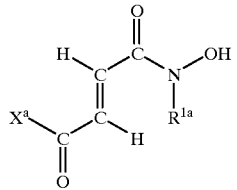

-continued

| | | |
|---|---|---|
| A-36 | —C$_4$H$_9$$^{-n}$ | —O—C$_{18}$H$_{37}$$^{-n}$ |
| A-37 | —CH$_2$CH$_2$CN | A |
| A-38 | —CH$_3$ | B |
| A-39 | —CH$_3$ | —N—(C$_8$H$_{17}$$^{-n}$)$_2$ |

A-40    —C$_2$H$_5$

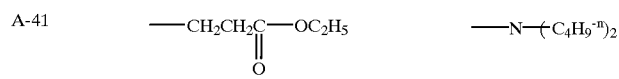

A-41    —CH$_2$CH$_2$C(=O)—OC$_2$H$_5$    —N—(C$_4$H$_9$$^{-n}$)$_2$

A-42    —H    —O—C$_{18}$H$_{37}$$^{-n}$

A-43

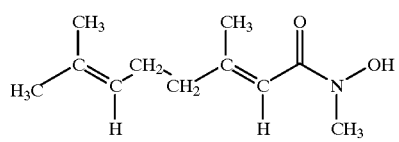

A-44

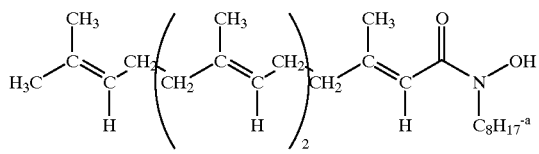

A-45

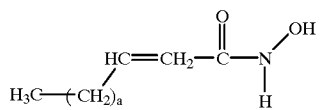

A-46

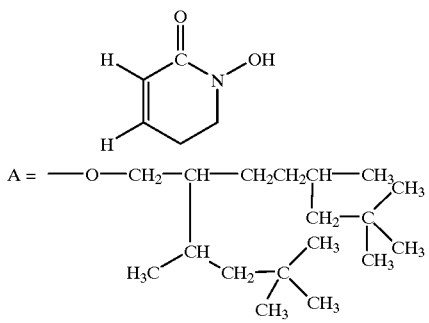

A = —O—CH$_2$—CH—CH$_2$CH$_2$CH—CH$_3$ ...

B = —(CH$_2$)$_8$CH=CH—(CH$_2$)$_7$CH$_3$

The synthesis method in general of the compound for use in the present invention is described below.

The compound for use in the present invention is obtained by condensing a corresponding carboxylic acid chloride with hydroxylamine or a N-substituted hydroxylamine. The carboxylic acid chloride can be easily obtained, when the corresponding carboxylic acid is easily available, by treating the carboxylic acid with thionyl chloride or oxalyl chloride. In the case of a complex carboxylic acid, a carboxylic acid is synthesized by a method according to respective cases and then treated with thionyl chloride or oxalyl chloride. The carboxylic acid can be synthesized in accordance with the following synthesis examples.

On the other hand, with respect to N-alkylhydroxylamine, those where the alkyl is a methyl group are commercially available and others can be synthesized according to the following methods.

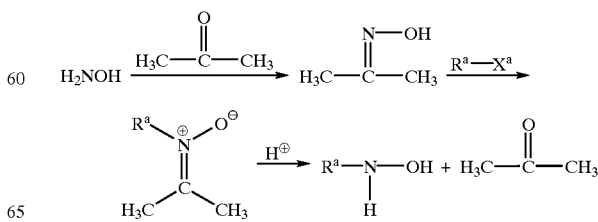

Acetone is added to hydroxylamine to convert it into acetoxime and the acetoxime is reacted with an alkylating agent to synthesize N-alkyl form (nitron). Thereafter, acetone is eliminated by performing acid treatment and as a result, N-alkylhydroxylamine is obtained.

The present invention is described in greater detail by referring to the following synthesis examples of the compound for use in the present invention.

SYNTHESIS EXAMPLE 1A

Synthesis of Compound A-1

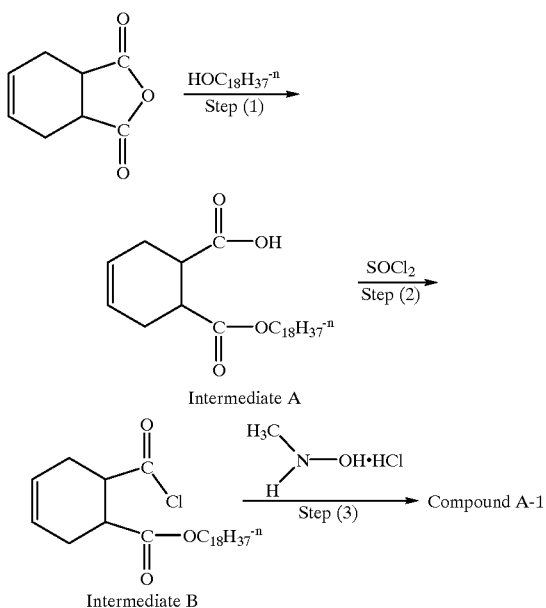

Step 1

Cis-4-cyclohexene-1,2-dicarboxylic anhydride (9.13 g (60 mmol)) and 16.2 g (60 mmol) of stearyl alcohol were mixed and the mixture was reacted at 120° C. for 2 hours and cooled to obtain Intermediate A.

Step 2

To a mixture of the entire amount of Intermediate A, 20 ml of methylene chloride and 0.5 ml of dimethylformamido, 8.6 g (72 mmol) of thionyl chloride was added, and the resulting mixture was reacted at 30° C. for 1 hour. After completion of the reaction, the remaining thionyl chloride and methylene chloride was removed under reduced pressure by means of an aspirator to obtain 23.5 g (55.6 mmol) of Intermediate B (yield: 92.7%).

Step 3

To 7.52 g (90 mmol) of N-methylhydroxylamine hydrochloride, 3.6 g (90 mmol) of sodium hydroxide, 100 ml of water, 15.1 g (180 mmol) of sodium hydrocarbonate and 100 ml of ethyl acetate under ice cooling while stirring, a mixture containing the entire amount (55.6 mmol) of Intermediate B and 50 ml of ethyl acetate was added dropwise. After the reaction for 30 minutes, the extraction was performed and the organic layer was washed with water twice and dried over anhydrous magnesium sulfate. Then, the solvent was distilled off and the crude product was purified by a silica gel column chromatography (ethyl acetate/hexane=1:2) to obtain 19.6 g (43.4 mmol) of Compound A-1 (yield: 78.0%).

The compound was identified by NMR and Mass spectra.
$^1$H NMR (200 MHz) δ (CDCl$_3$): 0.90 (3H, t, J=6 Hz), 1.22 (32H, bs), 1.50–1.85 (4H, m), 2.38 (2H, bs), 2.45–3.00 (4H, m), 3.32 (3H, bs), 4.10 (2H, t, J=6 Hz), 5.60–5.90 (2H, m), 7.20 (1H, s).

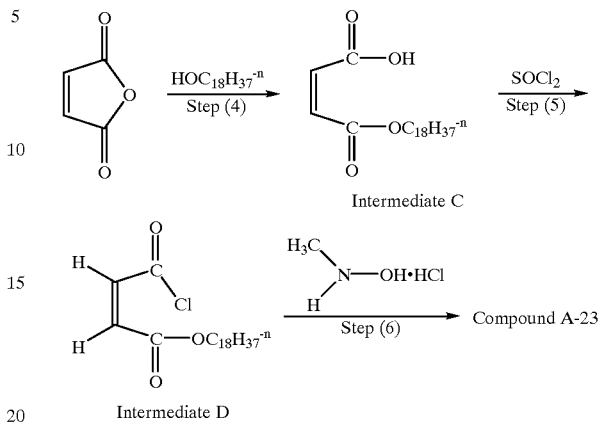

SYNTHESIS EXAMPLE 2A

Synthesis of Compound A-23

Step 4

Maleic anhydride (6.2 g (63 mmol)) and 16.2 g (60 mmol) of stearyl alcohol were mixed and the mixture was reacted at 120° C. for 2 hours. To the reaction solution, 10 ml of water was added, and the resulting mixture was reacted at 80° C. for 10 minutes, cooled and subjected to liquid separation by adding thereto 100 ml of ethyl acetate and 100 ml of water. The organic layer was washed with water twice, dried over anhydrous magnesium sulfate and distilled off under reduced pressure to obtain 21.8 g of Intermediate C (yield: 98.4%).

Step 5

To a mixture of 21.8 g (59 mmol) of Intermediate C with 20 ml of methylene chloride and 0.5 g of dimethylformamido, 7.9 g (66 mmol) of thionyl chloride was added dropwise. After reaction at 20° C. for 1 hour, the remaining thionyl chloride and methylene chloride were distilled off under reduced pressure by means of an aspirator to obtain Intermediate D. Intermediate D was used as it was in the next step.

Step 6

To a mixture of 7.5 g (90 mmol) of N-methylhydroxylamine hydrochloride with 3.6 g (90 mmol) of sodium hydroxide, 100 ml of water, 15.1 g (180 mmol) of sodium hydrocarbon and 100 ml of ethyl acetate under stirring at 15° C., a mixture containing the entire amount of Intermediate D and 50 ml of ethyl acetate was added dropwise. After reaction for 30 minutes, the reaction mixture was subjected to liquid separation by raising the temperature to 25° C. The organic layer was washed with water twice, dried over anhydrous magnesium sulfate and distilled off under reduced pressure. The crude product was purified by a silica gel column chromatography (ethyl acetate/hexane=1:2) to obtain 8.5 g of Compound A-23 (yield: 36.2%).

The hydroxamic acid compound having a bicyclo ring as a partial structure for use in the present invention preferably has a bicyclo[1,1,1], [2,1,1], [2,2,1] or [2,2,2] ring structure as a partial structure.

Among these, those where the bicyclo ring is directed connected to the hydroxyaminocarbonyl group are preferred, and the compound represented by formula (IB) is more preferred.

The compound represented by formula (IB) is described in detail below.

$R^{1b}$ represents a hydrogen atom, a substituted or unsubstituted alkyl group having from 1 to 30 carbon atoms, a substituted or unsubstituted cycloalkyl group having from 5 to 30 carbon atoms, a substituted or unsubstituted alkenyl group having from 3 to 30 carbon atoms or a substituted or unsubstituted cycloalkenyl group having from 5 to 30 carbon atoms.

When $R^{1b}$ represents an alkyl group, $R^{1b}$ preferably has a carbon number of from 1 to 6. When $R^{1b}$ represents an alkenyl group, $R^{1b}$ preferably has a carbon number of from 3 to 6. Preferred examples thereof include methyl, ethyl, allyl, n-propyl, isopropyl, n-butyl, sec-butyl, t-butyl, n-pentyl, isopentyl, neopentyl, n-hexyl and prenyl.

Examples of the substituent for the alkyl group or the alkenyl group include an alkyl group, an alkenyl group, an aryl group, a heterocyclic group, a halogen atom, an alkoxy group, an aryloxy group, an alkylthio group, an arylthio group, a cyano group, a nitro group, an alkoxycarbonyl group, an aryloxycarbonyl group, a hydroxyl group, an acyl group, an acyloxy group, an alkylsulfonyl group, an arylsulfonyl group, an acylamino group, an alkylsulfonamido group and an arylsulfonamido group. Specific examples thereof include 2-chloroethyl, 2-methoxyethyl, 2-cyanoethyl, 2-ethoxycarbonylethyl, 3-methylthiopropyl, 2-acetylaminoethyl, 3-hydroxypropyl, 2-acetyloxyethyl, 3-chloroethyl, 3-methoxyethylallyl and prenyl.

When $R^{1b}$ represents a cycloalkyl group or a cycloalkenyl group, $R^{1b}$ preferably has a carbon atom number of from 5 to 12. Preferred specific examples thereof include a cyclopentyl group, a cyclohexyl group, a 1-cyclohexen-1-yl group and 2-cyclohexen-1-yl group.

$R^{1b}$ is preferably an unsubstituted alkyl group having from 1 to 6 carbon atoms, more preferably a methyl group or an ethyl group.

$R^{2b}$ represents a substituted or unsubstituted bicycloalkyl group having from 5 to 40 carbon atoms or a substituted or unsubstituted bicycloalkenyl group having from 5 to 40 carbon atoms.

$R^{2b}$ preferably has a bicyclo[2,2,1], [2,2,2], [1,1,1] or [2,1,1] ring structure.

In the present invention, the bicycloalkyl group means a monovalent group obtained by removing one hydrogen of an aliphatic saturated hydrocarbon, namely, bicycloalkane, constituted only by two rings covalently having two or more atoms. The bicycloalkenyl group means a monovalent group obtained by removing one hydrogen of an aliphatic unsaturated hydrocarbon, namely, bicycloalkene, constituted only by two rings having at least one double bond and covalently having two or more atoms.

Among the compounds represented by formula (IB), preferred are those represented by formulae (IIB) and (IIIB).

In formulae (IIB) and (IIIB), $R^{1b}$ represents a hydrogen atom, a substituted or unsubstituted alkyl group having from 1 to 30 carbon atoms, a substituted or unsubstituted cycloalkyl group having from 5 to 30 carbon atoms, a substituted or unsubstituted alkenyl group having from 3 to 30 carbon atoms or a substituted or unsubstituted cycloalkenyl group having from 5 to 30 carbon atoms;

$R^{3b}$ and $R^{4b}$, which may be the same or different, each represents a hydrogen atom or a substituted or unsubstituted alkyl group having from 1 to 30 carbon atoms; and $Q^{1b}$, $Q^{2b}$ and $Q^{3b}$ each independently represents an atomic group necessary for forming a bicyclo ring by combining with the carbon atoms at both terminals.

Specific examples and preferred examples of $R^{1b}$ are the same as those of $R^{1b}$ in formula (IB).

When $R^{3b}$ and $R^{4b}$ each represents an alkyl group, $R^{3b}$ and $R^{4b}$ each preferably has a carbon atom number of from 1 to 20, more preferably from 1 to 8.

Specific examples of $R^{3b}$ and $R^{4b}$ include those described above for $R^{1b}$ in formula (IB).

$R^{3b}$ and $R^{4b}$ each is preferably a hydrogen atom or a methyl group.

$Q^{1b}$, $Q^{2b}$ and $Q^{3b}$ each preferably forms a bicyclo[1,1,1], [2,1,1], [2,2,1] or [2,2,2] ring structure.

$Q^{1b}$, $Q^{2b}$ and $Q^{3b}$ each more preferably forms a [2,2,1] or [2,2,2] ring.

In formula (IIB), a [2,2,1] ring is preferred.

In formula (IIIB), a [2,2,2] ring is preferred.

In a preferred structure of the compound represented by formula (IIB), $R^{1b}$ is an alkyl group having from 1 to 6 carbon atoms, $R^{3b}$ and $R^{4b}$ each is a hydrogen atom, and $Q^{1b}$, $Q^{2b}$ and $Q^{3b}$ each forms a bicyclo[2,2,1] ring.

In a preferred structure of the compound represented by formula (IIIB), $R^{1b}$ is an alkyl group having from 1 to 6 carbon atoms, $R^{3b}$ is a hydrogen atom or an alkyl group having from 1 to 3 carbon atoms, and $Q^{1b}$, $Q^{2b}$ and $Q^{3b}$ each forms a bicyclo[2,2,2] ring.

A more preferred structure of the compound represented by formula (IB) is the structure represented by formula (VIB):

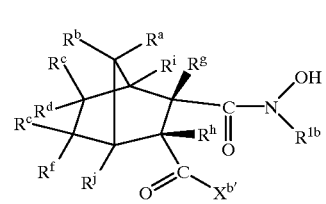

(VIB)

wherein $R^{1b}$ has the same meaning as $R^{1b}$ in formula (IB);

$X^{b'}$ represents $-OR^k$ or $-NR^kR^l$ (wherein $R^k$ and $R^l$, which may be the same or different, each independently represents a hydrogen atom, a substituted or unsubstituted alkyl group having from 1 to 30 carbon atoms, a substituted or unsubstituted aryl group having from 6 to 30 carbon atoms, a substituted or unsubstituted alkenyl group having from 2 to 30 carbon atoms or a substituted or unsubstituted cycloalkyl group having from 5 to 7 carbon atoms, and $R^k$ and $R^l$ may be combined with each other to form a ring structure); and $R^a$, $R^b$, $R^c$, $R^d$, $R^e$, $R^f$, $R^g$, $R^h$, $R^i$ and $R^j$, which may be the same or different, each independently represents a hydrogen atom or a substituted or unsubstituted alkyl group having from 1 to 6 carbon atoms, and $R^c$ and $R^f$ may be combined to form a double bond.

Specific examples and preferred examples of $R^{1b}$ are the same as those of $R^{1b}$ in formula (IB).

When $X^{b'}$ is $-OR^k$, $R^k$ is preferably a substituted or unsubstituted alkyl group having from 1 to 30 carbon atoms or a substituted or unsubstituted alkenyl group having from 3 to 30 carbon atoms.

When $R^k$ is the alkyl group, the alkyl group may be either branched or linear.

In this case, examples of the substituent of the alkyl group include an alkyl group, a halogen atom, a carboxyl group, an aryl group, a cyano group, a sulfamoyl group, an acyl group, a carbamoyl group, an alkoxycarbonyl group, an aryloxycarbonyl group, an acylamino group, an aryloxycarbonylamino group, a sulfonylamino group, an aminocarbonylamino group, a sulfamoylamino group, an amino group, an alkoxy group, an aryloxy group, a heterocyclic oxy group, an alkylthio group, an arylthio group, a heterocyclic thio group, a heterocyclic group, an alkylsulfonyl group or an arylsulfonyl group.

Specific examples of the alkyl group represented by $R^k$ are set forth below.

In the following chemical formula:

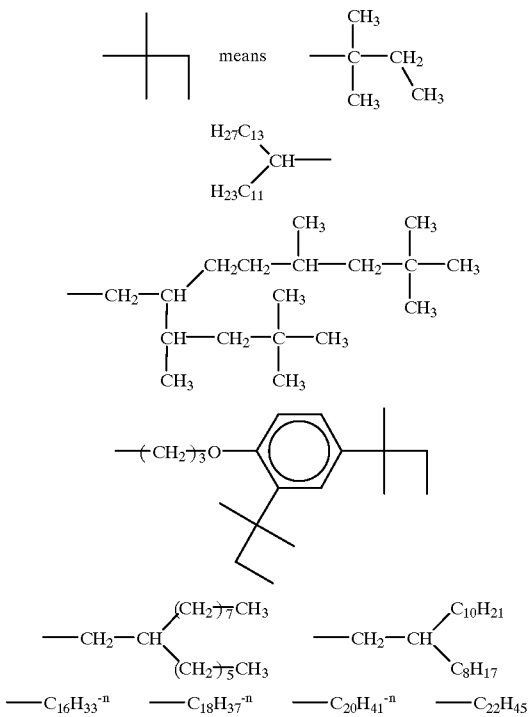

In addition, specific examples include the alkyl groups described above for $R^{1b}$. Specific examples of —O—$R^k$ further include alkoxy groups derived from a higher alcohol such as Fine Oxocol (trade name, produced by Nissan Chemical KK) 1400, 1600, 1800, 180, 180N, 2000 and 2600.

Specific examples of the alkenyl group include allyl homoallyl, prenyl and geranyl.

Specific examples of the aryl group include phenyl, 2-naphthyl and 2,4-di-t-pentylphenyl.

Examples of the cycloalkyl group represented by $R^k$ include cyclohexyl, cyclopentyl and cycloheptyl. Examples of the substituent of the cycloalkyl group include an alkoxy group, an alkyl group, an acylamino group, an aminocarbonylamino group, an alkoxycarbonylamino group, an aryloxycarbonylamino group, an alkoxycarbonyl group and an aminocarbonyl group.

When $X^{b'}$ is —$NR^kR^l$, $R^k$ and $R^l$, which may be the same or different, each independently is a hydrogen atom, a substituted or unsubstituted alkyl group having from 1 to 30 carbon atoms, a substituted or unsubstituted cycloalkyl group having from 5 to 30 carbon atoms, a substituted or unsubstituted aryl group having from 6 to 30 carbon atoms or a substituted or unsubstituted alkenyl group having from 2 to 30 carbon atoms. The specific examples of the alkyl, aryl, cycloalkyl or alkenyl group include those described above for $R^k$.

When $X^{b'}$ is —$NR^kR^l$, $R^k$ and $R^l$, which may be the same or different, each preferably is a substituted or unsubstituted alkyl group having from 6 to 30 carbon atoms.

Specific examples of $R^a$, $R^b$, $R^c$, $R^d$, $R^e$, $R^f$, $R^g$, $R^h$, $R^i$ and $R^j$ include hydrogen, methyl, ethyl, n-propyl, isopropyl, n-butyl, t-butyl, n-hexyl and n-pentyl.

$R^a$ and $R^b$ are preferably a hydrogen atom at the same time or a methyl group at the same time.

$R^c$ and $R^f$ are preferably a hydrogen atom at the same time or combined with each other to form a double bond.

$R^d$, $R^e$, $R^g$, $R^h$, $R^i$ and $R^j$ each is preferably a hydrogen atom.

In a preferred embodiment of formula (VIB), $R^a$, $R^b$, $R^d$, $R^e$, $R^g$, $R^h$, $R^i$ and $R^j$ are a hydrogen atom at the same time, $R^c$ and $R^f$ are a hydrogen atom at the same time or are combined to form a double bond, $X^{b'}$ is —$NR^kR^l$, $R^k$ and $R^l$, which may be the same or different, each is a substituted or unsubstituted alkyl group having from 6 to 30 carbon atoms, and $R^{1b}$ is an unsubstituted alkyl group having from 1 to 6 carbon atoms.

The structure represented by formula (VIB) is more preferably represented by formula (IVB) or (VB):

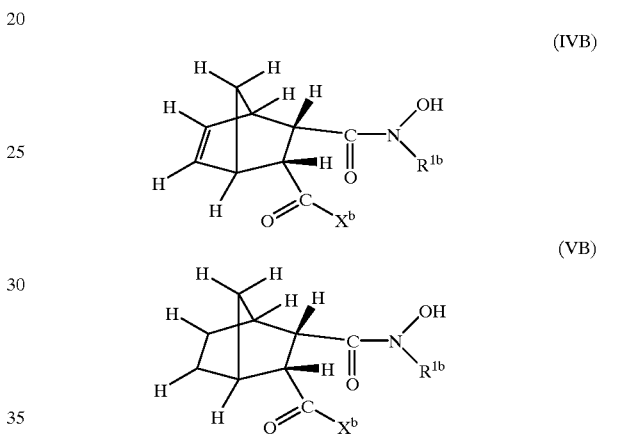

wherein $R^{1b}$ has the same meaning as $R^{1b}$ in formula (IB);

$X^b$ represents —$OR^{5b}$ or —$N(R^{5b})(R^{6b})$ (wherein $R^{5b}$ and $R^{6b}$, which may be the same or different, each independently represents a hydrogen atom, a substituted or unsubstituted alkyl group having from 1 to 30 carbon atoms, a substituted or unsubstituted cycloalkyl group having from 5 to 30 carbon atoms or a substituted or unsubstituted aryl group having from 6 to 30 carbon atoms, and $R^{5b}$ and $R^{6b}$ are combined with each other to form a ring structure);

$R^{1b}$ is preferably an alkyl group having from 1 to 6 carbon atoms, and $R^{5b}$ and $R^{6b}$ each is preferably an alkyl group having from 10 to 22 carbon atoms or a substituted or unsubstituted cycloalkyl group having from 5 to 7 carbon atoms.

$R^{1b}$ is more preferably methyl, ethyl, n-propyl or n-hexyl, still more preferably an alkyl group having from 1 to 6 carbon atoms.

In a preferred embodiment of the formulae, $X^b$ is —O—$R^{5b}$ (wherein $R^{5b}$ is a linear alkyl group having a carbon atom number of 14, 16, 18, 20 or 22) or —$N(R^{5b})(R^{6b})$ (wherein $R^{5b}$ and $R^{6b}$ each is a hydrogen atom or a substituted or unsubstituted alkyl group having from 8 to 20 carbon atoms) and $R^{1b}$ is an unsubstituted alkyl group having from 1 to 6 carbon atoms.

In a more preferred embodiment, $X^b$ is —$N(R^{5b})(R^{6b})$ (wherein $R^{5b}$ and $R^{6b}$ are simultaneously a substituted or unsubstituted having from 8 to 18 carbon atoms) and $R^{1b}$ is a methyl group, an ethyl group, an n-propyl group or an isopropyl group.

The compound for use in the present invention allows the presence of an antipode and if it is present, the antipode which can be used in the present invention may be either an optically active substance or a racemic modification.

Because of the low cost, the racemic modification is preferred.

Specific examples of the present invention are set forth below, however, the present invention is by no means limited thereto.

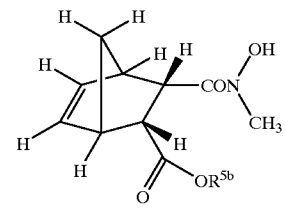

| Compound | $R^{5b}$ |
|---|---|
| B-1 | $-C_{18}H_{37}{}^{-n}$ |
| B-2 | $-C_{16}H_{33}{}^{-n}$ |
| B-3 | $-C_{14}H_{29}{}^{-n}$ |
| B-4 | $-C_{12}H_{25}{}^{-n}$ |
| B-5 | $-C_{20}H_{11}{}^{-n}$ |
| B-6 | $-C_{22}H_{45}{}^{-n}$ |

B-7

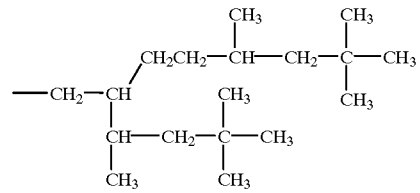

B-8

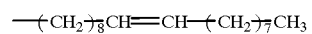

B-9

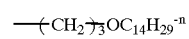

B-10

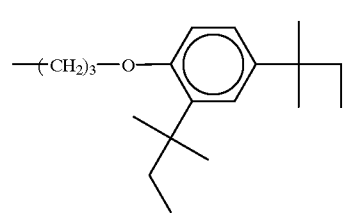

B-11

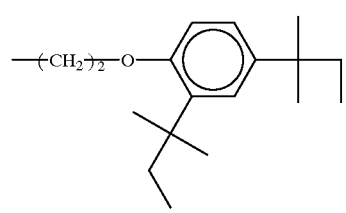

B-12

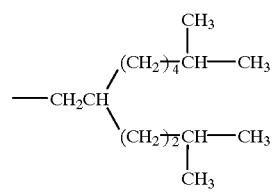

-continued
B-13 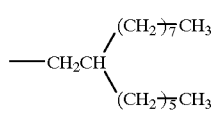
B-14 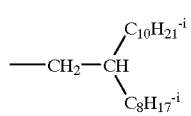
B-15 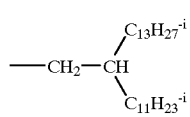
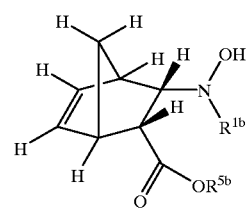
| Compound | $R^{5b}$ | $R^{1b}$ |
|---|---|---|
| B-16 | —$C_{18}H_{37}^{-n}$ | —$C_2H_5$ |
| B-17 | —$C_{16}H_{33}^{-n}$ | —$C_3H_7^{-n}$ |
| B-18 | —$C_{14}H_{29}^{-n}$ | —$C_5H_{11}^{-n}$ |
| B-19 | —$C_{12}H_{25}^{-n}$ | —$C_8H_{17}^{-n}$ |
| B-20 | —$C_{10}H_{21}^{-n}$ | —$C_{12}H_{25}^{-n}$ |
| B-21 | 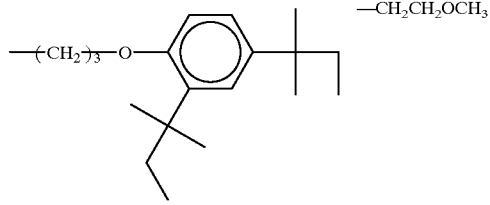 | —$CH_2CH_2OCH_3$ |
| B-22 | " | —$CH_2CH_2$—CN |
| B-23 | 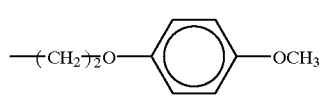 | —$C_3H_7^{-i}$ |
| B-24 | —$(CH_2)_2$O—$(CH_2)_2$OCH$_3$ | —$C_5H_{21}^{-n}$ |
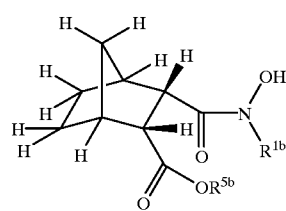
| Compound | $R^{5b}$ | $R^{1b}$ |
|---|---|---|
| B-25 | —$C_{18}H_{37}^{-n}$ | CH$_3$ |
| B-26 | —$C_{16}H_{33}^{-n}$ | —$C_2H_5$ |

-continued
| | | |
|---|---|---|
| B-27 | 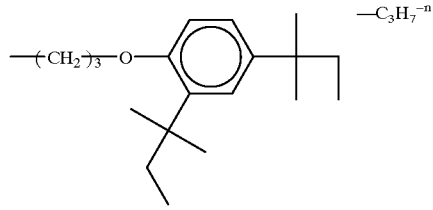 | $-C_3H_7{}^{-n}$ |
| B-28 | 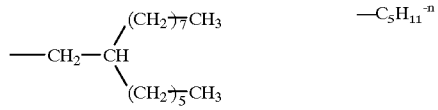 | $-C_5H_{11}{}^{-n}$ |
| B-29 | $-C_{20}H_{41}{}^{-n}$ | H |
| B-30 | $-C_{14}H_{29}{}^{-n}$ | 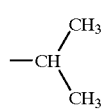 |
| | |
|---|---|
| B-31 | 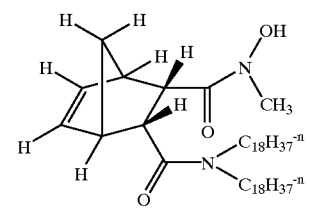 |
| B-32 | 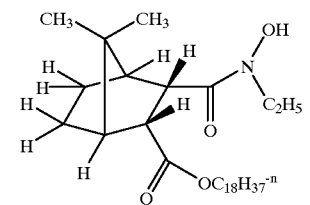 |
| B-33 | 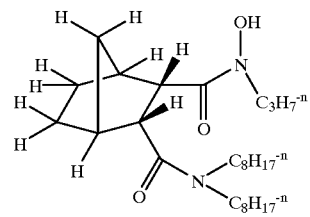 |
| B-34 | 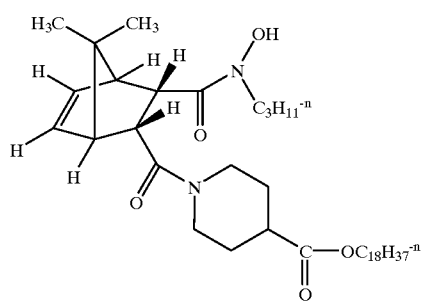 |

-continued
B-35 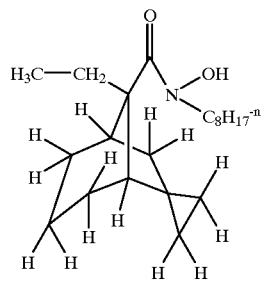
B-36 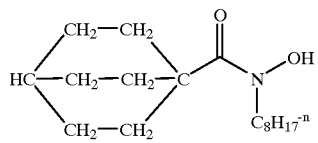
B-37 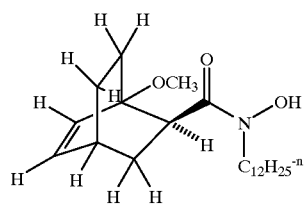
B-38 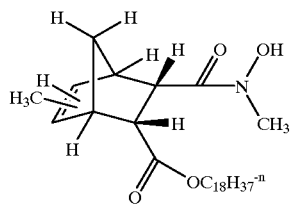
B-39 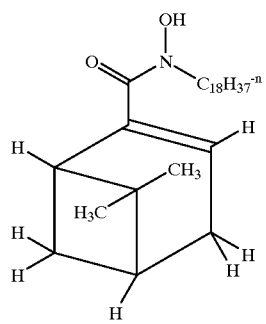
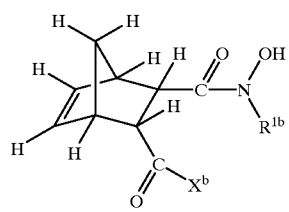
| Compound | $X^b$ | $R^{1b}$ |
|---|---|---|
| B-40 | 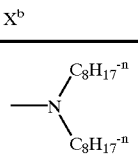 |  —$CH_3$ |

-continued
| | | |
|---|---|---|
| B-41 |  | —CH₃ |
| B-42 |  | —CH₃ |
| B-43 |  | —CH₃ |
| B-44 |  | —CH₃ |
| B-45 | 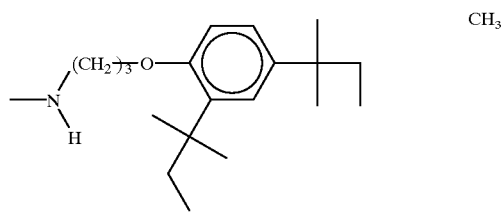 | CH₃ |
| B-46 |  | —C₂H₅ |
| B-47 |  | —C₈H₁₇⁻ⁿ |
| B-48 |  | —C₃H₇⁻ⁿ |
| B-49 | 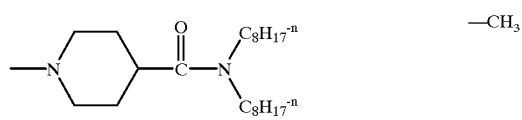 | —CH₃ |
| B-50 |  | —C₈H₁₇⁻ⁿ |

-continued
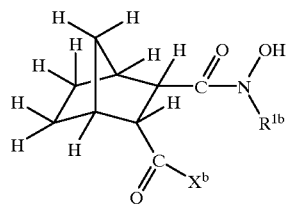
| Compound | $X^b$ | $R^{1b}$ |
|---|---|---|
| B-51 | —N(C$_8$H$_{17}$-n)$_2$ | —CH$_3$ |
| B-52 | —N(C$_{18}$H$_{37}$-n)$_2$ | —CH$_3$ |
| B-53 | —O—C$_{18}$H$_{37}$-n | —CH$_3$ |
| B-54 | —O—CH$_2$—CH(CH$_2$CH$_2$CH(CH$_3$)CH$_2$C(CH$_3$)$_3$)(CH(CH$_3$)CH$_2$C(CH$_3$)$_3$) | —CH$_3$ |
| B-55 | 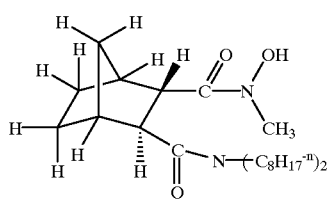 | —CH$_3$ |
| B-56 | —O—C$_{18}$H$_{37}$-iso | —CH$_3$ |
| B-57 | 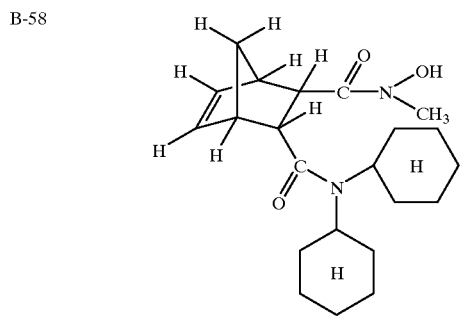 | |
| B-58 | | |

-continued

B-59

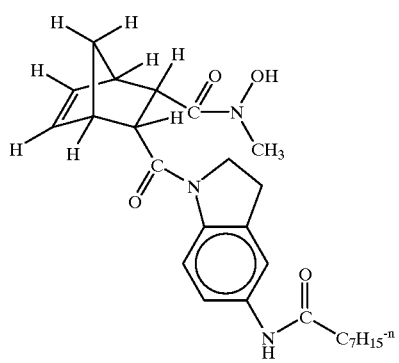

B-60

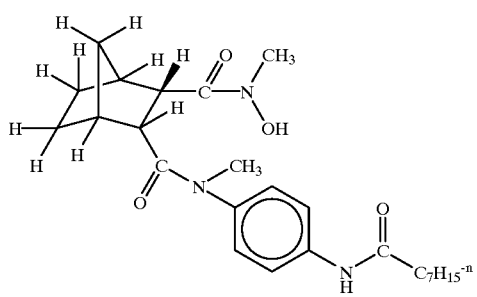

In the above-described compounds, Compound B-56 was synthesized from Fine Oxocol 180N.

When these compounds allow the presence of an antipode, it is a racemic modification in all cases, except that in the case of Compound B-39, it is an optically active substance.

The compound represented by formula (IB) has a molecular weight, when it is used to improve storability of a specific layer, of preferably 300 or more, more preferably 350 or more and most preferably 400 or more.

When the compound for use in the present invention is used only to improve storability of a specific layer, it should be substantially insoluble in water so that it does not diffuse into the gelatin layer. The term "substantially insoluble in water" as used herein means that the solubility at 25° C. in water is 5% or less, preferably 1% or less.

The synthesis method in general of the compound for use in the present invention is described below.

The compound for use in the present invention is obtained by condensing a corresponding carboxylic acid chloride with N-alkylhydroxylamine. The carboxylic acid chloride can be easily obtained, when the corresponding carboxylic acid is easily available, by treating the carboxylic acid with thionyl chloride or oxalyl chloride. In the case of a complex carboxylic acid, a carboxylic acid is synthesized by a method according to respective cases and then treated with thionyl chloride or oxalyl chloride. The carboxylic acid can be synthesized in accordance with the following synthesis examples.

On the other hand, with respect to N-alkylhydroxylamine, those where the alkyl is a methyl group are commercially available and others can be synthesized according to the following methods.

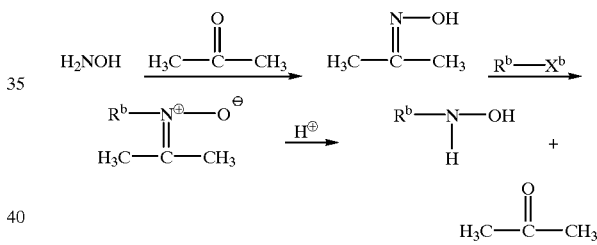

Acetone is added to hydroxylamine to convert it into acetoxime and the acetoxime is reacted with an alkylating agent to synthesize N-alkyl form (nitron). Thereafter, acetone is eliminated by performing acid treatment and as a result, N-alkylhydroxylamine is obtained.

The present invention is described in greater detail by referring to the following synthesis examples of the compound for use in the present invention.

SYNTHESIS EXAMPLE 1B

Synthesis of Compound B-1

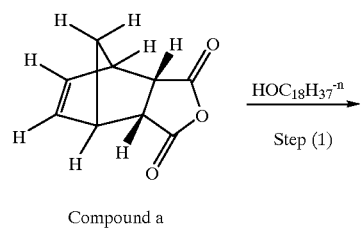

Compound a

-continued

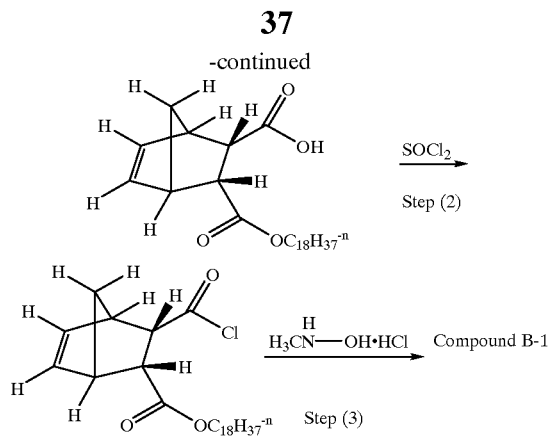

SYNTHESIS EXAMPLE 2B
Synthesis of Compound B-40

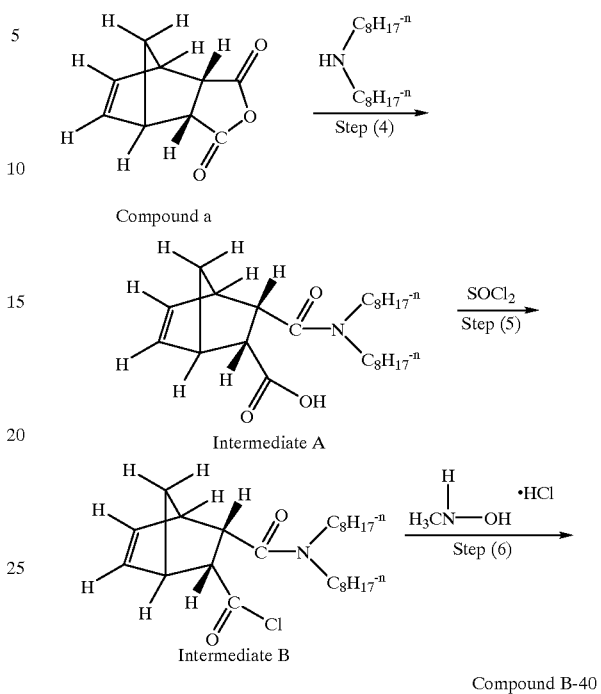

Step (1)

To a three-necked flask, 50 g (305 mmol) of Compound a and 82.5 g (305 mmol) of stearyl alcohol were added, and they were reacted at 80° C. for 6 hours. Thereto, 200 ml of ethyl acetate and 50 ml of acetonitrile were added and then allowed to cool to 20° C.

The crystals deposited were collected by filtration, washed by pouring 100 ml of acetonitrile thereon and then dried to obtain 105 g of Compound b (yield: 79.3%).

Step (2)

To a three-necked flask, 30 g (69.0 mmol) of Compound b, 30 ml of methylene chloride and 0.1 ml of dimethylformamido were added, and thereto 9.0 g of thionyl chloride was added dropwise while stirring. Thereafter, the mixture was reacted at 40° C. for 1 hour and then, methylene chloride and excessive thionyl chloride were distilled off under reduced pressure.

The residue obtained was used as it was in the next step.

Step (3)

To a three-necked flask, 100 ml of water, 3.31 g (82.8 mmol) of sodium hydroxide and 6.92 g (82.8 mmol) of N-methylhyroxylamine hydrochloride were added and stirred under a nitrogen gas stream and thereto 13.9 g (166 mmol) of sodium hydrocarbon and 100 ml of ethyl acetate was added, followed by cooling to 15° C. To the resulting solution, a solution having dissolved therein the entire amount of Compound b prepared in the previous step and 100 ml of ethyl acetate was added dropwise.

After the dropwise addition, the mixture was reacted for 30 minutes and subjected to liquid separation after the temperature thereof was raised to 50° C. The organic layer was washed with water twice and then crystallized by adding 100 ml of acetonitrile to the organic layer.

The crystals obtained were collected by filtration, washed with acetonitrile and then dried to obtain 18.1 g (49.5 mmol) of Compound B-1 (yield: 71.7%).

NMR Spectrum (300 MHz) δ (CDCl$_3$): 0.90 (3H, t, J6.8), 1.16–1.42 (30H, m), 1.48 (1H, d, J7.6), 1.55–1.68 (2H, m), 3.05 (1H, bs), 3.15 (3H, s), 3.20–3.40 (2H, m), 3.46 (1H, d, d, J$_1$ 11.4, J$_2$ 4), 3.70 (1H, d, d, J$_1$ 11.4, J$_2$ 4), 3.86–4.09 (2H, m), 6.07 (1H, bs), 6.57 (1H, bs), 7.78 (1H, bs).

mp=111–112° C.

Step (4)

Di-n-octylamine (50.3 g), 100 ml of acetonitrile and 21.1 g of triethylamine were mixed and thereto a solution having dissolved therein 34.2 g of Compound a and 50 ml of acetonitrile was added dropwise under ice cooling. The dropwise addition was performed so that the temperature of the reaction solution could be from 15 to 18° C. The mixture was reacted for 15 minutes and then subjected to liquid separation by adding thereto water and ethyl acetate. The organic layer was washed with water twice and dried over magnesium sulfate, and then the solvent was distilled off under reduced pressure to obtain Intermediate A. Intermediate A was used as it was in the next step.

Step (5)

Into the entire amount of Intermediate A, 50 ml of methylene chloride and 0.3 ml of dimethylformamido were added and dissolved, and thereto 29.7 g of thionyl chloride was added dropwise at 20° C. After the mixture was reacted at 40° C. for 20 minutes, the remaining thionyl chloride and methylene chloride were distilled off under reduced pressure by means of an aspirator to obtain Intermediate B. Intermediate B was used as it was in the next step.

Step (6)

Water (250 ml), 10.4 g of sodium hydroxide and 21.7 g of N-methylhydroxylamine hydrochloride were dissolved at 10° C. under a nitrogen gas stream. Then, 43.7 g of sodium hydrocarbon and 300 ml of ethyl acetate were added and thereto a solution obtained by dissolving the entire amount of Intermediate B into 100 ml of ethyl acetate was added dropwise while keeping the reaction temperature at from 15 to 20° C. The reaction solution was subjected to liquid separation by raising the temperature to 50° C. The organic layer was washed with water twice and dried over magnesium sulfate, and then the solvent was distilled off under reduced pressure. The residue was crystallized with acetonitrile. The crude crystals obtained were dissolved in 250 ml of hexane and heat filtered, and after removing the filtrate by distillation under reduced pressure, the residue was recrystallized with a mixed solvent of 50 ml of ethyl acetate, 25 ml of methanol and 250 ml of acetonitrile to obtain 30.1 g of Compound B-40 (yield: 33.4%)

300 MHz $^1$H NMR spectrum δ (CDCl$_3$): 0.90 (3H, t), 0.91 (3H, t), 1.06–1.41 (20H, m), 1.41–1.92 (6H, m), 2.82–3.77 (8H, m), 3.16 (3H, s), 5.85–6.20 (1H, m), 6.40–6.68 (1H, m).

SYNTHESIS EXAMPLE 3B

Synthesis of Compound B-51

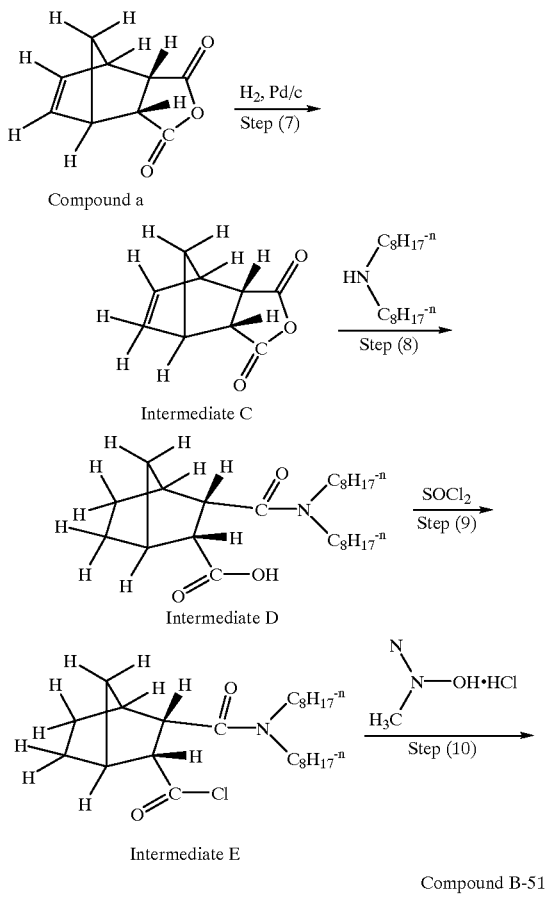

Step (7)

Into an autoclave, 50 g of Compound a, 1.0 g of Pd/c (10 wt %) and 400 ml of acetic acid were charged, and thereto hydrogen was added at 100° C. at a pressure of 30 kg/cm$^2$. After cooling for 4 hours, the reaction solution was poured into water and crystals deposited were collected by filtration. The crystals were washed with acetonitrile and dried to obtain 26.2 g of Intermediate C (yield: 51.8%).

Step (8)

Under ice cooling, 20.1 g of di-n-octylamine, 50 ml of acetonitrile and 8.4 g of triethylamine were stirred, and thereto a solution obtained by dissolving 14.0 g of Intermediate C into 50 g of acetonitrile was added dropwise. After the reaction, the reaction solution was subjected to liquid separation by adding ethyl acetate and water. The organic layer was washed with water twice and dried over magnesium sulfate. The solvent was distilled off under reduced pressure and then purified by a silica gel column chromatography (hexane:ethyl acetate=10:1 to 2:1) to obtain 10.5 g of Intermediate D (yield: 45.8%).

Step (9)

Intermediate C (10.0 g), 10 ml of methylene chloride and 0.2 ml of dimethylformamido were dissolved and thereto 3.5 g of thionyl chloride was added dropwise at 20° C. while stirring. The mixture was reacted at 40° C. for 2 hours and then the remaining thionyl chloride and methylene chloride were distilled of by means of an aspirator to obtain Intermediate E. Intermediate E was used as it was in the next step.

Step (10)

Under a nitrogen gas stream, 50 ml of water, 1.28 g of sodium hydroxide and 2.67 g of N-methylhydroxylamine hydrochloride were dissolved at 10° C. To the resulting solution, 5.38 g of sodium hydrocarbon and 50 ml of ethyl acetate were added and then a 50 ml ethyl acetate solution of the entire amount of Intermediate E was added dropwise while keeping the reaction temperature at from 10 to 15° C. The reaction solution was subjected to liquid separation after the temperature thereof was raised to 50° C. The organic layer was washed with water twice and dried over magnesium sulfate, and then the solvent was distilled off under reduced pressure. The crude product obtained was purified by a silica gel column chromatography to obtain 8.1 g of Compound B-51 (yield: 58.1%).

300 MHz $^1$H NMR δ (CDCl$_3$): 0.86 (6H, t), 1.15–1.38 (22H, m), 1.38–1.78 (10H, m), 2.27–2.57 (2H, m), 2.57–2.97 (2H, m), 3.07 (3H, s), 3.07–3.47 (2H, m).

Compound B-42 and Compound B-40 were synthesized in the same manner. The 300 MHz $^1$H NMR spectrum of Compound B-42 is shown below.

δ (CDCl$_3$): 1.23–1.58 (2H, m), 1.69–2.09 (5H, m), 3.05–3.32 (5H, m), 3.32–3.62 (5H, m), 6.11–6.42 (2H, m).

The addition amount of the compound for use in the present invention is not particularly restricted, however, when it is added to a light-sensitive silver halide emulsion layer, it is preferably from $1.0 \times 10^{-4}$ to $1.0 \times 10^{-1}$ mol, more preferably from $1.0 \times 10^{-3}$ to $5.0 \times 10^{-2}$ mol, per mol of Ag in the layer to which the compound is added. When the compound is added to a light-insensitive layer, the addition amount is preferably from $1 \times 10^{-6}$ to $3 \times 10^{-4}$ mol/m$^2$, more preferably from $1 \times 10^{-3}$ to $1 \times 10^{-4}$ mol/m$^2$.

The compound for use in the present invention may be added after dissolving it in a water-soluble solvent (e.g., methanol, ethanol, acetone) or after co-emulsifying it with a coupler by emulsion-dispersion. Further, the compound may be previously added at the preparation of an emulsion. The addition method using emulsion-dispersion is most preferred.

The layer to which the compound for use in the present invention is added is not particularly preferred, however, the compound is preferably added to a silver halide emulsion layer, more preferably to a red-sensitive layer and/or a green-sensitive layer.

When the present invention is applied to a color photographic material, the color photographic material may suffice if it has at least one light-sensitive layer on the support. A typical example thereof is a silver halide photographic material comprising a support having thereon at least one light-sensitive layer consisting of a plurality of silver halide emulsion layers having substantially the same spectral sensitivity but different light sensitivities. The light-sensitive layer is a unit light-sensitive layer having spectral sensitivity to any of blue light, green light and red light. In the case of a multi-layer silver halide color photographic material, the arrangement of unit light-sensitive layers are generally such that a red-sensitive unit layer, a green-sensitive unit layer and a blue-sensitive unit layer are provided in this order from the support side. However, depending upon the purpose, the above arrangement order may be reversed or a layer having different light sensitivity may be superposed between layers having the same spectral sensitivity. A light-insensitive layer may be provided between the above-described silver halide light-sensitive layers, as an uppermost layer or as the lowermost layer. These layers may contain a coupler, a DIR compound or a color mixing inhibitor which will be described later. Further, these layers may contain a compound which releases imagewise or reverse-imagewise dyes and causes difference in the diffusibility between the dye released and the compound before the release.

The silver halide emulsion layers in plurality constituting each unit light-sensitive layer are preferably arranged such that two layers of a high-sensitivity emulsion layer and a low-sensitivity emulsion layer are provided so that the light sensitivity can be lowered in sequence towards the support as described in German Patent 1,121,470 and British Patent 923,045. Further, it may also be possible to provide a low-sensitivity emulsion layer farther from the support and a high-sensitivity emulsion layer nearer to the support as described in JP-A-57-112751, JP-A-62-200350, JP-A-62-206541 and JP-A-62-206543.

Specific examples of the layer arrangement include an order, from the farthest side to the support, of a low-sensitivity blue-sensitive layer (BL)/a high-sensitivity blue-sensitive layer (BH)/a high-sensitivity green-sensitive layer (GH)/a low-sensitivity green-sensitive layer (GL)/a high-sensitivity red-sensitive layer (RH)/a low-sensitivity red-sensitive layer (RL), an order of BH/BL/GL/GH/RH/RL and an order of BH/BL/GH/GL/RL/RH.

Also, as described in JP-B-55-34932 (the term "JP-B" as used herein means an "examined Japanese patent publication"), a blue-sensitive layer/GH/RH/GL/RL may be arranged in this order from the farthest side to the support. Further, as described in JP-A-56-25738 and JP-A-62-63936, a blue-sensitive layer/GL/RL/GH/RH may be arranged in this order from the farthest side to the support.

An arrangement consisting of three layers different in the light sensitivity may be used as described in JP-B-49-15495 where a silver halide emulsion layer having the highest light sensitivity is provided as an upper layer, a silver halide emulsion layer having a light sensitivity lower than that of the upper layer as a medium layer and a silver halide emulsion layer having a light sensitivity lower than that of the medium layer as a lower layer so that the light sensitivity can be lowered in sequence towards the support. Even in the case when such a three layer structure having different light sensitivities is used, as described in JP-A-59-202464, a medium-sensitivity emulsion layer/a high-sensitivity emulsion layer/a low-sensitivity emulsion layer may be provided in this order from the farthest side to the support in the layer having the same spectral sensitivity.

In addition, an order of a high-sensitivity emulsion layer/a low-sensitivity emulsion layer/a medium-sensitivity emulsion layer or an order of a low-sensitivity emulsion layer/a medium-sensitivity emulsion layer/a high-sensitivity emulsion layer may also be used.

In the case of four or more layer structure, the layer arrangement may also be changed as described above.

In order to improve color reproducibility, a donor layer (CL) having a spectral sensitivity distribution different from that of main light-sensitive layers such as BL, GL and RL and capable of providing an interlayer effect, is preferably provided adjacent to or in the vicinity of a main light-sensitive layer as described in U.S. Pat. Nos. 4,663,271, 4,705,744 and 4,707,436, JP-A-62-160448 and JP-A-63-89850.

The silver halide grain in the photographic emulsion may have a regular crystal from such as cubic, octahedral or tetradecahedral, an irregular crystal form such as spherical or platy, a crystal defect such as twin, or a composite form of these.

The silver halide may be a fine grain having a grain size of about 0.2 $\mu$m or less or a large-sized grain having a grain size in terms of a projected area diameter up to about 10 $\mu$m, and either a polydisperse emulsion or a monodisperse emulsion may be used.

The silver halide photographic emulsion which can be used in the present invention can be prepared according to the methods described, for example, in *Research Disclosure* (herein-after referred to as "RD") No. 17643, pp. 22–23 "I. Emulsion Preparation and Types" (December, 1978), ibid., No. 18716, p. 648 (November, 1979), ibid., No. 307105, pp. 863–865 (November, 1989), P. Glafkides, *Chemie et Phisigue Photographique,* Paul Montel (1967), G. F. Duffin, *Photographic Emulsion Chemistry,* Focal Press (1966), and V. L. Zelikman et al., *Making and Coating Photographic Emulsion,* Focal Press (1964).

The monodisperse emulsions described in U.S. Pat. Nos. 3,574,628 and 3,655,394 and British Patent 1,413,748 are also preferably used.

Furthermore, tabular grains having an aspect ratio of about 3 or more can be used in the present invention. The tabular grain can be easily prepared by the methods described in Gutoff, *Photographic Science and Engineering,* Vol. 14, pp. 248–257 (1970), U.S. Pat. Nos. 4,434,226, 4,414,310, 4,433,048 and 4,439,520 and British Patent 2,112,157.

The crystal structure may be homogeneous, may comprise a halogen composition different between the interior and the exterior or may be stratified. A silver halide having a different composition may be conjugated thereto by an epitaxial junction or the silver halide may be conjugated with a compound other than silver halide, such as silver rhodanate or lead oxide. Also, a mixture of grains having various crystal forms may be used.

The above-described emulsion may be a surface latent image-type emulsion forming a latent image mainly on the surface, an internal latent image-type emulsion forming a latent image inside the grain, or a type forming a latent image both on the surface of and inside the grain. The emulsion may be either a negative type emulsion or a positive type emulsion (so-called autopositive emulsion). When it is a negative type emulsion, either a normal emulsion or a heat developable emulsion may be used. As one of internal latent image-type emulsions, a core/shell internal latent image-type emulsion described in JP-A-63-264740 may also be used and the preparation method of this emulsion is described in JP-A-59-133542. In this emulsion, the thickness of the shell varies depending upon the development process and the like, but it is preferably from 3 to 40 nm, more preferably from 5 to 20 nm.

The silver halide emulsion is usually subjected to physical ripening, chemical ripening and spectral sensitization before use. The additives used in these steps are described in *RD* No. 17643, *RD* No. 18716 and *RD* No. 307105 and the pertinent portions thereof are summarized in the table set forth later.

The photographic material of the present invention may use a mixture of two or more kinds of emulsions different at least in one property of the light-sensitive silver halide emulsion, such as the grain size, the grain size distribution, the halogen composition, the grain shape or the sensitivity, in the same layer.

It is preferred to apply a silver halide grain of which surface is fogged described in U.S. Pat. No. 4,082,553, a silver halide grain of which inside is fogged described in U.S. Pat. No. 4,626,498 and JP-A-59-214852 or a colloidal silver to a light-sensitive silver halide emulsion layer and/or a substantially light-insensitive hydrophilic colloid layer. The term "silver halide grain of which inside or surface is fogged" as used herein means a silver halide grain which can achieve uniform (non-imagewise) development of a photographic material irrespective of an unexposed area or an exposed area. The preparation method of such a grain is described in U.S. Pat. No. 4,626,498 and JP-A-59-214852. The silver halide forming the inside nucleus of a core/shell type silver halide grain of which inside is fogged may have a different halogen composition. The silver halide for the grain of which inside or surface is fogged may be any of silver chloride, silver bromide, silver iodobromide and silver chloroiodobromide. The fogged silver halide grain has an average grain size of preferably from 0.01 to 0.75 μm, more preferably from 0.05 to 0.6 μm. The grain may have a regular form or may be a polydisperse emulsion, but it is preferably monodisperse (namely, at least 95% by weight or by number of silver halide grains having a grain size within an average grain size ±40%).

In the present invention, a light-insensitive fine grain silver halide is preferably used. The term "light-insensitive fine grain silver halide" as used herein means a silver halide fine grain which is not sensitive to light at the imagewise exposure for obtaining a dye image and substantially not developed at the development process. The light-insensitive fine grain silver halide is preferably not fogged previously. The fine grain silver halide has a silver bromide content of from 0 to 100 mol % and may contain, if desired, silver chloride and/or silver iodide. It preferably contains from 0.5 to 10 mol % of silver iodide. The fine grain silver halide has an average grain size (an average of circle-corresponding diameters of the projected area) of preferably from 0.01 to 0.5 μm, more preferably from 0.02 to 0.2 μm.

The fine grain silver halide can be prepared by the same method as that for the normal light-sensitive silver halide. The surface of the silver halide grain needs not be optically sensitized nor be spectrally sensitized. However, it is preferred to add a known stabilizer such as a triazole-base compound, an azaindene-base compound, a benzothiazolium-base compound, a mercapto-base compound or a zinc compound, to the fine grain silver halide in advance of the addition to a coating solution. A layer containing the fine grain silver halide grain may contain colloidal silver.

The photographic material of the present invention has a coated silver amount of preferably 6.0 g/m² or less, most preferably 4.5 g/m² or less.

The photographic additives which can be used in the present invention are also described in RDs and the portions having description thereon are shown in the table below.

| Kinds of Additives | RD17643 | RD18716 | RD307105 |
|---|---|---|---|
| 1. Chemical sensitizer | p. 23 | p. 648, right col. | p. 866 |
| 2. Sensitivity increasing agent | | p. 648, right col. | |

-continued

| Kinds of Additives | RD17643 | RD18716 | RD307105 |
|---|---|---|---|
| 3. Spectral sensitizer, supersensitizer | pp. 23–24 | p. 648, right col.-p. 649, right col. | pp. 866–868 |
| 4. Whitening agent | p. 24 | p. 647, right col. | p. 868 |
| 5. Light absorbent, filter dye, UV absorbent | pp. 25–26 | p. 649, right col.-p. 650, left col. | p. 873 |
| 6. Binder | p. 26 | p. 651, left col. | pp. 873–874 |
| 7. Plasticizer, lubricant | p. 27 | p. 650, right col. | p. 876 |
| 8. Coating aid, surface active agent | pp. 26–27 | p. 650, right col. | pp. 875–876 |
| 9. Antistatic agent | p. 27 | p. 650, right col. | pp. 876–877 |
| 10. Matting agent | | | pp. 878–879 |

Various dye-forming couplers can be used in the photographic material of the present invention and the following couplers are particularly preferred.

Yellow Coupler

Couplers represented by formula (I) or (II) of EP-A-502424; couplers represented by formula (1) or (2) (particularly, Y-28 at page 18) of EP-A-513496; couplers represented by formula (I) in claim 1 of JP-A-5-307248; couplers represented by formula (I) in column 1, lines 45 to 55 of U.S. Pat. No. 5,066,576; couplers represented by formula (I) in paragraph 0008 of JP-A-4-274425; couplers (particularly, D-35 at page 18) described in claim 1 at page 40 of EP-A-498381; couplers represented by formula (Y) at page 4 (particularly, Y-1 (page 17) and Y-54 (page 41)) of EP-A-447969; couplers represented by any one of formulae (II) to (IV) in column 7, lines 36 to 58 (particularly, II-17, II-19 (column 17) and II-24 (column 19)) of U.S. Pat. No. 4,476,219.

Magenta Coupler

L-57 (page 11, right lower column), L-68 (page 12, right lower column) and L-77 (page 13, right lower column) of JP-A-3-39737; A-4-63 (page 134), A-4-73 and A-4-75 (page 139) of EP 456257; M-4, M-6 (page 26) and M-7 (page 27) of EP 486965; M-45 in paragraph 0024 of JP-A-6-43611; M-1 in paragraph 0036 of JP-A-5-204106; M-22 in paragraph 0237 of JP-A-4-362631.

Cyan Coupler

CX-1, CX-3, CX-4, CX-5, CX-11, CX-12, CX-14 and CX-15 (pages 14 to 16) of JP-A-4-204843; C-7, C-10 (page 35), C-34, C-35 (page 37), (I-1) and (I-17) (pages 42 and 43) of JP-A-4-43345; couplers represented by formula (Ia) or (Ib) in claim 1 of JP-A-6-67385.

Polymer Coupler

P-1 and P-5 (page 11) of JP-A-2-44345.

As the coupler which provides a colored dye having an appropriate diffusibility, those described in U.S. Pat. No. 4,366,237, British Patent 2,125,570, EP-B-96873 and German Patent 3,234,533 are preferred.

As the coupler for correcting unnecessary absorption of a colored dye, yellow colored cyan couplers represented by formula (CI), (CII), (CIII) or (CIV) described at page 5 of EP-A-456257 (particularly, YC-86 at page 84); Yellow Colored Magenta Couplers ExM-7 (page 202), EX-1 (page 249) and EX-7 (page 251) described in EP-A-456257; Magenta Colored Cyan Couplers CC-9 (column 8) and CC-13 (column 10) described in U.S. Pat. No. 4,833,069; and colorless masking couplers represented by formula (2)

(column 8) of U.S. Pat. No. 4,837,136 and formula (A) in claim 1 of WO92/11575 (particularly, compounds described in pages 36 to 45) are preferred.

Compounds (including couplers) which release a photographically useful compound residue upon reaction with an oxidation product of a developing agent are described below.

Development Inhibitor-Releasing Compound

Compounds represented by formula (I), (II), (III) or (IV) described at page 11 of EP-A-378236 (particularly, T-101 (page 30), T-104 (page 31), T-113 (page 36), T-131 (page 45), T-144 (page 51) and T-158 (page 58)); compounds represented by formula (I) described at page 7 of EP-A-436938 (particularly, D-49 (page 51)); compounds represented by formula (1) of JP-A-5-307248 (particularly, (23) in paragraph 0027); and compounds represented by formula (I), (II) or (III) described at pages 5 and-6 of EP-A-440195 (particularly, I-(1) at page 29);

Bleaching Accelerator-Releasing Compound

Compounds represented by formula (I) or (I') at page 5 of EP-A-310125 (particularly (60) and (61) at page 61); and compounds represented by formula (I) in claim 1 of JP-A-6-59411 (particularly, (7) in paragraph 0022);

Ligand-Releasing Compound

Compounds represented by LIG-X described in claim 1 of U.S. Pat. No. 4,555,478 (particularly, compounds in column 12, lines 21 to 41);

Leuco Dye-Releasing Compound

Compounds 1 to 6 in columns 3 to 8 of U.S. Pat. No. 4,749,641;

Fluorescent Dye-Releasing Compound

Compounds represented by COUP-DYE in claim 1 of U.S. Pat. No. 4,774,181 (particularly, compounds 1 to 11 in columns 7 to 10);

Development Accelerator- or Fogaing Agent-Releasing Compound

Compounds represented by formula (1), (2) or (3) in column 3 of U.S. Pat. No. 4,656,123 (particularly (I-22) in column 25) and ExZK-2 at page 75, lines 36 to 38 of EP-A-450637;

Compound Which Releases Group Capable of Becoming Dye First When Released

Compounds represented by formula (I) in claim 1 of U.S. Pat. No. 4,857,447 (particularly, Y-1 to Y-19 in columns 25 to 36).

Preferred additives other than couplers are described below.

Dispersion Medium of Oil-Soluble Organic Compound

P-3, P-5, P-16, P-19, P-25, P-30, P-42, P-49, P-54, P-55, P-66, P-81, P-85, P-86 and P-93 of JP-A-62-215272 (pages 140 to 144);

Latex for Impregnation of Oil-Soluble Organic Compound

Latexes described in U.S. Pat. No. 4,199,363;

Developing Agent Oxidation Product Scavenger

Compounds represented by formula (I) in column 2, lines 54 to 62 of U.S. Pat. No. 4,978,606 (particularly, I-(1), I-(2), I-(6) and I-(12) (columns 4 to 5)) and compounds represented by any one of formulae in column 2, lines 5 to 10 of U.S. Pat. No. 4,923,787 (particularly, Compound 1 (column 3));

Stain Inhibitor

Compounds represented by formula (I), (II) or (III) at page 4, lines 30 to 33 of EP-A-298321 (particularly, I-47, I-72, III-1 and III-27 (pages 24 to 48));

Discoloration Inhibitor

A-6, A-7, A-20, A-21, A-23, A-24, A-25, A-26, A-30, A-37, A-40, A-42, A-48, A-63, A-90, A-92, A-94 and A-164 of EP-A-298321 (pages 69 to 118), II-1 to III-23 in columns 25 to 38 of U.S. Pat. No. 5,122,444 (particularly, III-10), I-1 to III-4 at pages 8 to 12 of EP-A-471347 (particularly, II-2) and A-1 to A-48 in columns 32 to 40 of U.S. Pat. No. 5,139,931 (particularly, A-39 and A-42);

Material Which Reduces Use Amount of Coloration Reinforcing Agent or Color Mixing Inhibitor I-1 to II-15 at pages 5 to 24 of EP-A-411324 (particularly, I-46);

Formalin Scavenger

SCV-1 to SCV-28 at pages 24 to 29 of EP-A-477932 (particularly SCV-8);

Hardening Agent

H-1, H-4, H-6, H-8 and H-14 at page 17 of JP-A-1-214845, compounds (H-1 to H-54) represented by any one of formulae (VII) to (XII) in columns 13 to 23 of U.S. Pat. No. 4,618,573, Compounds (H-1 to H-76) represented by formula (6) at page 8, right lower column of JP-A-2-214852 (particularly, H-14) and compounds described in claim 1 of U.S. Pat. No. 3,325,287;

Development Inhibitor Precursor

P-24, P-37 and P-39 of JP-A-62-168139 (pages 6 to 7) and compounds described in claim 1 of U.S. Pat. No. 5,019,492 (particularly, 28 and 29 in column 7);

Antiseptic, Antimold

I-1 to III-43 in columns 3 to 15 of U.S. Pat. No. 4,923,790 (particularly, II-1, II-9, II-10, II-18 and III-25);

Stabilizer, Antifoggant

I-1 to I-(14) in columns 6 to 16 of U.S. Pat. No. 4,923,793 (particularly, I-1, I-60, I-(2) and I-(13)) and compounds 1 to 65 in columns 25 to 32 of U.S. Pat. No. 4,952,483 (particularly, 36);

Chemical Sensitizer triphenylphosphine, selenide and compound 50 of JP-A-5-40324;

Dye a-1 to b-20 at pages 15 to 18 (particularly, a-1, a-12, a-18, a-27, a-35, a-36 and b-5) and V-1 to V-23 at pages 27 to 29 (particularly, V-1) of JP-A-3-156450, F-I-1 to F-II-43 at pages 33 to 55 of EP-A-445627 (particularly, F-I-11 and F-II-8), III-1 to III-36 at pages 17 to 28 (particularly, III-1 and III-3) of EP-A-457153, fine crystal dispersion products of Dye-1 to Dye-124 at pages 8 to 26 of WO88/04794, compounds 1 to 22 at pages 6 to 11 of EP-A-319999 (particularly, Compound 1), compounds D-1 to D-87 (pages 3 to 28) represented by formula (1), (2) or (3) of EP-A-519306, compounds 1 to 22 (columns 3 to 10) represented by formula (I) of U.S. Pat. No. 4,268,622 and compounds (1) to (31) (columns 2 to 9) represented by formula (I) of U.S. Pat. No. 4,923,788;

UV Absorbent

Compounds (18b) to (18r) and 101 to 427 (pages 6 to 9) represented by formula (1) of JP-A-46-3335, compounds (3) to (66) (pages 10 to 44) represented by formula (I) and compounds HBT-1 to HBT-10 (page 14) represented by formula (III) of EP-A-520938, and compounds (1) to (31) (columns 2 to 9) represented by formula (1) of EP-A-521823.

The present invention can be applied to various color photographic materials such as color negative film for general use or for movie, color reversal film for slide or for television, color paper, color positive film and color reversal paper. Further, the present invention is suitably used for a film unit with a lens described in JP-B-2-32615 and JP-B-U-3-39784 (the, term "JP-B-U" as used herein means an "examined Japanese utility model publication). Furthermore, The present invention can be applied to a diffusion transfer type color photograph using heat development, a diffusion transfer photograph using an autopositive emulsion or a wet reversal color copying material using an autopositive emulsion.

Examples of the support properly used in the present invention are described in RD No. 17643, page 28, ibid., No. 18716, from page 647, right column to page 648, left column and ibid., No. 307105, page 879.

In the photographic material of the present invention, the total thickness of all hydrophilic colloid layers on the side having emulsion layers is preferably 28 μm or less, more preferably 23 μm or less, still more preferably 18 μm or less and most preferably 16 μm or less. The film swelling speed $T_{1/2}$ is preferably 30 seconds or less, more preferably 20 seconds or less. $T_{1/2}$ is defined as the time required for the film thickness to reach a half (½) of a saturation film thickness which corresponds to 90% of the maximum swollen thickness achieved at the processing with a color developer at 30° C. for 3 minutes and 15 seconds. The film thickness means a film thickness determined at 25° C. and 55% RH (relative humidity) under humidity conditioning for 2 days. $T_{1/2}$ can be measured by means of a swellometer described in A. Green et al, *Photogr. Sci. Eng.*, Vol. 19, 2, pp. 124–129. The $T_{1/2}$ can be adjusted by adding a hardening agent to gelatin as a binder or changing the aging conditions after coating. The swelling rate is preferably from 150 to 400%. The swelling rate can be obtained from the maximum swollen film thickness under the above-described conditions according to the formula:

(maximum swollen film thickness–film thickness)/film thickness.

In the photographic material of the present invention, on the side opposite to the side having emulsion layers, a hydrophilic colloid layer (called back layer) having a total dry thickness of from 2 to 20 μm is preferably provided. This back-layer preferably contains a light absorbent, a filter dye, an ultraviolet absorbent, an antistatic agent, a hardening agent, a binder, a plasticizer, a lubricant, a coating agent or a surface active agent, which are described above. The back layer has a swelling rate of preferably from 150 to 500%.

The photographic material of the present invention can be developed according to usual methods described in RD No. 17643, pp. 28–29, ibid., No. 18716, p. 651, from left to right columns and ibid., No. 307105, pp. 880–881.

The color developer used in development of the photographic material of the present invention is preferably an alkaline aqueous solution comprising as a main component an aromatic primary amine color developing agent. As the color developing agent, an aminophenol-base compound may be useful but a p-phenylenediamine-base compound is preferably used and representative and preferred examples thereof include compounds described in EP-A-556700, page 28, lines 43 to 52. These compounds may be used in combination of two or more depending on the purpose.

The color developer usually contains a pH buffer such as a carbonate, a borate or a phosphate of an alkali metal, or a development inhibitor or an antifoggant such as a chloride salt, a bromide salt, an iodide salt, a benzimidazole, a benzothiazole or a mercapto compound. The color developer may also contain, if desired, a preservative such as hydroxylamine, diethylhydroxylamine, sulfite, hydrazines (e.g., N,N-biscarboxymethylhydrazine), phenylsemicarbazides, triethanolamine and catecholsulfonic acids; an organic solvent such as ethylene glycol and diethylene glycol; a development accelerator such as benzyl alcohol, polyethylene glycol, a quaternary ammonium salt and amines; a dye-forming coupler; a competing coupler; an auxiliary developing agent such as 1-phenyl-3-pyrazolidone; a tackifying agent; and various chelating agents including aminopolycarboxylic acid, aminopolyphosphonic acid, alkylphosphonic acid and phosphonocarboxylic acid, such as ethylenediaminetetraacetic acid, nitrilotriacetic acid, diethylenetriaminepentaacetic acid, cyclohexanediaminetetraacetic acid, hydroxyethyliminodiacetic acid, 1-hydroxyethylidene-1,1-diphosphonic acid, nitrilo-N,N,N-trimethylenephosphonic acid, ethylenediamine-N,N,N,N-tetramethylenephosphonic acid, ethylenediamine-di(o-hydroxyphenylacetic acid) and a salt thereof.

In carrying out reversal processing, the color development usually follows black-and-white development. The black-and-white developer uses known black-and-white developing agents such as dihydoxybenzenes (e.g., hydroquinone), 3-pyrazolidones (e.g., 1-phenyl-3-pyrazolidone) and aminophenols (e.g., N-methyl-p-aminophenols), individually or in combination. The color developer or the black-and-white developer usually has a pH of from 9 to 12. The replenishing amount of these developers is, although it may vary depending on the color photographic material to be processed, generally 3 l or less per in of the photographic material and when the bromide ion concentration of the replenisher is lowered, the replenishing amount may be reduced even to 500 ml or less. When the replenishing amount is reduced, the contact area of the processing tank with air is preferably reduced to prevent evaporation or air oxidation of the solution.

The processing effect resulting from contact of the photographic processing solution with air in a processing tank can be evaluated by an opening ratio (=[contact area of the processing solution with air (cm$^2$)]÷[volume of the processing solution (cm$^3$)]. The opening ratio as defined above is preferably 0.1 or less, more preferably from 0.001 to 0.05. The opening ratio can be reduced, for example, by providing a shielding material such as a floating lid on the surface of the photographic processing solution in the processing tank, by using a movable lid described in JP-A-1-82033 or by a slit development method described in JP-A-63-216050. The opening ratio is preferably reduced not only in the color development and black-and-white development but also in any subsequent step such as bleaching, bleach-fixing, fixing, water washing or stabilization. Further, by using a means for suppressing the accumulation of bromide ions in the developer, the replenishing amount can be reduced.

The color development time is usually set to from 2 to 5 minutes, however, further reduction in the processing time can be achieved by carrying out the processing at a high temperature and a high pH and by using a color developing agent in a high concentration.

After color development, the photographic emulsion layer is usually subjected to bleaching. The bleaching may be conducted at the same time with the fixing (bleach-fixing) or may be conducted separately. For the purpose of rapid processing, the bleaching may be followed by bleach-fixing. Further, a processing in a bleach-fixing bath consisting of two continuous tanks, a processing comprising fixing before bleach-fixing or a processing comprising bleaching after bleach-fixing may be freely selected depending upon the purpose. Examples of the bleaching agent include compounds of a polyvalent metal such as iron(III), peracids, quinones and nitro compounds. Representative examples of the bleaching agent include organic complex salts of iron (III), for example, complex salts with an aminopolycarboxylic acid such as ethylenediaminetetraacetic acid, diethylenetriaminepentaacetic acid, cyclohexanediaminetetraacetic acid, methyliminodiacetic acid, 1,3- diaminopropanetetraacetic acid or glycol ether diaminetetraacetic acid, and complex salts with citric acid, tartaric acid or malic acid. Among these, an aminopolycarboxylic acid ferrate complex salt including an ethylenediaminetetraacetato ferrate complex salt and 1,3-diaminopropanetetraacetato ferrate complex salt is preferred in view of rapid processing and prevention of environmental pollution. Further, the aminopolycarboxylic acid ferrate complex salt is particularly useful for the bleaching solution or for bleach-fixing solution. The bleaching solution or the bleach-fixing solution using the aminopolycarboxylic acid ferrate complex salt has a pH of generally from 4.0 to 8 but the processing may be carried out at a lower pH for expediting the processing.

A bleaching accelerator may be used, if desired, in the bleaching solution, the bleach-fixing solution or a prebath thereof. Specific examples of useful bleaching accelerators include compounds described in the following specifications: for example, compounds having a mercapto group or a disulfide group described in U.S. Pat. No. 3,893,858, German Patent Nos. 1,290,812 and 2,059,988, JP-A-53-32736, JP-A-53-57831, JP-A-53-37418, JP-A-53-72623, JP-A-53-95630, JP-A-53-95631, JP-A-53-104232, JP-A-53-124424, JP-A-53-141623, JP-A-53-28426 and RD No. 17129 (July, 1978); thiazolidine derivatives described in JP-A-50-140129; thiourea derivatives described in JP-B-45-8506, JP-A-52-20832, JP-A-53-32735 and U.S. Pat. No. 3,706,561; iodide salts described in German Patent 1,127,715 and JP-A-58-16235; polyoxyethylene compounds described in German Patent Nos. 966,410 and 2,748,430; polyamine compounds described in JP-B-45-8836; compounds described in JP-A-49-40943, JP-A-49-59644, JP-A-53-94927, JP-A-54-35727, JP-A-55-26506 and JP-A-58-163940; and bromide ion. Among these, compounds having a mercapto group or a disulfide group are preferred in view of a large acceleration effect and in particular, compounds described in U.S. Pat. No. 3,893,858, German Patent No. 1,290,812 and JP-A-53-95630 are preferred. Also, compounds described in U.S. Pat. No. 4,552,834 are preferred. The bleaching accelerator may be incorporated into the photographic material. The bleaching accelerator is particularly effective in bleach-fixing a color photographic material for photographing.

In addition to the above-described compounds, the bleaching solution or the bleach-fixing solution preferably contains an organic acid in order to prevent bleaching stains. A particularly preferred organic acid is compounds having an acid dissociation constant (pKa) of from 2 to 5 and specific examples thereof include acetic acid, propionic acid and hydroxyacetic acid.

Examples of the fixing agent for use in the fixing solution or the bleach-fixing solution include thiosulfates, thiocyanates, thioether-base compounds, thioureas and a large quantity of iodides. Among these, the thiosulfate is commonly used and an ammonium thiosulfate can be most widely used. Also, a combination use of a thiosulfate with a thiocyanate, a thioether-base compound or a thiourea is preferred. As the preservative for the fixing solution or the bleach-fixing solutions sulfites, bisulfites, carbonyl bisulfite adducts and sulfinic acid compounds described in EP-A-294769 are preferred. Further, the fixing solution or the bleach-fixing solution preferably contains various aminopolycarboxylic acids or organic phosphonic acids for the purpose of stabilization of the solution.

In the present invention, in order to adjust the pH, a compound having a pKa of from 6.0 to 9.0, preferably, an imidazole such as imidazole, 1-methylimidazole, 1-ethylimidazole and 2-methylimidazole is preferably added to the fixing solution or the bleach-fixing solution in an amount of from 0.1 to 10 mol/liter.

The total desilvering time is preferably as short as possible if desilvering failure is not caused. The time is preferably from 1 to 3 minutes, more preferably from 1 to 2 minutes. The processing temperature is from 25 to 50° C., preferably from 35 to 45° C. In this preferred temperature range, the desilvering rate is improved and the occurrence of stains after processing can be effectively prevented.

In the desilverization, the stirring is preferably intensified as highly as possible. Specific examples of the method for intensifying stirring include a method of colliding a jet stream of a processing solution against the emulsion surface of the photographic material described in JP-A-62-183460, a method of increasing the stirring effect using a rotary means described in JP-A-62-183461, a method of increasing the stirring effect by moving the photographic material while putting the emulsion surface into contact with a wire blade provided in the solution to cause turbulence on the emulsion surface, and a method of increasing the circulation flow rate of the entire processing solutions. Such a means for intensifying the stirring is effective in any of the bleaching solution, the bleach-fixing solution and the fixing solution. The intensification of stirring is considered to increase the supply rate of the bleaching agent or the fixing agent into the emulsion layer and as a result, to elevate the desilverization rate. The above-described means for intensifying stirring is more effective when a bleaching accelerator is used and in this case, the acceleration effect can be outstandingly increased or the fixing inhibitory action by the bleaching accelerator can be eliminated.

The automatic developing machine used for the photographic material of the present invention preferably has a transportation means of a photographic material described in JP-A-60-191257, JP-A-60-191258 and JP-A-60-191259. As described in JP-A-60-191257 above, the transportation means can achieve extreme decrease in the amount of a processing solution carried over from a previous bath to a post bath, provide a great effect in preventing the deterioration in capacity of the processing solution and be particularly effective in reducing the processing time or decreasing the replenishing amount of a processing solution in each step.

The photographic material of the present invention is generally subjected to water washing and/or stabilization after desilvering. The amount of water in water washing can be set over a wide range according to the characteristics (e.g., due to the material used such as a coupler) or the use of the a photographic material and in addition, the temperature of washing water, the number of water washing tanks (stage number), the replenishing system such as countercurrent and co-current or other various conditions. Among these, the relation between the number of water washing tanks and the amount of water in a multi-stage countercurrent system can be obtained according to the method described in *Journal of the Society of Motion Picture and Television Engineers*, Vol. 64, pp. 248–253 (May, 1955). According to the multi-stage countercurrent system described in the above-described publication, the amount of washing water may be greatly reduced but due to the increase in the residence time of water in the tank, a problem is caused such that bacteria proliferate and the floats generated adhere to the photographic material. In order to solve such a problem, a method of reducing calcium ions or magnesium ions described in JP-A-62-288838 can be very effectively used. Further, isothiazolone compounds and thiabendazoles described in JP-A-57-8542, chlorine-base bactericides such as sodium chlorinated isocyanurate, benzotriazoles and bactericides described in Hiroshi Horiguchi, *Bokin, Bobai-Zai no Kagaku*, Sankyo Shuppan (1986), *Biseibutsu no Mekkin, Sakkin, Bobai-Gijutsu* compiled by Eisei Gijutsu Kai, issued by Kogyo Gijutsu Kai (1982), and *Bokin-Bobai Zai Jiten* compiled by Nippon Bokin Bobai Gakkai (1986) can be also used.

The washing water in the processing of the photographic material of the present invention has a pH of from 4 to 9, preferably from 5 to 8. The temperature and the processing time of water washing may be set variously according to the characteristics and use of the photographic material, but they are commonly from 15 to 45° C. and from 20 seconds to 10 minutes, preferably from 25 to 40° C. and from 30 seconds to 5 minutes, respectively. The photographic material of the present invention can be processed directly with a stabilizing solution in place of the above-described water washing. In such a stabilization processing, any known methods described in JP-A-57-8543, JP-A-58-14834 and JP-A-60-220345 can be used.

In some cases, the stabilization processing may be further carried out after the above-described water washing. An example thereof is a stabilization bath containing a dye stabilizing agent and a surface active agent used as a final bath of a color photographic material for photographing. Examples of the dye stabilizing agent include aldehydes such as formalin and glutaraldehyde, N-methylol compounds and hexamethylenetetramine or aldehyde sulfite addition products.

This stabilization bath may also contain various chelating agents and antimolds.

The overflow solution accompanying the replenishing of the above-described washing water and/or stabilization solution can be re-used in other processing steps such as desilvering.

In the processing, for example, using an automatic developing machine, if the above-described respective processing solutions are concentrated due to evaporation, water is preferably added to correct the concentration.

A color developing agent may be incorporated into the photographic material of the present invention so as to simplify and expedite the processing. The color developing agent is preferably incorporated into the photographic material as a block compound thereof. Examples of the block compound include indoaniline compounds described in U.S. Pat. No. 3,342,597, Schiff base-type compounds described in U.S. Pat. No. 3,342,599, *Research Disclosure No.* 14850 and ibid., No. 15159, aldol compounds described in ibid., No. 13924, metal salt complexes described in U.S. Pat. No. 3,719,492 and urethane-based compounds described in JP-A-53-135628.

The photographic material of the present invention may contain, if desired, various 1-phenyl-3-pyrazolidones for the purpose of accelerating the color development. Typical examples of the compound are described in JP-A-56-64339, JP-A-57-144547 and JP-A-58-115438.

Each processing solution used for processing the photographic material of the present invention is used at a temperature of from 10 to 50° C. Usually, the temperature as a standard is from 33 to 38° C. but higher temperatures may be used to accelerate the processing to thereby shorten the processing time or on the contrary, lower temperatures may be used to achieve improved image quality or improved stability of the processing solution.

There is no particular restriction on various additives and development processing used when the present invention is applied to a black-and-white photographic material and, for example, those described in JP-A-2-68539, JP-A-5-11389 and JP-A-2-58041 can be preferably used, of which pertinent portions are described below.

1. Silver Halide Emulsion and Production Process Thereof
    JP-A-2-68539, from page 8, right lower column, line 6 from the bottom to page 10, right upper column, line 12
2. Chemical Sensitization Method
    JP-A-2-68539, page 10, from right upper column, line 13 to left lower column, line 16, and selenium sensitization method described in JP-A-5-11389
3. Antifoggant, Stabilizer
    JP-A-2-68539, from page 10, left lower column, line 17 to page 11, left upper column, line 7 and from page 3, left lower column, line 2 to page 4, left lower column
4. Spectral Sensitizing Dye
    JP-A-2-68539, from page 4, right lower column, line 4 to page 8, right lower column and JP-A-2-58041, page 12, from left lower column, line 8 to right lower column, line 19
5. Surface Active Agent, Antistatic Agent
    JP-A-2-68539, from page 11, left upper column, line 14 to page 12, left upper column, line 9 and JP-A-2-58041, from page 2, left lower column, line 14 to page 5, line 12.
6. Matting Agent, Plasticizer, Slipping Agent
    JP-A-2-68539, page 12, from left upper column, line 10 to right upper column, line 10 and JP-A-2-58041, from page 5, left lower column, line 13 to page 10, left lower column, line 3
7. Hydrophilic Colloid
    JP-A-2-68539, page 12, from right upper column, line 11 to left lower column, line 16
8. Hardening Agent
    JP-A-2-68539, from page 12, left lower column, line 17 to page 13 right upper column, line 6
9. Development Processing
    JP-A-2-68539, page 15, from left upper column, line 14 to left lower column, line 13

In addition to those described in the foregoing, the present invention can be applied to a diffusion transfer photograph, a so-called instantaneous photograph. Examples of the diffusion transfer photograph are described in JP-A-5-297544.

Further, the present invention can be used in a heat developable photographic material. The heat developable photographic material in which the present invention can be used may be one which forms a black-and-white image or one which forms a color image. Examples thereof include heat developable photographic materials described in JP-A-60-162251, JP-A-64-13546, JP-A-1-161236, U.S. Pat. Nos. 4,474,867, 4,478,927, 4,507,380, 4,500,626, 4,483,914, 4,783,396 and 4,740,445, JP-A-59-231539 and JP-A-60-2950.

Furthermore, the present invention can be used in a wet reversal color copying material using an autopositive emulsion. This material is described as Sample 101 in Example 1 of JP-A-3-152530 or as Sample 1 in JP-A-2-90145.

The silver halide photographic material for color diffusion transfer to which the present invention can be applied, is described below.

The photographic material for use in the present invention fundamentally comprises light-sensitive silver halide, binder and dye-donating compound (which sometimes acts also as a reducing agent) on a support. These components are added to the same layer in many cases, however, if they can remain in a reactive state, the components may be divided and added to separate layers. For example, when a colored dye-donating compound is made be present in the lower layer of a silver halide emulsion, the reduction in sensitivity can be prevented.

In order to obtain colors over a wide range within the chromaticity diagram using three primary colors of yellow, magenta and cyan, at least three silver halide emulsion layers having sensitivity in different spectral regions are used in combination. For example, a three-layer combination of a blue-sensitive layer, a green-sensitive layer and a red-sensitive layer, a combination of a green-sensitive layer, a red-sensitive layer and an infrared-sensitive layer, and a combination of a red-sensitive layer, a first infrared-sensitive layer and a second infrared-sensitive layer may be used. Respective light-sensitive layers may be arranged in various orders known for usual color photographic materials. Furthers each light-sensitive layer may be divided into two or more layers, if desired.

In the heat developable photographic material, various auxiliary layers such as a protective layer, an undercoat layer, an interlayer, a yellow filter layer, an antihalation layer and a back layer may be provided.

Fundamental Structure and Preparation Method of Silver Halide Grain

The silver halide which can be used in the present invention may be any of silver chloride, silver bromide, silver iodobromide, silver chlorobromide, silver iodochloride and silver chloroiodobromide, however, silver iodobromide, silver chloride, silver bromide and silver chlorobromide each having a silver iodide content of about 30 mol % or less are preferred.

The silver halide emulsion for use in the present invention may be either a surface latent image-type emulsion or an internal latent image-type emulsion. The internal latent image-type emulsion is used as a direct reversal emulsion in combination with a nucleating agent or a light fogging agent. A so-called multiple structure grain having different halogen compositions between the inside and the surface of a grain may also be used. Out of multiple structure grains, particularly those having a double structure are sometimes called a core/shell emulsion.

The silver halide for use in the present invention is preferably a multiple structure grain emulsion, more preferably a core/shell emulsion. However, the present invention is by no means limited thereto. The silver halide emulsion for use in the present invention is preferably a monodisperse emulsion and the coefficient of variation described in JP-A-3-110555 is preferably 20% or less, more preferably 16% or less, still more preferably 10% or less. However, the present invention is by no means limited to this monodisperse emulsion.

The silver halide grain to which the present invention can be applied is not particularly restricted on the average grain size, however, the average grain size is preferably from 0.1 to 2.2 μm, more preferably from 0.1 to 1.2 μm. The crystal habit of the silver halide grain may be any of cubic form, octahedral form, tabular form having a high aspect ratio and pebble like form. More preferred is a cubic emulsion. To say specifically, any of silver halide emulsions described in U.S. Pat. No. 4,500,626, column 50, and U.S. Pat. No. 4,628,021, Research Disclosure, No. 17029 (1978), and JP-A-62-25159 can be used.

During preparation of the silver halide emulsion of the present invention, a so-called desilvering process is preferably performed to remove salts in excess. The desilvering may be performed by a noodle water washing method where the desilvering is performed while gelling gelatin, or by a flocculation method using an inorganic salt comprising polyvalent anions (e.g., sodium sulfate), an anionic surface active agent, an anionic polymer (e.g., polystyrenesulfonic acid), or a gelatin derivative (e.g., aliphatic acylated gelatin, aromatic acylated gelatin, aromatic carbamoylated gelatin). Preferably, flocculation using a compound represented by Flocculant (a) or Flocculant (b) which will be described layer, is used, however, the present invention is by no means limited thereto. Further, ultrafiltration using no flocculant may be used. The removal of excessive salts may be omitted.

The silver halide emulsions for use in the present invention may contain heavy metals, such as iridium, rhodium, platinum, cadmium, zinc, thallium, lead, iron, and chromium, for various purposes. These compounds may be used individually or in combination of two or more of them. The addition amount varies depending on the purpose, however, in general, it is approximately from $10^{-9}$ to $10^{-3}$ mol per mol of silver halide. The compound may be incorporated uniformly into a grain or may be locally present in the inside or on the surface of a grain.

The addition amount of iridium for use in the present invention is preferably from $10^{-9}$ to $10^{-4}$ mol, more preferably from $10^{-8}$ to $10^{-6}$ mol, per mol of silver halide. In the case of a core/shell emulsion, the iridium may be added to the core and/or the shell. Preferred examples of the iridium compound include $K_2IrCl_6$ and $K_3IrCl_6$.

The addition amount of rhodium for use in the present invention is preferably from $10^{-9}$ to $10^{-6}$ mol per mol of silver halide. The addition amount of iron for use in the present invention is preferably from $10^{-7}$ to $10^{-3}$, more preferably from $10^{-6}$ to $10^{-3}$ mol, per mol of silver halide. A method where a part or whole of the above-described heavy metal is previously doped to a fine grain emulsion of silver chloride, silver chlorobromide, silver bromide or silver iodobromide and the fine grain emulsion is added to locally dope the metal onto the silver halide emulsion surface, is also preferably used. At the stage of forming silver halide grains, rhodanates, $NH_3$, 4-substituted thioether compounds represented by Compound (a) which will be described later, organic thioether derivatives described in JP-B-47-11386 or sulfur-containing compounds described in JP-A-53-144319 may be used as a silver halide solvent.

At the stage of forming silver halide grains, nitrogen-containing compounds described in JP-B-46-7781, JP-A-60-222842 and JP-A-60-122935 may be added.

Gelatin is advantageous as a protective colloid or as a binder of other hydrophilic colloids used in the preparation of emulsion of the present invention, however, a hydrophilic colloid other than gelatin can also be used. Examples thereof include proteins such as gelatin derivatives, graft polymers of gelatin to other polymer, albumin and casein; cellulose derivatives such as hydroxyethyl cellulose and cellulose sulfates; sodium arginates and starch derivatives; and various synthetic hydrophilic high polymer materials such as homopolymers and copolymers of polyvinyl alcohol, polyvinyl alcohol partial acetal, poly-N-vinylpyrrolidone, polyacrylic acid, polymethacrylic acid, polyacrylamido, polyvinyl imidazole and polyvinyl pyrazole.

The gelatin may be a lime-processed gelatin, an acid-processed gelatin or an enzyme-processed gelatin as described in Bull. Soc. Sci. Photo. Japan, No. 16, p. 30 (1966), and a hydrolysate of gelatin or an enzymolysate of gelatin can also be used.

With respect to other conditions, P. Glafkides, Chemie et Phisique Photographique, Paul Montel (1967), G. F. Duffin, Photographic Emulsion Chemistry, The Focal Press (1966), and V. L. Zelikman et al., Making and Coating Photographic

*Emulsion,* The Focal Press (1964) may be referred to. More specifically, any of an acid method, a neutral method and an ammonia method may be used, and as the system of reacting a soluble silver salt and a soluble halide, any of a single jet method, a double jet method and a combination of these may be used.

A method of forming grains in the presence of excessive silver ions (so-called reversed mixing method) may also be used. Further, as one system of a double jet method, a method of maintaining the pAg in the liquid phase where silver halide is formed constant, a so-called controlled double jet method, may also be used. To accelerate the growth of grains, the concentration, addition amount and addition rate of silver salts and halogen salts may be increased (as described in JP-A-55-142329, JP-A-55-158124, and U.S. Pat. No. 3,650,757). During grain formation or after grain formation, the silver halide grain surface may be substituted by a halogen of forming difficultly soluble silver halide grains.

The stirring of the reaction solution may be performed by any known stirring method. The temperature and pH of the reaction solution during formation of silver halide grains may be freely selected, however, the pH is preferably form 2.2 to 6.0, more preferably from 3.0 to 5.5.

The emulsion for a blue-sensitive layer used in the present invention is described in JP-A-5-119429. A silver halide emulsion comprising silver halide grains having a high silver iodide content layer on the grain surface and subjected to chemical sensitization before desilvering and addition of iodine ions is particularly preferred.

Addition Method of Sensitizing Dye

The sensitizing dye may be added basically at any time. More specifically, the sensitizing dye may be added at the beginning (may be added before nucleation) of, during or after formation of silver halide emulsion grains, at the beginning of, during or after completion of the desilvering, during redispersion of gelatin, before, during or after the chemical sensitization or at the preparation of coating solution. The sensitizing dye is preferably added during or after completion of the formation of silver halide grains, or before, during or after the chemical sensitization. The term "after the chemical sensitization" as used herein means that the sensitizing dye is added after all chemicals necessary for the chemical sensitization are added.

As described in U.S. Pat. No. 4,183,756, the sensitizing dye may be made present in the reaction system of a soluble silver salt (e.g., silver nitrate) with a halide (e.g., potassium bromide) before silver halide grains are generated. Further, as described in U.S. Pat. No. 4,225,666, the sensitizing dye may be made present in the above-described reaction system after the nucleation of silver halide grains and at the same time before completion of the silver halide grain formation. Furthermore, the sensitizing dye may be made present at the same time with the formation of silver halide-grains, namely, may be made present in the reaction solution at the same time with the mixing of a silver salt with a halide. The photographic material containing the thus-prepared emulsion is more excellent in the storability at high temperatures and in the gradation. The concentration of the solution added, the solvent, the addition time (either addition at once or addition over a time period), the temperature and the pH may be freely selected. Further, either liquid level addition or submerged addition may be used. These conditions are described in detail in JP-A-3-110555.

Kind of Sensitizing Dye

The dye for use in the emulsion used in the present invention includes cyanine dyes, merocyanine dyes, complex cyanine dyes, complex merocyanine dyes, holopolar cyanine dyes, hemicyanine dyes, styryl dyes and hemioxonol dyes. Specific examples thereof include sensitizing dyes described in U.S. Pat. No. 4,617,257, JP-A-59-180550, JP-A-60-140335 and *RD,* No. 17029, pp. 12–13 (1978). These sensitizing dyes may be used individually or in combination, and the combination of sensitizing dyes are often used for the purpose of supersensitization. Together with the sensitizing dye, a dye which itself has no spectral sensitization effect, or a compound which absorbs substantially no visible light, but exhibits supersensitization may be incorporated into the emulsion (e.g., those described in U.S. Pat. No. 3,615,641, JP-A-63-23145).

In the present invention, the entire amount of sensitizing dye may be added at once or the sensitizing dye may be added by several installments even if any of the above-described methods may be used. Further, the sensitizing dye may be added as a mixture with a soluble silver salt and/or a halide.

The sensitizing dye may be added after dissolving it in an organic solvent having compatibility with water, such as methanol, ethanol, propanol, fluorinated alcohol, methyl cellosolve, dimethylformamido and acetone, or in water (which may be either alkaline or acidic). Further, two or more of those described above may be used in combination. Furthermore, the sensitizing dye may be added in the form of a dispersion in a water/gelatin dispersion system or of a freeze-dried powder. Still further, the sensitizing dye may be added as a powder or solution where the dye is dispersed using a surface active agent. Examples of the sensitizing dye for use in the emulsion according to the present invention also include those described in JP-A-3-296745 and JP-A-4-31854. The use amount of the sensitizing dye is suitably from 0.001 to 20 g, preferably from 0.01 to 2 g, per 100 g of silver used in preparation of the emulsion.

Chemical Sensitization

The silver halide emulsion for use in the present invention may be used in the state of being not chemically sensitized, however, it is preferably subjected to chemical sensitization to increase sensitivity. The chemical sensitization may be performed using any of sulfur sensitization, gold sensitization, reduction sensitization and a combination of these.

In addition, chemical sensitization using a compound containing a chalcogen element other than sulfur, such as selenium or tellurium, or chemical sensitization using a noble metal such as palladium or iridium, may also be performed in combination with the above-described chemical sensitization.

Further, a method of using an inhibitor such as a nitrogen-containing heterocyclic compound including 4-hydroxy-6-methyl(1,3,3a,7)tetraazaindene may also be preferably used. The addition amount is preferably from $10^{-5}$ to $10^{-1}$ mol per mol of silver halide.

The pH at the time of chemical sensitization is preferably from 5.3 to 10.5, more preferably from 5.5 to 9.5.

The sulfur sensitizer is a compound containing sulfur capable of reacting with active gelatin or silver. Examples thereof include thiosulfate, allylthiocarbamido, thiourea, allylisothiacyanate, cystine, p-toluenethiosulfonic acid, rhodanine and mercapto compounds. In addition, those described in U.S. Pat. Nos. 1,574,944, 2,410,689, 2,278,947, 2,728,668 and 3,656,955 may also be used.

The coating amount of the light-sensitive silver halide used in the present invention is from 1 mg/m$^2$ to 10 g/m$^2$ as calculated in terms of silver.

The silver halide emulsion may be used in the state of being not post-ripened, however, it is usually subjected to chemical sensitization before use. Sulfur sensitization, reduction sensitization, noble metal sensitization and selenium sensitization, which are known for the emulsion used in normal photographic materials, may be used individually or in combination. The chemical sensitization may also be performed in the presence of a nitrogen-containing heterocyclic compound (JP-A-62-253159).

When the present invention is applied to a heat developable photographic material, an organic metal salt may be used as an oxidizing agent in combination with the light-sensitive silver halide. Among the organic metal salts, an organic silver salt is particularly preferably used.

The organic compound which can be used in forming the above-described organic silver salt oxidizing agent, include benzotriazoles described in U.S. Pat. No. 4,500,626, columns 52 to 53, fatty acids and other compounds. Further, silver salts of carboxylic acid having an alkynyl group such as silver phenylpropiolate described in JP-A-60-113235 and silver acetylide described in JP-A-61-249044 are useful. The organic silver salts may be used in combination of two or more thereof.

The organic silver salt is used in an amount of from 0.01 to 10 mol, preferably from 0.01 to 1 mol, per mol of light-sensitive silver halide. The coating amount in total of the light-sensitive silver halide and the organic silver salt is suitably from 50 mg/m$^2$ to 10 g/m$^2$ as calculated in terms of silver.

In the present invention various antifoggants and photographic stabilizers may be used. Examples thereof include azoles and azaindenes described in RD, No. 17643, pp. 24–25 (1978), nitrogen-containing carboxylic acids and phosphoric acids described in JP-A-59-168442, mercapto compounds and metal salts thereof described in JP-A-59-111636, and acetylene compounds described in JP-A-62-87957.

The binder in constituent layers of a photographic material or a dye-fixing element is preferably hydrophilic. Examples thereof include those described in JP-A-62-253159, pages (26) to (28). More specifically, transparent or translucent hydrophilic binders are preferred and examples thereof include natural compounds such as proteins (e.g., gelatin, gelatin derivatives) and polysaccharides (e.g., cellulose derivatives, starch, gum arabic, dextran, pullulane); and synthetic high polymer compounds such as polyvinyl alcohol, polyvinyl pyrrolidone and acrylamido polymers. Further, highly water-absorbing polymers described in JP-A-62-245260, namely, homopolymers of vinyl monomers having —COOM or —SO$_3$M (wherein M is a hydrogen atom or an alkali metal), or copolymers of the vinyl monomers or of the vinyl monomer with other vinyl monomer (for example, sodium methacrylate, ammonium methacrylate, Sumikagel L-5H produced by Sumitomo Chemical Company Limited), may also be used. The above-described binders may be used in combination of two or more thereof.

When a system of performing heat development while supplying a slight amount of water is used, water can be absorbed rapidly by using the above-described highly water-absorbing polymer. Further, when the highly water-absorbing polymer is used in a dye-fixing layer or a protective layer thereof, the re-transfer of the transferred dye from the dye-fixing element to other members can be prevented.

In the present invention, the coating amount of the binder is preferably 20 g/m$^2$ or less, more preferably 10 g/m$^2$ or less, and still more preferably 7 g/m$^2$ or less.

The constituent layer (including a back layer) of the photographic material or the dye-fixing element may contain various polymer latexes for the purpose of improving physical properties of the layer such as dimensional stabilization or prevention of curling, adhesion, cracking of layers or reduction/increase in sensitivity due to pressure. Specific examples of the polymer latex include those described in JP-A-62-245258, JP-A-62-136648 and JP-A-62-110066. In particular, a polymer latex having a low glass transition point (40° C. or lower) is used in a mordant layer, cracking of the mordant layer can be prevented, whereas when a polymer latex having a high glass transition point is used in a back layer, a curl-preventing effect can be provided.

The reducing agent for use in the present invention may be one known in the field of photographic materials. The reducing agent also includes the dye-donating compounds having a reducing property which will be described later (in this case, other reducing agent can be used in combination). Further, a reducing agent block compound which itself has no reducing property but shows the reducing property upon having action of a nucleophilic reagent or heat during the development, may also be used.

Examples of the reducing agent for use in the present invention include reducing agents and reducing agent block compounds as described in U.S. Pat. No. 4,500,626 (columns 49 and 50), U.S. Pat. No. 4,483,914 (columns 30 and 31), U.S. Pat. Nos. 4,330,617 and 4,590,152, JP-A-60-140335 (pages (17) and (18)), JP-A-57-40245, JP-A-56-138736, JP-A-59-178458, JP-A-59-53831, JP-A-59-182449, JP-A-59-182450, JP-A-60-119555, JP-A-60-128436 through JP-A-60-128439, JP-A-60-198540, JP-A-60-181742, JP-A-61-259253, JP-A-62-244044, JP-A-62-131253 through JP-A-62-131256, and EP-A-220746 (pages 78 to 96).

Combinations of various reducing agents described in U.S. Pat. No. 3,039,869 can also be used.

When a non-diffusible reducing agent is used, an electron-transferring agent and/or an electron-transferring agent block compound may be used in combination, if desired, so as to accelerate the movement of electrons between the non-diffusible reducing agent and the developable silver halide.

The electron-transferring agent or a block compound thereof may be selected from the above-described reducing agents and block compounds thereof. The electron-transferring agent or the block compound thereof preferably has mobility larger than that of the non-diffusible reducing agent (electron-donor). Particularly useful electron-transferring agents are 1-phenyl-3-pyrazolidones and aminophenols.

The non-diffusible reducing agent (electron-donor) for use in combination with the electron-transferring agent may be selected from the above-described reducing agents as long as it does not substantially move between layers of the photographic material. Preferred examples thereof include hydroquinones, sulfonamidophenols, sulfonamidonaphthols, compounds described as the electron-donor in JP-A-53-110827, and non-diffusible dye-donating compounds having a reducing property which will be described later.

The addition amount of the reducing agent is from 0.01 to 20 mol, preferably from 0.1 to 10 mol, per mol of silver.

In the present invention, the photographic material contains a compound which forms or releases a mobile dye in correspondence or counter-correspondence to the reaction of reducing silver ions to silver under high temperature conditions, namely, a dye-donating compound.

The dye-donating compound which can be used in the present invention is represented by formula (LI):

$$(\text{Dye-G})_q\text{—Y} \qquad (\text{LI})$$

wherein Dye is a dye group, a dye group temporarily shifted to short wave or a dye precursor group, q represents a positive integer, G represents a mere bond or a divalent linking group, and Y represents a group capable of cleaving the Y—G bond in correspondence or counter-correspondence with the development of silver halide and causing difference in the diffusibility between the compound represented by Dye-G and the compound represented by $(\text{Dye-G})_q$—Y.

The hydrophobic additives such as dye-donating compounds and non-diffusible reducing agents may be incorporated into layers of the photographic material according to known methods described, for example, in U.S. Pat. No. 2,322,027. In this case, a high boiling point organic solvent as described in JP-A-59-83154, JP-A-59-178451, JP-A-59-178452, JP-A-59-178453, JP-A-59-178454, JP-A-59-178455 and JP-A-59-178457 may be used, if desired, in combination with a low boiling point organic solvent having a boiling point of from 50 to 160° C.

The use amount of the high boiling point organic solvent is 10 g or less, preferably 5 g or less, per g of the dye-donating compound. Or, it is 1 ml or less, preferably 0.5 ml or less, more preferably 0.3 ml or less, per g of the binder.

A dispersion method using a polymer material described in JP-B-51-39853 and JP-A-51-59943 can also be used.

In the case of a substantially water-insoluble compound, a method of forming the compound into fine particles and then dispersing and incorporating them into the binder may be used, other than the above-described method.

In dispersing a hydrophobic compound in a hydrophilic colloid, various surface active agents may be used. Examples thereof include those described as the surface active agent in JP-A-59-157636, pages (37) to (38).

In the present invention, the photographic material may use a compound capable of achieving activation of development and at the same time, stabilization of an image. Preferred specific examples thereof include those described in U.S. Pat. No. 4,500,626, columns 51 and 52.

The photographic material may contain a non-diffusible filter dye for the purpose of improving sharpness. If desired, a filter dye having absorption in an infrared region may also be used. These filter dyes are described in detail in JP-A-4-31854, JP-A-4-217243, JP-A-4-276744 and JP-A-5-45834.

In a system of forming an image by the diffusion transfer of a dye, a dye-fixing element is used in combination with the photographic material. The dye-fixing element and the photographic material may be independently provided on separate supports or may be provided on the same support. With respect to the relationship of the photographic material with the dye-fixing element, the relationship with the support, the relationship with the white reflecting layer, the relationship described in U.S. Pat. No. 4,500,626, column 57, can also be applied to the present invention.

The dye-fixing element which is preferably used in the present invention has at least one layer containing a mordant and a binder. The mordant may be one known in the photographic field. Specific examples thereof include mordants described in U.S. Pat. No. 4,500,626 (columns 58 and 59) and JP-A-61-88256 (pages (32) to (41)), and those described in JP-A-62-244043 and JP-A-62-244036. Further, dye-accepting high polymer compounds described in U.S. Pat. No. 4,463,079 may also be used.

In the dye-fixing element, if desired, auxiliary layers such as a protective layer, a peeling-off layer or a curling-preventive layer may be provided. It is particularly advantageous to provide a protective layer.

The constituent layers of the photographic material or the dye-fixing element may contain a plasticizer, a slipping agent or a high boiling point organic solvent as an improver of releasability between the photographic material and the dye-fixing element. Specific examples thereof include those described in JP-A-62-253159 (page (25)) and JP-A-62-245253. Further, in order to achieve the above-described purpose, various silicone oils (including all silicone oils of from dimethyl silicone oil to modified silicone oils resulting from introducing various organic groups into dimethylsiloxane) may be used. Examples thereof include various modified silicone oils described in *Modified Silicone Oils* (*Technical Data P6-18B*), issued by Shin-Etsu Silicone KK. In particular, a carboxy-modified silicone (trade name: X-22-3710) is effective. Further, silicone oils described in JP-A-62-215953 and JP-A-63-46449 are also effective.

The photographic material and the dye-fixing element may use a discoloration inhibitor. Examples of the discoloration inhibitor include antioxidants, ultraviolet absorbents and certain kinds of metal complexes.

Examples of the antioxidant include chroman-base compound, coumarane-base compounds, phenol-base compounds (e.g., hindered phenols), hydroquinone derivatives, hindered amine derivatives and spiroindane-base compounds. Also, the compounds described in JP-A-61-159644 are effective.

Examples of the ultraviolet absorbent include benzotriazole-base compounds (described, for example, in U.S. Pat. No. 3,533,794), 4-thiazolidone-base compounds (described, for example,. in U.S. Pat. No. 3,352,681), benzophenone-base compounds (described, for -example, in JP-A-46-2784) and compounds described in JP-A-54-48535, JP-A-62-136641 and JP-A-61-88256. Also, ultraviolet absorbing polymers described in JP-A-62-260152 are effective.

Examples of the metal complex include compounds described in U.S. Pat. Nos. 4,241,155, 4,245,018 (columns 3 to 36) and U.S. Pat. No. 4,254,195 (columns 3 to 8), JP-A-62-174741, JP-A-61 -88256 (pages (27) to (29)), JP-A-63-199248, JP-A-1-75568 and JP-A-1-74272.

Examples of useful discoloration inhibitors are described in JP-A-62-215272 (pages (125) to (137)).

The discoloration inhibitor which inhibits discoloration of a dye transferred onto the dye-fixing element, may be previously incorporated into the dye-fixing element or may be supplied to the dye-fixing element from the external, for example, from the photographic material.

The above-described antioxidants, ultraviolet absorbents and metal complexes may be used in combination of these.

The photographic material or the dye-fixing element may use a fluorescent brightening agent. It is particularly preferred to incorporate the fluorescent brightening agent into the dye-fixing element or to supply it from the external, for example, from the photographic material. Examples of the fluorescent brightening agent include the compounds described in K. Veenkataraman (compiler), *The Chemistry of Synthetic Dyes,* Vol. V, Chap. 8, and JP-A-61-143752. Specific examples thereof include stilbene-base compounds, coumarin-base compounds, biphenyl-base compounds, benzoxazolyl-base compounds, naphthalimido-base compounds, pyrazoline-base compounds and carbostyryl-base compounds. The fluorescent brightening agent can be used in combination with the discoloration inhibitor.

The hardening agent for use in the constituent layers of the photographic material or the dye-fixing element includes hardening agents described in U.S. Pat. No. 4,678,739 (column 41), JP-A-59-116655, JP-A-62-245261 and JP-A-61-18942. Specific examples thereof include aldehyde-base hardening agents (e.g., formaldehyde), aziridine-base hardening agents, epoxy-base hardening agents, vinylsulfone-base hardening agents (e.g., N,N'-ethylenebis(vinylsulfonylacetamido)ethane), N-methylol-base hardening agents (e.g., dimethylolurea) and high polymer hardening agents (e.g., compounds described in JP-A-62-234157).

The constituent layers of the photographic material or the dye-fixing element may use various surface active agents as a coating aid or for the purpose of improving releasability or slipperiness, of preventing electrification or of accelerating development. Specific examples of the surface active agent are described in JP-A-62-173463 and JP-A-62-183457.

The constituent layers of the photographic material or the dye-fixing element may use various organic fluoro compounds for improving slipperiness,- preventing electrification or improving releasability. Representative examples of the organic fluoro compound include fluorine-base surface active agents described in JP-B-57-9053 (columns 8 to 17), JP-A-61 -20944 and JP-A-62-135826, and hydrophobic fluorine compounds such as oily fluorine-base compounds (e.g., fluorine-contained oil) and solid fluorine compound resins (e.g., ethylene tetrafluoride resin).

The photographic material and the dye-fixing element may use a matting agent. Examples of the matting agent include the compounds described in JP-A-61-88256 (page (29)) such as silicon dioxide, polyolefin and polymethacrylate, and the compounds described in JP-A-63-274944 and JP-A-63-274952 such as benzoguanamine resin beads, polycarbonate resin beads and AS resin beads. The matting agent may be used not only for preventing adhesion, controlling slipperiness or inhibiting Newton's ring but also for non-glossing the surface (image surface) of the dye-fixing element.

The constituent layers of the photographic material or the dye-fixing element may contain a heat solvent, a defoaming agent, an antiseptic/bactericide or colloidal silica. Specific examples of these additives are described in JP-A-61-88256 (pages (26) to (32)).

The photographic material or the dye-fixing element may use an image formation accelerator. The image formation accelerator has a function of accelerating the redox reaction of a silver salt oxidizing agent with a reducing agent, a function of accelerating the reaction such as production or decomposition of a dye from a dye-donating substance or release of a diffusible dye, and a function of accelerating the movement of a dye from the photographic material layer to the dye-fixing layer. In view of physicochemical functions, the accelerator is classified into bases or base block compounds, nucleophilic compounds, high boiling point organic solvents (oil), heat solvents, surface active agents and compounds having interaction with silver or silver ion. However, each group of these substances usually has composite functions and always shows several acceleration effects at the same time. These substances are described in detail in U.S. Pat. No. 4,678,739 (columns 38 to 40).

The base block compound includes salts of an organic acid which is decarboxylated upon heating, with a base, and compounds which releases amines by intramolecular nucleophilic substitution reaction, Lossen rearrangement or Beckmann rearrangement. Specific examples thereof are described in U.S. Pat. No. 4,511,493 and JP-A-62-65038.

In a system where heat development and transfer of a dye are performed simultaneously in the presence of a slight amount of water, the base and/or the base block compound is preferably incorporated into the dye-fixing element because the storability of the photographic material can be increased.

Further, combination of a difficultly soluble metal compound with a compound (called complex-forming compound) capable of complex-forming reaction with the metal ions constituting the difficultly soluble metal compound described EP-A-210660 and U.S. Pat. No. 4,740,445, and compounds which generates a base upon electrolysis described in JP-A-61-232451 may also be used as the base block compound. Particularly, the former method is effective. It is advantageous to add the difficultly soluble metal compound and the complex-forming compound separately to the photographic material and to the dye-fixing element.

In the present invention, the photographic material and/or dye-fixing element may use various development stopping agents for the purpose of always obtaining a constant image against fluctuations in the processing temperature and in the processing time during development.

The term "development stopping agent" as used herein means a compound which smoothly neutralizes or reacts with the base after proper development to reduce the concentration of the base in the layer to thereby stop the development or a compound which interacts with silver and silver salt to inhibit the development. More specifically, the development stopping agent includes acid block compounds which release an acid upon heating, electrophilic compounds which cause substitution reaction with the base present together upon heating, nitrogen-containing heterocyclic compounds, mercapto compounds and precursors thereof. The development stopping agent is described in more detail in JP-A-62-253159 (pages (31) and (32)).

In the present invention, as the support of the photographic material or the dye-fixing element, substances endurable to the processing temperature are used. In general, paper and synthetic high polymers (film) are used. Specific examples thereof include polyethylene terephthalate, polycarbonate, polyvinyl chloride, polystyrene, polypropylene, polyimido, celluloses (e.g., triacetyl cellulose) or those obtained by incorporating a pigment such as titanium oxide into these films, film synthetic paper made from polypropylene, mixed paper prepared from a synthetic resin pulp such as polyethylene with a natural pulp, Yankee paper, baryta paper, coated paper (particularly, cast coated paper), metal, cloths and glasses.

These materials each may be used alone or may be used as a support having laminated on one surface or both surfaces thereof with a synthetic high polymer such as polyethylene.

In addition, the supports described in JP-A-62-253159 (pages (29) to (31)) may be used.

On the surface of the above-described support, a hydrophilic binder and a semiconductor metal oxide such as alumina sol or tin oxide, or an antistatic agent such as carbon black may be coated.

The method of exposing and recording an image on the photographic material includes a method of exposing image information with light emitting diode or various lasers emitted through electrical signals, and a method of outputting image information on an image display such as a CRT, a liquid crystal display, an electroluminescense display or a plasma display and exposing it directly or through an optical system. More specifically, the exposure methods described in JP-A-2-129625, JP-A-5-176144, JP-A-5-199372 and JP-A-6-127021 may be used.

As the light source for use in recording an image on a photographic material, light emitting diode, lasers, CRT and other light sources described in U.S. Pat. No. 4,500,626 (column 56) may be used.

The magnetic recording layer which is preferably used in the present invention is described below.

The magnetic recording layer is provided by coating an aqueous or organic solvent-base coating solution containing a binder having dispersed therein magnetic particles, on a support.

The magnetic particle includes ferromagnetic iron oxide (e.g., $\gamma Fe_2O_3$), Co-doped $\gamma Fe_2O_3$, Co-doped magnetite, Co-containing magnetite, ferromagnetic chromium dioxide, ferromagnetic metal, ferromagnetic alloy, hexagonal Ba ferrite, Sr ferrite, Pb ferrite and Ca ferrite. Among these, Co-doped ferromagnetic iron oxide such as Co-doped $\gamma Fe_2O_3$ is preferred. The form of the magnetic particle may be any of acicular, rice grain-like, spherical, cubic and platy forms. The specific surface area as $S_{BET}$ is preferably 20 $m^2/g$ or more, more preferably 30 $m^2/g$ or more. The saturation magnetization ($\sigma s$) of the ferromagnetic material is preferably from $3.0 \times 10^4$ to $3.0 \times 10^5$ A/m, more preferably from $4.0 \times 10^4$ to $2.5 \times 10^5$ A/m. The ferromagnetic particle may be subjected to surface treatment with silica and/or alumina or an organic material. Further, the ferromagnetic particle may be subjected to surface-treatment with a silane coupling agent or a titanium coupling agent as described in JP-A-6-161032. Also, a magnetic particle having coated on the surface thereof an inorganic or organic material described in JP-A-4-259911 and JP-A-5-81652 may be used.

The binder for use in the magnetic particle includes a thermoplastic resin, a thermosetting resin, a radiation-curable resin, a reactive resin, an acid, alkali or biodegradable polymer, a natural polymer (e.g., cellulose derivative, saccharide derivative) and a mixture of these described in JP-A-4-219569. The above-described resin has a Tg of from −40° C. to 300° C. and a weight average molecular weight of from 2,000 to 1,000,000. Examples of the resin include a vinyl copolymer, a cellulose derivative such as cellulose diacetate, cellulose triacetate, cellulose acetate propionate, cellulose acetate butyrate and cellulose tripropionate, an acrylic resin and a polyvinyl acetal resin, and gelatin is also preferably used. Among these, cellulose di(tri)acetate is preferred. The binder may cured by adding thereto an epoxy-base, aziridine-base or isocyanate-base crosslinking agent. Examples of the isocyanate-base crosslinking agent include isocyanates such as tolylenediisocyanate, 4,4'-diphenylmethanediisocyanate, hexamethylenediisocyanate and xylylenediisocyanate, a reaction product of these isocyanates with polyalcohol (e.g., a reaction product of 3 mol of tolylenediisocyanate with 1 mol of trimethylolpropane) and a polyisocyanate produced by the condensation of these isocyanates, which are described, for example, in JP-A-6-59357.

The ferromagnetic material is dispersed into the binder by the method preferably using a kneader, a pin-type mill or an annular-type mill as described in JP-A-6-35092 and these may also be preferably used in combination. The dispersant described in JP-A-5-088283 and other known dipersants may be used. The thickness of the magnetic recording layer is from 0.1 to 10 μm, preferably from 0.2 to 5 μm, more preferably from 0.3 to 3 μm. The weight ratio of the magnetic particle to the binder is preferably from 0.5:100 to 60:100, more preferably from 1:100 to 30:100. The coating amount of magnetic particles is from 0.005 to 3 $g/m^2$, preferably from 0.01 to 2 $g/m^2$, more preferably from 0.02 to 0.5 $g/m^2$. The magnetic recording layer has a transmitted yellow density of preferably from 0.01 to 0.50, more preferably from 0.03 to 0.20, still more preferably from 0.04 to 0.15. The magnetic recording layer may be provided throughout the entire surface of or stripedly on the back surface of the photographic support by coating or printing. The magnetic recording layer can be coated by using air doctor, blade, air knife, squeeze, soakage, reverse roller, transfer roller, gravure, kiss, cast, spray, dip, bar or extrusion, and the coating solution described in JP-A-5-341436 is preferred.

The magnetic recording layer may be designed to have additional functions such as improvement of lubricity, control of curl, electrostatic charge prevention, prevention of adhesion or head abrasion, or other functional layers may be provided to undertake these functions. At least one or more of particles is preferably an abrasive as an aspheric inorganic particle having a Mhos' hardness of 5 or more. The composition of the aspheric inorganic particle is preferably an oxide such as aluminum oxide, chromium oxide, silicon dioxide or titanium dioxide, a carbide such as silicon carbide or titanium carbide, or a fine particle of diamond. The abrasive may be subjected to surface treatment with a silane coupling agent or a titanium coupling agent. The particles may be added to a magnetic recording layer or may be overcoated on the magnetic recording layer (for example, as a protective layer or a lubricant layer). The binder used here may be those described above and it is preferably the same as the binder in the magnetic recording layer. The photographic material having a magnetic recording layer is described in U.S. Pat. Nos. 5,336,589, 5,250,404, 5,229,259 and 5,215,874 and European Patent 466130.

The polyester support which is preferably used in the present invention is described below. The details thereon including the photographic material, the processing, the cartridge and the experimental examples are described in *JIII Journal of Technical Disclosure* No. 94-6023 (Mar. 15, 1994). The polyester is essentially constituted by a diol and an aromatic dicarboxylic acid. Examples of the aromatic dicarboxylic acid include 2,6-naphthalenedicarboxylic acid, 1,5-naphthalenedicarboxylic acid, 1,4-naphthalenedicarboxylic acid. 2,7-naphthalenedicarboxylic acid, terephthalic acid, isophthalic acid and phthalic acid, and examples of the diol include diethylene glycol, triethylene glycol, cyclohexanedimethanol, bisphenol A and biphenol. The polymer polymerized from these includes homopolymers such as polyethylene terephthalate, polyethylene naphthalate and polycyclohexanedimethanol terephthalate. Among these, preferred is a polyester containing from 50 to 100 mol % of 2,6-naphthalenedicarboxylic acid. Particularly preferred is polyethylene 2,6-naphthalate. The average molecular weight is approximately from 5,000 to 200,000. The polyester for use in the present invention has a Tg of 50° C. or higher, more preferably 90° C. or higher.

The polyester support is then subjected to heat treatment to refuse to have curling habit at a heat treatment temperature of from 40° C. to less than Tg, more preferably from (Tg−20° C.) to less than Tg. The heat treatment may be conducted either at a constant temperature within the above-described range or while cooling. The heat treatment time is from 0.1 to 1,500 hours, more preferably from 0.5 to 200 hours. The support may be subjected to heat treatment either in a state of roll or as a web along the conveyance. The surface may be made uneven (for example, by coating electrically conductive inorganic fine particles such as $SnO_2$ or $Sb_2O_5$)) to improve the surface state. Also, it is preferred to make some designs such that the edge is knurled to slightly increase the height only of the edge, thereby preventing the difference in level due to the edge from imparting the evenness of support wound thereon. The heat treatment may be conducted at any stage of after formation of support film, after surface treatment, after coating of a back layer (e.g., antistatic agent, slipping agent) and after coating of an undercoat layer. The preferred stage is after coating of an antistatic agent.

Into the polyester, an ultraviolet absorbent may be kneaded in. Or, for preventing light piping, a commercially available dye or pigment for polyester, such as Diaresin produced by Mitsubishi Kasei Corporation or Kayaset produced by Nippon Kayaku K.K., may be mixed so as to attain the purpose.

The surface treatment is preferably conducted so that the support can be bonded to the photographic material constituent layer. Examples of the surface activation treatment include chemical treatment, mechanical treatment, corona discharge treatment, flame treatment, ultraviolet light treatment, high frequency treatment, glow discharge treatment, active plasma treatment, laser treatment, mixed acid treatment and ozone oxidation treatment. Among these surface treatments, preferred are ultraviolet irradiation treatment, flame treatment, corona treatment and glow treatment.

The undercoating method is described below. The undercoating may be single layer coating or two or more layer coating. The binder for the undercoat layer includes a copolymer starting from a monomer selected from vinyl chloride, vinylidene chloride, butadiene, methacrylic acid, acrylic acid, itaconic acid and maleic anhydride, and in addition, polyethyleneimine, epoxy resin, grafted gelatin, nitrocellulose and gelatin. The compound which expands the support include resorcin and p-chlorophenol. The undercoat layer may contain a gelatin hardening agent and examples thereof include chromic salts (e.g., chrome alum), aldehydes (e.g., formaldehyde, glutaraldehyde), isocyanates, active halogen compounds (e.g., 2,4-dichloro-6-hydroxy-S-triazine), epichlorohydrin resin and active vinyl sulfone compounds. Further, the undercoat layer may contain an inorganic fine particle such as $SiO_2$ or $TiO_2$, or a polymethyl methacrylate copolymer fine particle (0.01 to 10 $\mu$m), as a matting agent.

The antistatic agent which is preferably used in the present invention includes high polymers containing a carboxylic acid, a carboxylate or a sulfonate, cationic high polymers and ionic surface active agent compounds.

Most preferred antistatic agents are fine particles of at least one crystalline metal oxide having a volume resistivity of $10^7$ $\Omega$·cm or less, more preferably $10^5$ $\Omega$·cm or less and a particle size of from 0.001 to 1.0 $\mu$m, selected from ZnO, $TiO_2$, $SnO_2$, $Al_2O_3$, $In_2O_3$, $SiO_2$, MgO, BaO, $MoO_3$ and $V_2O_5$, or of a composite oxide of these (e.g., Sb, P, B, In, S, Si, C), and fine particles of a sol-like metal oxide or of a composite oxide of these. The content of the antistatic agent in the photographic material is preferably from 5 to 500 mg/m$^2$, more preferably from 10 to 350 mg/m$^2$. The ratio of the electrically conductive crystalline oxide or a composite oxide thereof to the binder is preferably from 1/300 to 100/1, more preferably from 1/100 to 100/5.

The photographic material of the present invention preferably has slipperiness. The slipping agent-containing layer is preferably provided on both of the light-sensitive layer surface and the back surface. The preferred slipperiness is in terms of a coefficient of dynamic friction, from 0.01 to 0.25. The value is determined using a stainless steel ball having a diameter of 5 mm while transporting the photographic material at a speed of 60 cm/min (25° C., 60% RH). In this evaluation, even when the other party is changed to the light-sensitive layer surface, the value almost on the same level is obtained.

The slipping agent which can be used in the present invention includes polyorgarrosiloxane, a higher fatty acid amide, a higher fatty acid metal salt and an ester of a higher fatty acid with a higher alcohol. Examples of the polyorganosiloxane include polydimethylsiloxane, polydiethylsiloxane, polystyrylmethylsiloxane and polymethylphenylsiloxane. The layer to which the slipping agent is added is preferably an outermost layer of the emulsion layer or a back layer. In particular, polydimethylsiloxane and an ester having a long chain alkyl group are preferred.

The photographic material of the present invention preferably contains a matting agent. The matting agent may be provided either on the emulsion surface or on the back surface, but it is particularly preferably added to the outermost layer on the emulsion layer side. The matting agent may be either soluble or insoluble in the processing solution, and preferably, both of these two kinds of matting agents are used in combination. For example, polymethyl methacrylate, poly(methyl methacrylate/methacrylic acid= 9/1 or 5/5 (by mol)) and polystyrene particles are preferred. The particle size is preferably from 0.8 to 10 $\mu$m, the particle size distribution is preferably narrower, and 90% by number or more of all particles preferably have a size between 0.9 and 1.1 times the average particle size. In order to increase the matting property, fine particles of 0.8 $\mu$m or less are preferably added at the same time and examples thereof include polymethyl methacrylate (0.2 $\mu$m), poly(methyl methacrylate/methacrylic acid=9/1 (by mol), 0.3 $\mu$m), polystyrene particles (0.25 $\mu$m) and colloidal silica (0.03 $\mu$m).

The film patrone which is preferably used for the present invention is described below. The patrone may use a metal or a synthetic plastic as a main material.

Preferred plastic materials are polystyrene, polyethylene, polypropylene and polyphenyl ether. The patrone of the present invention may further contain various antistatic agents and preferred examples thereof include carbon black, metal oxide particles, nonionic, anionic, cationic and betaine surface active agents and polymers. The patrone imparted with the antistatic property is described in JP-A-1-312537 and JP-A-1-312538. In particular, the resistance at 25° C. and 25% RH is preferably $10^{12}\Omega$ or less. Usually, the plastic patrone is produced using a plastic having kneaded therein carbon black or a pigment so as to give light-shielding property. The patrone may be in a 135 size currently used but, in achieving down-sizing of camera, it is also effective to reduce the cartridge size from 25 mm of 135 size currently populated to 22 mm or less. The volume of the patrone case is preferably 30 cm$^3$ or less, more preferably 25 cm$^3$ or less. The weight of plastics used in the patrone and the patrone case is preferably from 5 to 15 g.

A patrone which sends forth the film by the rotation of a spool may be used. Also, the patrone may have such a constitution that a film leading end is housed in the patrone body and the film leading end is sent forth from the port part of the patrone to the outside by rotating the spool shaft in the film delivery direction. These are disclosed in U.S. Pat. Nos. 4,834,306 and 5,226,613. The photographic film for use in the present invention may be a so-called green film before development or a developed photographic film. Also, a green film and a developed photographic film may be housed in the same new patrone or in different patrones.

The present invention is described below in greater detail with reference to the Examples, however, the present invention should not be construed as being limited thereto.

EXAMPLE 1

Sample 101 as a multi-layer color photographic material was prepared to have layers each having the following composition, on a cellulose triacetate film support subjected to undercoating.

Composition of Light-Sensitive Layer

The coating amounts are expressed, in the case of silver halide and colloid silver, by the unit of g/m² of silver, in the case of couplers, additives and gelatin, by the unit of $g/m^2$ and, in the case of sensitizing dyes, by molar number per mol of silver halide in the same layer. The symbols used for additives have the following meanings. When the additive has a plurality of effects, one of the effects is used as a representative.

| | |
|---|---|
| UV | ultraviolet absorbent, |
| Solv | high boiling point organic solvent |
| ExF | dye |
| ExS | sensitizing dye |
| ExC | cyan coupler |
| ExM | magenta coupler |
| ExY | yellow coupler |
| Cpd | additive |

First Layer (antihalation layer)

| | |
|---|---|
| Black colloidal silver | 0.18 |
| Gelatin | 2.10 |
| UV-1 | $1.9 \times 10^{-2}$ |
| UV-2 | $4.0 \times 10^{-2}$ |
| UV-3 | $8.6 \times 10^{-2}$ |
| ExF-3 | $5.0 \times 10^{-3}$ |
| ExM-3 | $2.3 \times 10^{-2}$ |
| Solv-1 | 0.16 |
| Solv-2 | 0.10 |

Second Layer (interlayer)

| | |
|---|---|
| Gelatin | 0.88 |
| Polyethylacrylate latex | $2.6 \times 10^{-1}$ |
| ExC-7 | $5.0 \times 10^{-2}$ |

Third Layer (low-sensitivity red-sensitive emulsion layer)

| | |
|---|---|
| Silver Iodobromide Emulsion A | as silver 0.20 |
| Silver Iodobromide Emulsion B | as silver 0.60 |
| Gelatin | 1.75 |
| ExS-1 | $6.9 \times 10^{-4}$ |
| ExS-2 | $4.0 \times 10^{-4}$ |
| ExS-5 | $6.7 \times 10^{-4}$ |
| ExS-7 | $1.4 \times 10^{-5}$ |
| ExC-1 | $3.2 \times 10^{-1}$ |
| ExC-5 | $2.2 \times 10^{-1}$ |
| ExC-9 | $2.2 \times 10^{-2}$ |
| Cpd-4 | $5.3 \times 10^{-2}$ |
| ExC-4 | $6.1 \times 10^{-2}$ |

Fourth Layer (medium-sensitivity red-sensitive emulsion layer)

| | |
|---|---|
| Silver Iodobromide Emulsion C | as silver 0.72 |
| Gelatin | 0.98 |
| ExS-1 | $3.5 \times 10^{-4}$ |
| ExS-2 | $2.0 \times 10^{-4}$ |
| ExS-5 | $3.4 \times 10^{-4}$ |
| ExS-7 | $6.9 \times 10^{-6}$ |
| ExC-1 | $1.0 \times 10^{-1}$ |
| ExC-3 | $1.0 \times 10^{-2}$ |
| ExC-4 | $4.3 \times 10^{-2}$ |
| ExC-5 | $8.6 \times 10^{-2}$ |
| ExC-6 | $1.1 \times 10^{-2}$ |
| ExC-7 | $4.6 \times 10^{-2}$ |
| Cpd-4 | $2.1 \times 10^{-2}$ |

Fifth Layer (high-sensitivity red-sensitive emulsion layer)

| | |
|---|---|
| Silver Iodobromide Emulsion D | as silver 0.63 |
| Gelatin | 0.65 |
| ExS-1 | $3.2 \times 10^{-4}$ |
| ExS-2 | $1.8 \times 10^{-4}$ |
| ExS-5 | $3.1 \times 10^{-4}$ |
| ExS-7 | $4.8 \times 10^{-5}$ |
| ExC-1 | $4.8 \times 10^{-1}$ |
| ExC-6 | $9.0 \times 10^{-3}$ |
| ExC-4 | $1.8 \times 10^{-2}$ |
| ExC-8 | $5.0 \times 10^{-3}$ |
| ExC-9 | $1.0 \times 10^{-2}$ |
| Cpd-4 | $2.1 \times 10^{-3}$ |
| Solv-1 | 0.08 |
| Solv-2 | 0.04 |

Sixth Layer (interlayer)

| | |
|---|---|
| Gelatin | 0.62 |
| Cpd-1 | 0.08 |
| Polyethylacrylate latex | $4.1 \times 10^{-2}$ |
| Solv-1 | $4.0 \times 10^{-2}$ |

Seventh Layer (low-sensitivity green-sensitive emulsion layer)

| | |
|---|---|
| Silver Iodobromide Emulsion E | as silver 0.14 |
| Gelatin | 0.49 |
| ExS-8 | $5.7 \times 10^{-5}$ |
| ExS-4 | $9.0 \times 10^{-4}$ |
| ExS-5 | $1.8 \times 10^{-4}$ |
| ExM-1 | 0.26 |
| Solv-1 | 0.15 |
| Solv-3 | $7.0 \times 10^{-3}$ |

Eighth Layer (medium-sensitivity green-sensitive emulsion layer)

| | |
|---|---|
| Silver Iodobromide Emulsion F | as silver 0.10 |
| Silver Iodobromide Emulsion E | as silver 0.01 |
| Gelatin | 0.14 |
| ExS-8 | $4.3 \times 10^{-5}$ |
| ExS-4 | $6.8 \times 10^{-4}$ |
| ExS-5 | $1.3 \times 10^{-4}$ |
| ExM-1 | $4.7 \times 10^{-2}$ |
| ExM-4 | $2.0 \times 10^{-3}$ |
| ExM-7 | $1.0 \times 10^{-2}$ |
| ExY-1 | $5.0 \times 10^{-3}$ |
| Solv-1 | $3.3 \times 10^{-2}$ |
| Solv-3 | $1.5 \times 10^{-3}$ |

Ninth Layer (high-sensitivity green-sensitive emulsion layer)

| | |
|---|---|
| Silver Iodobromide Emulsion G | as silver 0.58 |
| Gelatin | 0.60 |
| ExS-4 | $5.0 \times 10^{-4}$ |
| ExS-5 | $9.9 \times 10^{-5}$ |
| ExS-8 | $3.2 \times 10^{-5}$ |
| ExM-7 | $2.2 \times 10^{-2}$ |
| ExM-1 | $8.0 \times 10^{-2}$ |
| ExM-5 | $1.0 \times 10^{-2}$ |
| ExM-6 | $5.0 \times 10^{-3}$ |
| ExY-1 | $6.7 \times 10^{-2}$ |
| ExC-1 | $6.0 \times 10^{-3}$ |
| ExC-4 | $8.0 \times 10^{-3}$ |
| Cpd-6 | $8.0 \times 10^{-3}$ |
| Solv-1 | 0.12 |
| Solv-2 | 0.06 |
| Solv-3 | $6.0 \times 10^{-3}$ |

Tenth Layer (interlayer)

| | |
|---|---|
| Gelatin | 0.39 |
| UV-2 | $1.4 \times 10^{-2}$ |
| UV-3 | $1.6 \times 10^{-2}$ |
| UV-5 | $4.2 \times 10^{-2}$ |
| Cpd-1 | $2.6 \times 10^{-2}$ |
| Polyethylacrylate latex | $1.4 \times 10^{-2}$ |
| Solv-1 | $2.8 \times 10^{-2}$ |

Eleventh Layer (donor layer having interlayer effect to red-sensitive layer)

| | |
|---|---|
| Silver Iodobromide Emulsion H | as silver 1.10 |
| Silver Iodobromide Emulsion I | as silver 0.24 |
| Gelatin | 1.61 |
| ExS-3 | $6.4 \times 10^{-4}$ |
| ExM-2 | $2.7 \times 10^{-2}$ |
| ExM-1 | $1.8 \times 10^{-1}$ |
| ExM-7 | $1.5 \times 10^{-1}$ |
| ExY-2 | $2.0 \times 10^{-1}$ |
| Solv-1 | 0.50 |

-continued

Twelfth Layer (yellow filter layer)

| | |
|---|---|
| Yellow colloidal silver | $3.3 \times 10^{-2}$ |
| Gelatin | 0.61 |
| Cpd-1 | $4.3 \times 10^{-2}$ |
| Cpd-2 | $7.9 \times 10^{-2}$ |
| Cpd-5 | $1.0 \times 10^{-3}$ |
| Solv-1 | $4.7 \times 10^{-2}$ |

Thirteenth Layer (low-sensitivity blue-sensitive emulsion layer)

| | |
|---|---|
| Silver Iodobromide Emulsion J | as silver 0.60 |
| Gelatin | 1.65 |
| ExS-9 | $8.8 \times 10^{-4}$ |
| ExY-2 | $1.2 \times 10^{-1}$ |
| ExY-3 | $5.0 \times 10^{-1}$ |
| ExC-9 | $4.0 \times 10^{-2}$ |
| ExY-5 | $5.0 \times 10^{-2}$ |
| ExY-7 | $2.0 \times 10^{-2}$ |
| ExY-8 | $1.0 \times 10^{-2}$ |
| ExC-1 | $3.0 \times 10^{-2}$ |
| ExC-10 | $8.4 \times 10^{-2}$ |
| Solv-1 | 0.33 |

Fourteenth Layer (high-sensitivity blue-sensitive emulsion layer)

| | |
|---|---|
| Silver Iodobromide Emulsion K | as silver 0.20 |
| Silver Iodobromide Emulsion L | as silver 0.15 |
| Silver Iodobromide Emulsion M | as silver 0.22 |
| Gelatin | 1.00 |
| ExS-6 | $4.4 \times 10^{-4}$ |
| ExY-2 | $7.6 \times 10^{-2}$ |
| ExY-3 | $1.3 \times 10^{-1}$ |
| ExY-6 | $3.2 \times 10^{-1}$ |
| ExY-8 | $4.0 \times 10^{-2}$ |
| ExC-1 | $1.8 \times 10^{-2}$ |
| ExC-10 | $2.3 \times 10^{-2}$ |
| Solv-1 | $1.7 \times 10^{-1}$ |

Fifteenth Layer (first protective layer)

| | |
|---|---|
| Fine Grain Silver Iodobromide Emulsion N | as silver 0.06 |
| Gelatin | 0.51 |
| UV-2 | $4.0 \times 10^{-2}$ |
| UV-3 | $4.9 \times 10^{-2}$ |
| UV-4 | 0.02 |
| UV-5 | 0.12 |
| Cpd-3 | 0.10 |
| ExF-4 | $2.1 \times 10^{-2}$ |
| ExF-5 | $6.3 \times 10^{-3}$ |
| Solv-4 | $2.0 \times 10^{-2}$ |
| Polyethylacrylate latex | $9.0 \times 10^{-2}$ |

Sixteenth Layer (second protective layer)

| | |
|---|---|
| Fine Grain Silver Iodobromide Emulsion N | as silver 0.18 |
| Gelatin | 0.84 |
| B'-1 (diameter: 2.0 $\mu$m) | $8.0 \times 10^{-2}$ |
| B'-2 (diameter: 2.0 $\mu$m) | $8.0 \times 10^{-2}$ |
| B'-3 | $3.0 \times 10^{-2}$ |
| W-5 | $1.8 \times 10^{-2}$ |
| H-1 | 0.18 |

To the thus-prepared sample, 1,2-benzoisothiazolin-3-one (200 ppm on average to gelatin), n-butyl-p-hydroxybenzoate (about 1,000 ppm on average to gelatin) and 2-phenoxyethanol (about 10,000 ppm on average to gelatin) were additionally added. Further, in order to provide good preservability, processability, pressure durability, antimold/bactericidal property, antistatic property and coatability, W-1, W-2, W-3, W-4, W-5, W-6, B'-1, B'-2, B'-3, B'-4, B'-5, B'-6, F-1, F-2, F-3, F-4, F-5, F-6, F-7, F-8, F-9, F-10, F-11, F-12, F-13, F-14, F-15, F-16, F-17, iron salt, lead salt, gold salt, platinum salt, iridium salt or rhodium salt was appropriately added to each layer.

TABLE 1

| | Average AgI Content (mol %) | Average Grain Size Sphere-Corresponding Diameter ($\mu$m) | Coefficient of Variation in Grain Size (%) | Diameter/Thickness Ratio | Silver Amount Ratio [core/medium/shell] (AgI content) | | Grain Structure/Form |
|---|---|---|---|---|---|---|---|
| Emulsion A | 4.7 | 0.40 | 10 | 1.0 | [40/10/50] | (1/38/1) | triple structure, cubic grain |
| Emulsion B | 1.7 | 0.46 | 15 | 5.5 | [5/55/40] | (5/2/2) | triple structure, tabular grain |
| Emulsion C | 7.9 | 0.53 | 18 | 4.0 | [6/45/49] | (2/8/9) | triple structure, tabular grain |
| Emulsion D | 8.8 | 0.65 | 15 | 3.5 | [12/59/29] | (0/12/6) | triple structure, tabular grain |
| Emulsion E | 1.7 | 0.46 | 15 | 5.0 | [5/55/40)] | (5/2/2) | triple structure, tabular grain |
| Emulsion F | 7.9 | 0.51 | 18 | 4.0 | [6/45/49)] | (2/8/9) | triple structure, tabular grain |
| Emulsion G | 3.5 | 0.55 | 15 | 3.5 | [12/59/29] | (0/5/2) | triple structure, tabular grain |
| Emulsion H | 8.0 | 0.65 | 28 | 2.5 | [33/67] | (18/3) | double structure, platy grain |
| Emulsion I | 10.3 | 0.40 | 15 | 1.0 | [25/75] | (29/4) | double structure, octahedral grain |
| Emulsion J | 1.7 | 0.52 | 15 | 4.2 | [5/55/40] | (5/2/2) | triple structure, tabular grain |
| Emulsion K | 8.8 | 0.64 | 23 | 5.2 | [7/64/29] | (0/11/8) | triple structure, tabular grain |
| Emulsion L | 3.4 | 0.80 | 18 | 4.7 | [12/56/32] | (0/1/9) | triple structure, tabular grain |
| Emulsion M | 13.9 | 1.30 | 25 | 3.0 | [35/65] | (34/3) | double structure, platy grain |
| Emulsion N | 2.0 | 0.07 | 15 | 1.0 | | | uniform structure, fine grain |

In Table 1:
(1) Emulsions A to M were subjected to reduction sensitization at the grain preparation using thiourea dioxide and thiosulfonic acid according to the example of JP-A-2-191938 (corresponding to U.S. Pat. No. 5,061,614);
(2) Emulsions A to M were subjected to gold sensitization, sulfur sensitization and selenium sensitization in the presence of the spectral sensitizing dyes described in each light-sensitive layer and sodium thiocyanate according to the example of JP-A-3-237450 (corresponding to EP-A-443453);
(3) in the preparation of tabular grains, low molecular weight gelatin was used according to the example of JP-A-1-158426;
(4) in tabular grains and regular crystal grains having a grain structure, dislocation lines were observed through a high-pressure electron microscope as described in JP-A-3-237450; and
(5) Emulsions A to M contain iridium incorporated inside the grain according to the method described in B. H. Carroll, *Photographic Science and Engineering*, 24, 265 (1980).

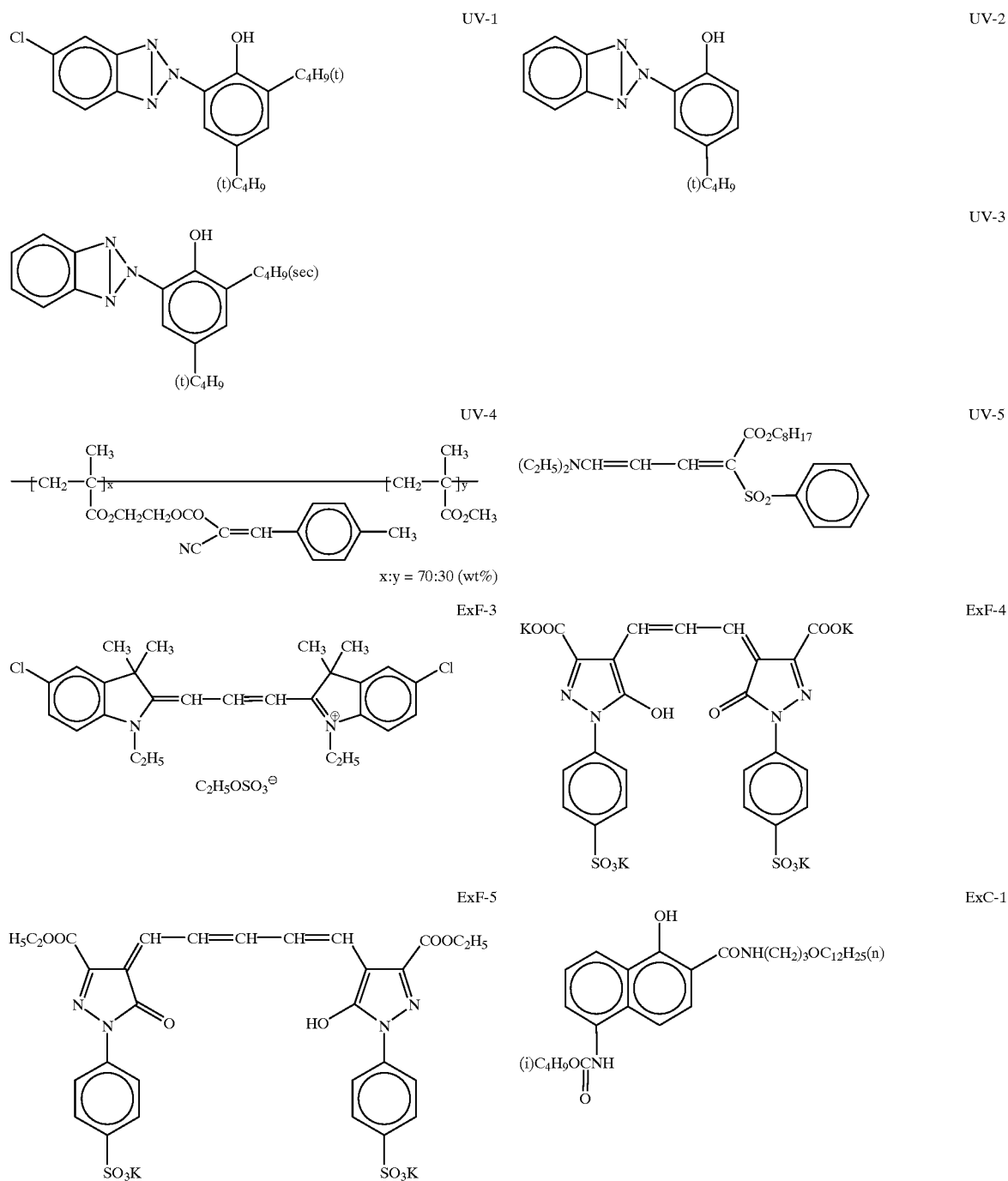

-continued
ExC-4
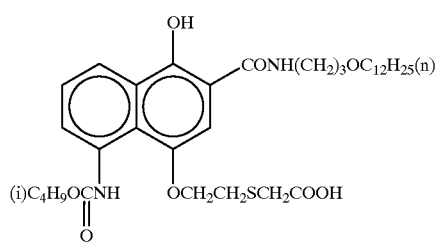
ExC-5
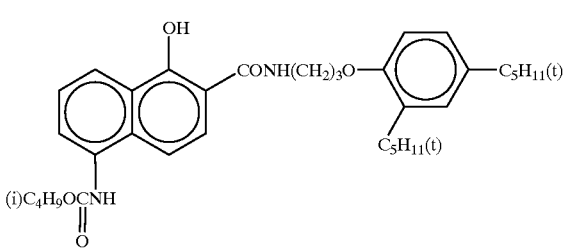
ExC-6
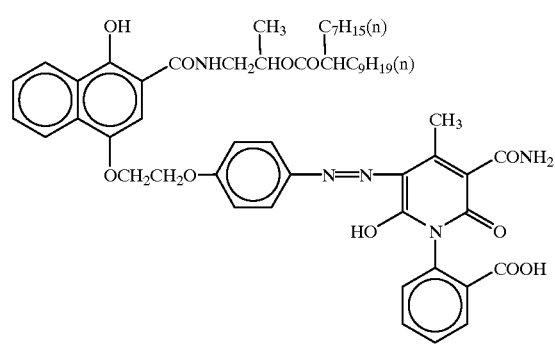
ExC-7
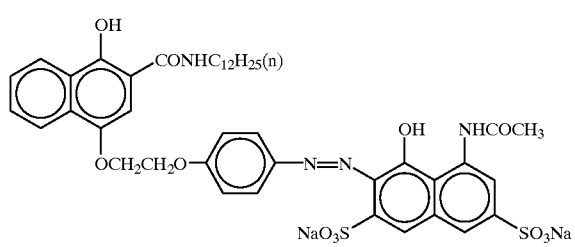
ExC-8
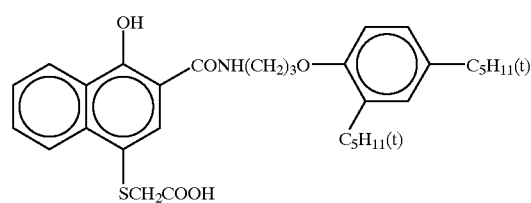
ExC-9
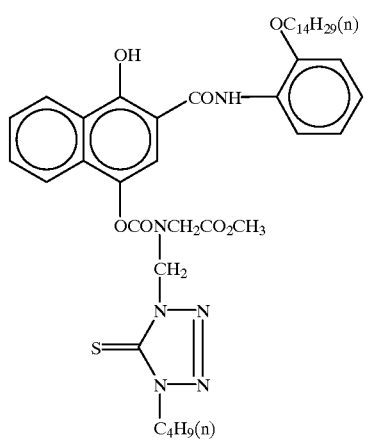
ExC-10
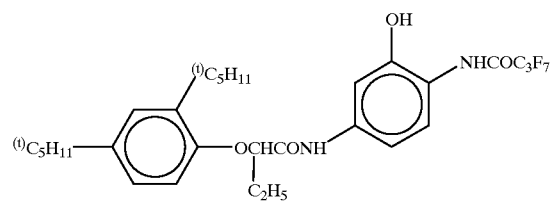

-continued
ExM-1
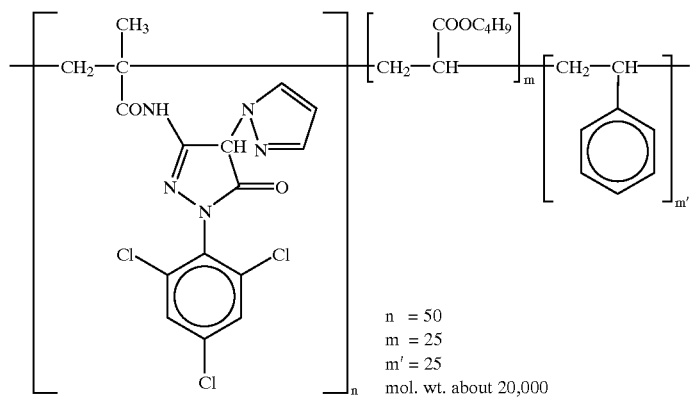
ExM-2
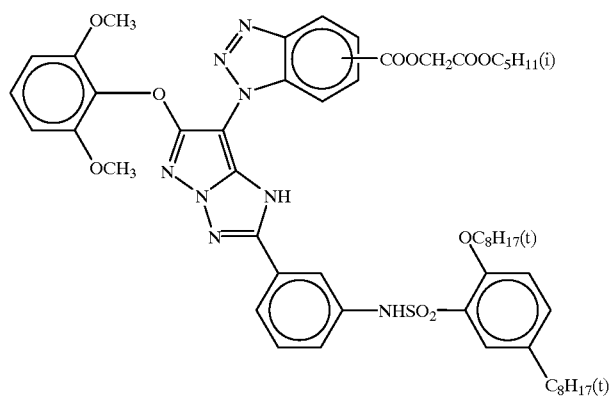
ExM-3
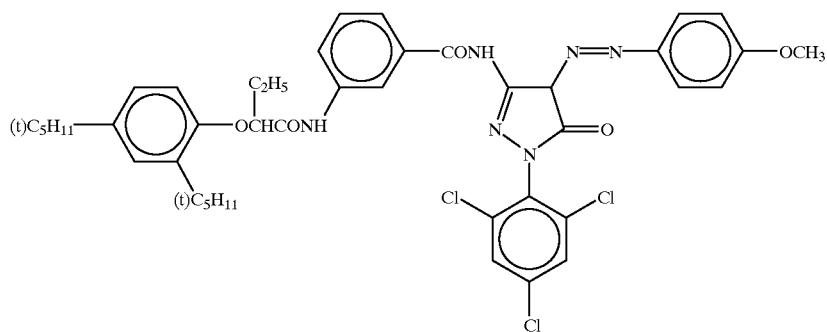
ExM-4
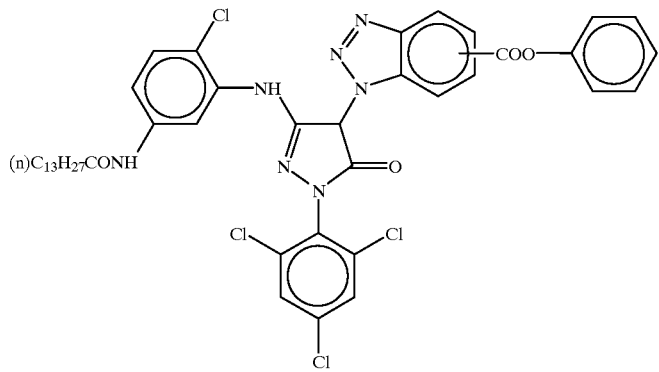

-continued
ExM-5
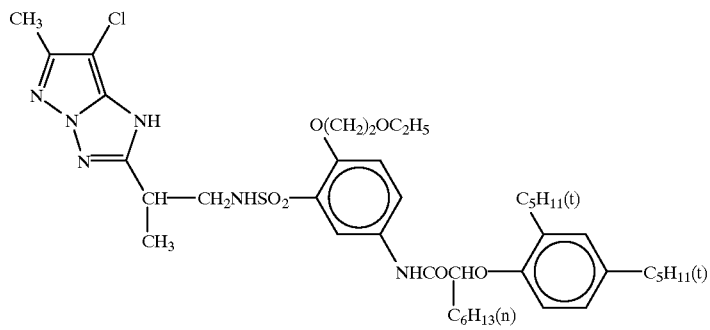
ExM-6
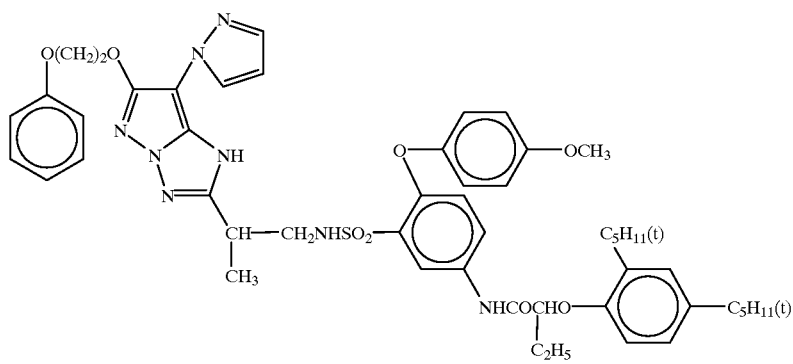
ExM-7
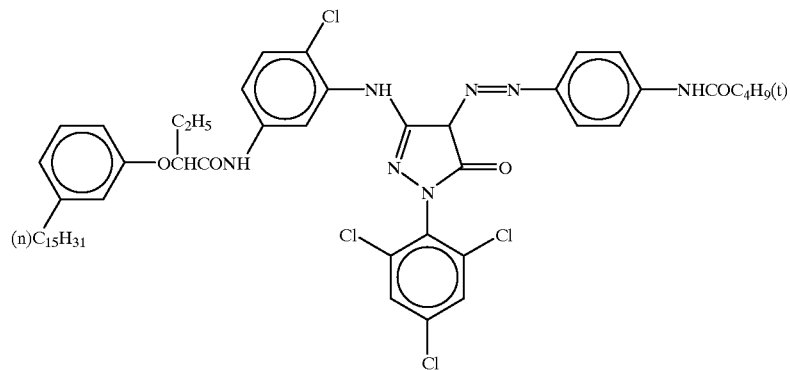
ExY-1 ExY-2
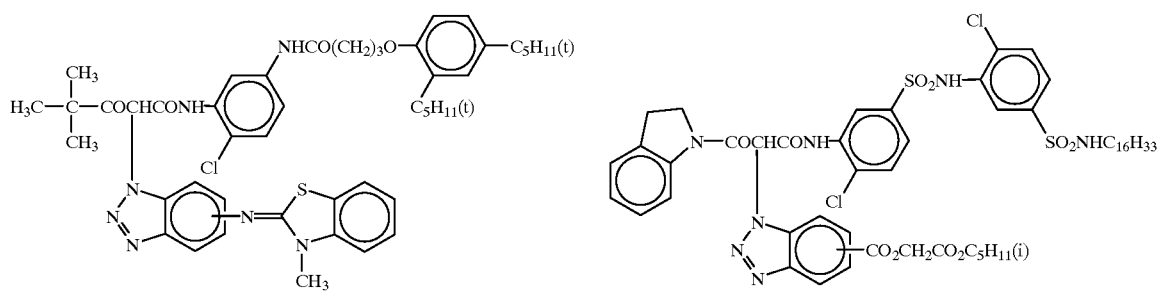

-continued
ExY-3
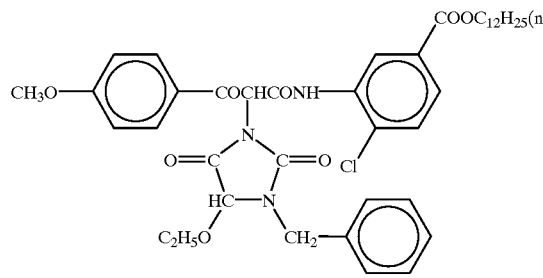
ExY-5
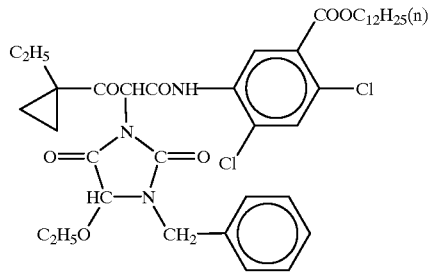
ExY-6
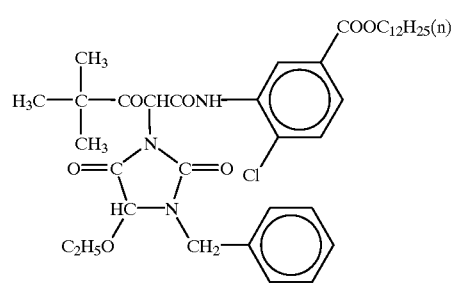
Cpd-1
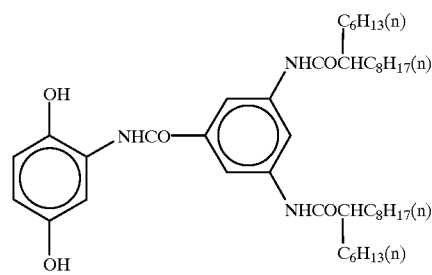
Cpd-2
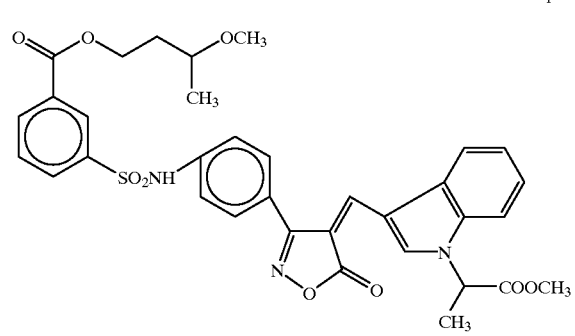
Cpd-3
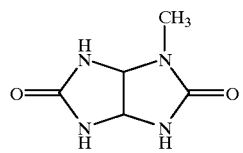
Cpd-4
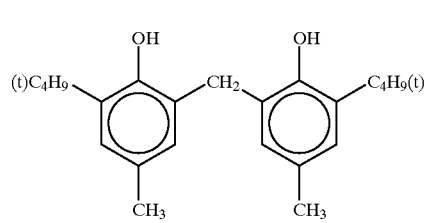
Cpd-5
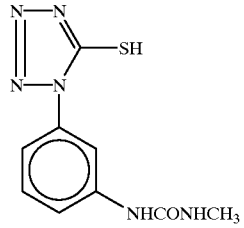
Cpd-6
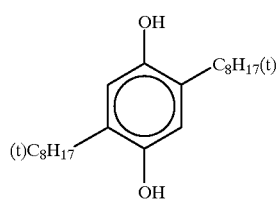
Solv-1
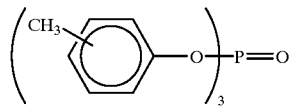
Solv-2
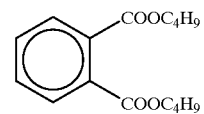
Solv-3
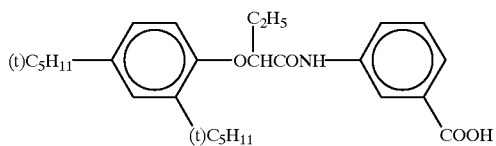

-continued
Solv-4
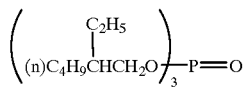
ExS-1
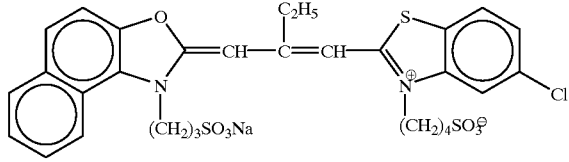
ExS-2
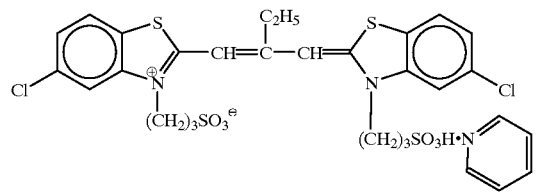
ExS-3
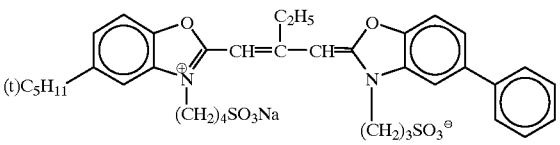
ExS-4
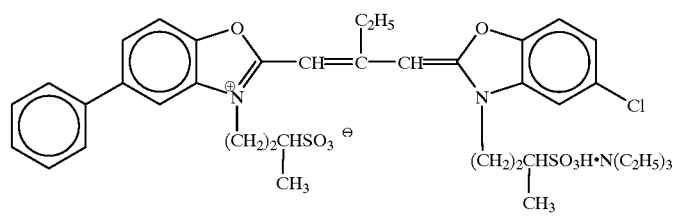
ExS-5
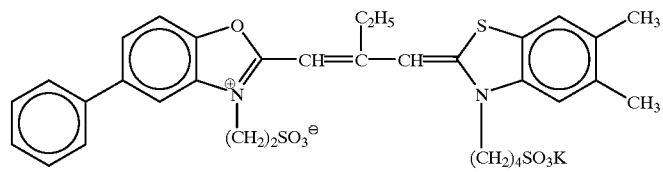
ExS-6
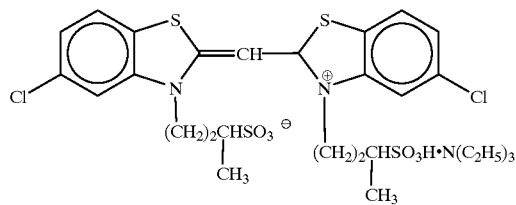
ExS-7
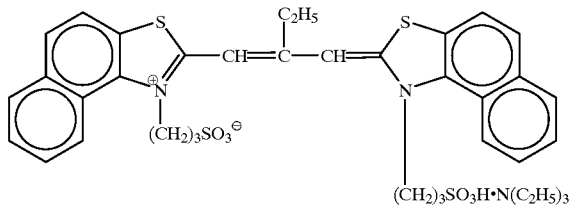
ExS-8
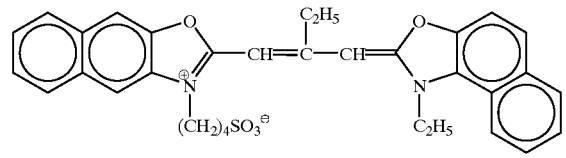
ExS-9
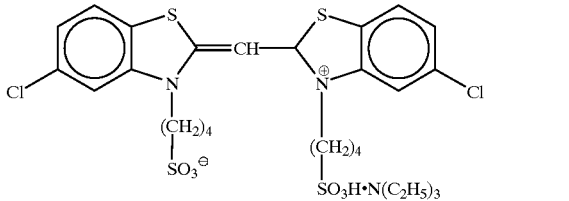
H-1
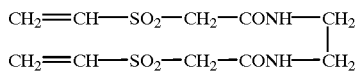
W-1
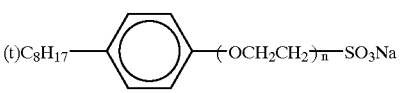
n = 2 ~ 4
W-2
W-3
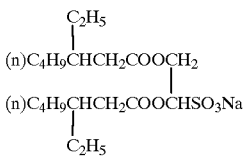

-continued

W-4

W-5: $C_8F_{17}SO_2N(C_3H_7)CH_2COOK$

W-6

B'-1: $-(CH_2-C(CH_3)-)_x-(CH_2-C(CH_3)-)_y-$ with COOH and COOCH$_3$ side groups, x/y = 10/90

B'-2

B'-3: $(CH_3)_3SiO-[Si(CH_3)(O)]_{29}-[Si(CH_3)(CH_2CH(CH_3)Ph)(O)]_{46}-Si(CH_3)_3$

B'-4

B'-5: poly(N-vinylpyrrolidone), $-(CH_2-CH)_n-$ (mol. wt. about 10,000)

B'-6

F-1: 2-mercapto-5-methylthio-1,3,4-thiadiazole (HS-C=N-N=C(SCH$_3$)-S-)

F-2: 1-(4-carboxyphenyl)-5-mercaptotetrazole, sodium salt

F-3: 1-(3-sulfophenyl)-5-mercaptotetrazole, sodium salt

F-4: 5-nitro-1H-indazole

F-5: 5-methyl-1H-benzotriazole

F-6: 2-mercaptobenzothiazole

F-7: 1-(4-carboxyphenyl)-5-mercaptotetrazole

-continued

F-8 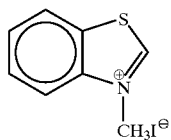

F-9 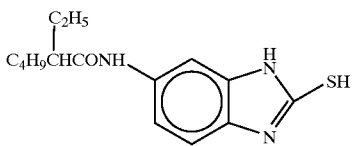

F-10 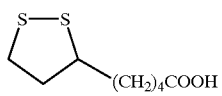

F-11 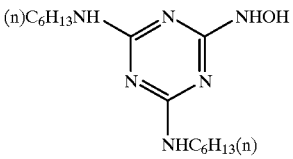

F-12 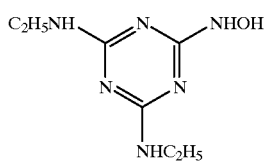

F-13 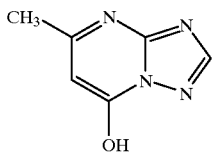

F-14 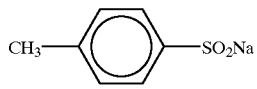

F-15 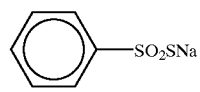

F-16 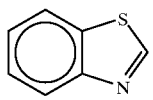

F-17 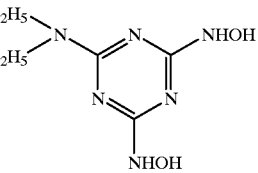

ExY-7 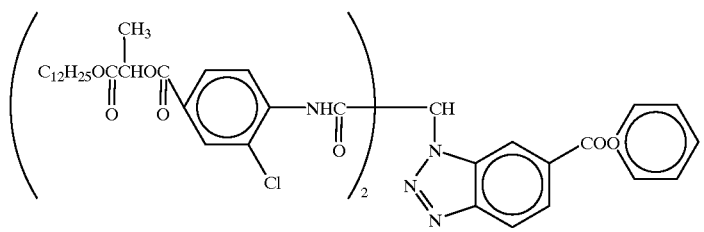

ExY-8 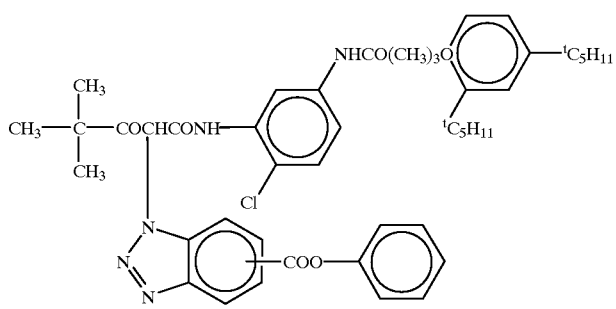

To the fourth layer of Sample 101, the compound represented by formula (IA) or a comparative compound, coemulsified with the coupler in this layer, was added to give the coated amount of $1.5 \times 10^{-2}$ mol per mol of Ag in this layer. Samples 102 to 111 as shown in Table 2 were prepared by following the preparation method of Sample 101 with respect to other conditions. When two compounds are indicated, they are used as a 1:1 by mol mixture and added to give the coated amount, in terms of the total molar number, of $1.5 \times 10^{-2}$ mol/mol-Ag.

Evaluation on the fluctuation in the photographic property after photographing until processing was performed in the following manner.

Each photographic material sample was exposed for sensitometry, stored for 3 days under forcedly deteriorating conditions of 50° C. and 60% or of 40° C. and 80%, and then subjected to the following color development processing at 38° C. The processed samples were measured on the densi through a red filter and a blue filter. The degree ° difference in the sensitivity between these samples and the sample subjected to development processing immediately after exposure was evaluated.

Each of the color photographic materials was exposed as above and then processed according to the following method.

| Processing Method | | |
|---|---|---|
| Step | Processing Time | Processing Temperature (° C.) |
| Color development | 3 min. 15 sec. | 38 |
| Bleaching | 3 min. 00 sec. | 38 |
| Water washing | 30 sec. | 24 |
| Fixing | 3 min. 00 sec. | 38 |
| Water washing (1) | 30 sec. | 24 |
| Water washing (2) | 30 sec. | 24 |
| Stabilization | 30 sec. | 38 |
| Drying | 4 min. 20 sec. | 55 |

The composition of each processing solution is shown below (unit: g)

(Color Developer)

| | |
|---|---|
| Diethylenetriaminepentaacetic acid | 1.0 |
| 1-Hydroxyethylidene-1,1-diphosphonic acid | 3.0 |
| Sodium sulfite | 4.0 |
| Potassium carbonate | 30.0 |
| Potassium bromide | 1.4 |
| Potassium iodide | 1.5 mg |
| Hydroxylamine sulfate | 2.4 |
| 4-[N-Ethyl-N-β-hydroxyethylamino]-2-methylaniline sulfate | 4.5 |
| Water to make | 1.0 liter |
| pH | 10.05 |

(Bleaching Solution)

| | |
|---|---|
| Sodium ethylenediaminetetraacetato ferrate trihydrate | 100.0 |
| Disodium ethylenediaminetetraacetate | 10.0 |
| 3-Mercapto-1,2,4-triazole | 0.03 |
| Ammonium bromide | 140.0 |
| Ammonium nitrate | 30.0 |
| Aqueous ammonia (27%) | 6.5 ml |
| Water to make | 1.0 liter |
| pH | 6.0 |

(Fixing Solution)

| | |
|---|---|
| Disodium ethylenediaminetetraacetate | 0.5 |
| Ammonium sulfite | 20.0 |
| Ammonium thiosulfate (aq. soln. 700 g/l) | 295.0 |
| Acetic acid (90%) | 3.3 |
| Water to make | 1.0 liter |
| pH | 6.7 |

(Stabilizing Solution)

| | |
|---|---|
| p-Nonylphenoxypolyglycidol (glycidol average polymerization degree: 10) | 0.2 |
| Ethylenediaminetetraacetic acid | 0.05 |
| 1,2,4-Triazole | 1.3 |
| 1,4-Bis(1,2,4-triazol-1-ylmethyl)-piperazine | 0.75 |
| Hydroxyacetic acid | 0.02 |
| Hydroxyethyl cellulose (HEC SP-2000, produced by Daicel Chemical KK) | 0.1 |
| 1,2-Benzoisothiazolin-3-one | 0.05 |
| Water to make | 1.0 liter |
| pH | 8.5 |

The sensitivity as a photographic property is shown by a logarithm of the reciprocal of an exposure amount required to give an optical density 1.0 higher than the fog. The fluctuation in the photographic property after photographing until processing is shown by a relative sensitivity (difference in logarithms) of the sensitivity of photographic materials stored after exposure under forcedly deteriorating conditions to the sensitivity of the photographic material processed immediately after exposure. The nearer to 0 the value is, the smaller the fluctuation in the photographic property is and the more preferable the material is.

Fluctuation in the photographic property both of the red-sensitive layer to which the compound of formula (IA) was added and of the blue-sensitive layer to which the compound was not added was evaluated. When the compound of formula (IA) or a comparative compound was added, the photographic property of the blue-sensitive layer changed as compared with the material (Sample 101) to which the compound was not added. This reveals that the compound disadvantageously diffused from the red-sensitive layer (layer to which the compound was added) to the blue-sensitive layer (layer to which the compound was not added).

The results are shown in Table 2.

TABLE 2

Compound A (Compound described in JP-A-59-198453)

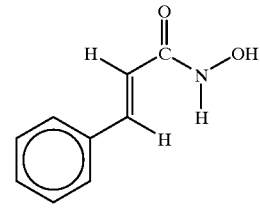

| | | Fluctuation in Photographic Property due to Aging after Photographing until Processing | | | |
|---|---|---|---|---|---|
| | | Red-Sensitive Layer | | Blue-Sensitive layer | |
| Sample | Compound | 50° C., 60% | 40° C., 80% | 50° C., 60% | 40° C., 80% |
| 101 (Comparison) | — | 0.15 | −0.02 | −0.01 | −0.02 |
| 102 (Comparison) | A | 0.10 | −0.02 | −0.03 | −0.09 |
| 103 (Invention) | A-1 | 0.02 | −0.02 | −0.01 | −0.02 |
| 104 (Invention) | A-23 | 0.06 | −0.02 | −0.01 | −0.02 |
| 105 (Invention) | A-33 | 0.02 | −0.02 | −0.01 | −0.02 |
| 106 (Invention) | A-4 | 0.02 | −0.02 | −0.01 | −0.02 |
| 107 (Invention) | A-17 | 0.02 | −0.02 | −0.01 | −0.02 |
| 108 (Invention) | A-27 | 0.03 | −0.02 | −0.01 | −0.02 |
| 109 (Invention) | A-40 | 0.03 | −0.02 | −0.01 | −0.02 |
| 110 (Invention) | A-44 | 0.02 | −0.02 | −0.01 | −0.02 |
| 111 (Invention) | A-46 | 0.03 | −0.02 | −0.01 | −0.02 |

As clearly seen from Table 2, the photographic materials using the compound of formula (IA) according to the present invention showed good results such that fluctuation in the photographic property due to aging after photographing until processing of the layer to which the compound was added (red-sensitive layer) was small and at the same time, fluctuation due to aging of the layer to which the compound was not added (blue-sensitive layer) was not worsened.

The compound of formula (IA) according to the present invention affected neither other photographic properties nor storability of the layer to which the compound was not added.

EXAMPLE 2

Other than the compounds shown in Table 2 of Example 1, using Compound A-2, A-3, A-5, A-6, A-7, A-8, A-9, A-10, A-11, A-12, A-13, A-14, A-15, A-16, A-18, A-19, A-20, A-21, A-22, A-24, A-25, A-26, A-28, A-29, A-30, A-31, A-32, A-34, A-35, A-36, A-37, A-38, A-39, A-41, A-42, A-43, A-45 or A-46 for use in the present invention, evaluation of red-sensitive layer or green-sensitive layer was conducted. As a result, these compounds provided advantageous results such that the change in the photographic property due to aging was reduced when the materials were allowed to stand after photographing.

EXAMPLE 3

When the compound for use in the present invention was used in the green-sensitive layer or the blue-sensitive layer, similarly to Example 1, good results were provided such that the storability of the layer to which the compound was added was improved and the layer to which the compound was not added was not affected.

EXAMPLE 4

Sample 401 was prepared in place of Sample 101 of Example 1.

Samples 402 to 411 corresponding to Samples 102 to 111 were prepared according to the preparation method of Sample 401 except that to the fourth layer of Sample 401, the compound represented by formula (IA) or a comparative compound, coemulsified with the coupler in this layer, was added to give the coated amount of $5 \times 10^{-2}$ mol per mol of Ag in this layer (Sample 402 is a comparative example).

When two compounds are indicated, they are used as a 1:1 by mol mixture and added to give the coated amount, in terms of the total molar number, of $5 \times 10^{-2}$ mol/mol-AgX.

Using these samples, evaluation of the compounds for use in the present invention was conducted and as a result, good capability was exhibited similarly to Example 1.

1) Support

The support used in this example was prepared according to the following method.

Polyethylene-2,6-naphthalate polymer (100 parts by weight) and 2 parts by weight of Tinuvin P.326 (produced by Ciba Geigy AG) as an ultraviolet absorbent were dried, melted at 300° C., extracted from a T-die, stretched in the machine direction at 140° C. to 3.3 times, then stretched in the transverse direction at 130° C. to 3.3 times and further heat set at 250° C. for 6 seconds to obtain a PEN film having a thickness of 90 μm. To the resulting PEN film, a blue dye, a magenta dye and a yellow dye (Compounds I-1, I-4, I-6, I-24, I-26, I-27 and II-5 described in *JIII Journal of Technical Disclosure*, No. 94-6023) were added in an appropriate amount. Further, the film was wound around a stainless steel core having a diameter of 20 cm to have heat history at 110° C. for 48 hours, thereby obtaining a support difficult of curling habit.

2) Coating of Undercoat Layer

Both surfaces of the support obtained above was subjected to corona discharge treatment, UV discharge treatment and glow discharge treatment, and an undercoating solution containing 0.1 g/m² of gelatin, 0.01 g/m² of sodium α-sulfodi-2-ethylhexylsuccinate, 0.04 g/m² of salicylic acid, 0.2 g/m² of p-chlorophenol, 0.012 g/m² of $(CH_2=CHSO_2CH_2CH_2NHCO)_2CH_2$ and 0.02 g/m² of a polyamido-epichlorohydrin polycondensate was coated (10 ml/m², using a bar coater) on one surface to provide an undercoat layer on the higher temperature side at the time of stretching. The drying was conducted at 115° C. for 6 minutes (rollers and the conveyance device in the drying zone all were heated to 115° C.).

3) Coating of Back Layer

On one surface of the undercoated support, an antistatic layer, a magnetic recording layer and a slipping layer each having the following composition were coated as a back layer.

3-1) Coating of Antistatic Layer

A fine particle powder dispersion having a resistivity of 5 Ω·cm of a tin oxide-antimony oxide composite having an average particle diameter of 0.005 μm (secondary aggregate particle size: about 0.08 μm) was coated in an amount of 0.2 g/m² together with 0.05 g/m² of gelatin, 0.02 g/m² of $(CH_2=CHSO_2CH_2CH_2NHCO)_2CH_2$, 0.005 g/m² of poly (polymerization degree: 10)oxyethylene-p-nonylphenol and 0.22 g/m² of resorcin.

3-2) Coating of Magnetic Recording Layer

Co-γ-iron oxide (0.06 g/m²) (specific surface area: 43 m²/g; longer axis: 0.14 μm; single axis: 0.03 μm; saturated magnetization: 89 emu/g; $Fe^{+2}/Fe^{+3}=6/94$; the surface being treated with aluminum oxide and silicon oxide each in an amount of 2 wt % based on iron oxide) subjected to covering treatment with 3-poly(polymerization degree: 15)oxyethylene-propyloxytrimethoxysilane (15 wt %) and dispersed in 1.2 g/m² of diacetyl cellulose (the iron oxide being dispersed by an open kneader and sand mill) and 0.3 g/m² of $C_2H_5C(CH_2OCONH\text{—}C_6H_3(CH_3)NCO)_3$ as a hardening agent were coated using acetone, methyl ethyl ketone and cyclohexanone as solvents by means of a bar coater to obtain a magnetic recording layer having a thickness of 1.2 μm. Silica particles (0.3 μm) as a matting agent and an alumina oxide (0.15 μm) subjected to covering treatment with 3-poly(polymerization degree: 15)oxyethylene-propyloxytrimethoxysilane (15 wt %) as an abrasive each was added to give a coverage of 10 mg/m². The drying was conducted at 115° C. for 6 minutes (rollers and the conveyance device in the drying zone all were heated to 115° C.). The increase in color density of the magnetic recording layer $D^B$ with X-light (blue filter) was about 0.1, the saturated magnetization moment of the magnetic recording layer was 4.2 emu/m², the coercive force was $7.3 \times 10^4$ A/m and the angular ratio was 65%.

3-3) Preparation of Slipping Layer

Diacetyl cellulose (25 mg/m²) and a mixture of $C_6H_{13}CH(OH)C_{10}H_{20}COOC_{40}H_{81}$ (Compound a, 6 mg/m²)/ $C_{50}H_{101}O(CH_2CH_2O)_{16}H$ (Compound b, 9 mg/m²) were coated. The mixture was prepared by melting the compounds in xylene/propylene monomethyl ether (1/1) at 105° C. and pouring-dispersing the melt in propylene monomethyl ether (10-fold amount) at normal temperature. The resulting mixture was formed into a dispersion (average particle size: 0.01 μm) in acetone and then added. Silica particles (0.3 μm) as a matting agent and alumina oxides (0.15 μm) covered with 3-poly(polymerization degree: 15)oxyethylenepropyloxytrimethoxysilane (15 wt %) as an abrasive each was added to give coverage of 15 mg/m². The drying was conducted at 115° C. for 6 minutes (rollers and the conveyance device in the drying zone all were heated to 115° C.). The thus-provided slipping layer had excellent capabilities such that the coefficient of dynamic friction was 0.06 (stainless steel ball: 5 mmφ; load: 100 g; speed: 6 cm/min), the coefficient of static friction was 0.07 (by clip method) and the coefficient of dynamic friction between the emulsion surface and the slipping layer, which will be described later, was 0.12.

4) Coating of Light-Sensitive Layer

The layers each having the following composition were coated to overlay one on another on the side of a support opposite to the back layer provided above to prepare a color negative film. This film was designated as Sample 401.

Composition of Light-Sensitive Layer

The main materials used in each layer are classified as follows.

| | |
|---|---|
| ExC | cyan coupler |
| ExM | magenta coupler |
| ExY | yellow coupler |
| ExS | sensitizing dye |
| UV | ultraviolet absorbent |
| HBS | high-boiling point organic solvent |
| H | gelatin hardening agent |

Numerals corresponding to respective components show coating amounts expressed by the unit of $g/m^2$ and in case of silver halide, they show coating amounts in terms of silver. With respect to sensitizing dyes, the coating amount is shown by the unit mol per mol of silver halide in the same layer.

| First Layer (antihalation layer) | |
|---|---|
| Black colloidal silver | as silver 0.09 |
| Gelatin | 1.60 |
| ExM-1 | 0.12 |
| ExF-1 | $2.0 \times 10^{-3}$ |
| Solid Disperse Dye ExF-2 | 0.030 |
| Solid Disperse Dye ExF-3 | 0.040 |
| HBS-1 | 0.15 |
| HBS-2 | 0.02 |
| Second Layer (interlayer) | |
| Silver Iodobromide Emulsion M | as silver 0.065 |
| ExC-2 | 0.04 |
| Polyethylacrylate latex | 0.20 |
| Gelatin | 1.04 |
| Third Layer (low-sensitivity red-sensitive emulsion layer) | |
| Silver Iodobromide Emulsion A | as silver 0.25 |
| Silver Iodobromide Emulsion B | as silver 0.25 |
| ExS-1 | $6.9 \times 10^{-5}$ |
| ExS-2 | $1.8 \times 10^{-5}$ |
| ExS-3 | $3.1 \times 10^{-4}$ |
| ExC-1 | 0.17 |
| ExC-3 | 0.030 |
| ExC-4 | 0.10 |
| ExC-5 | 0.020 |
| ExC-6 | 0.010 |
| Cpd-2 | 0.025 |
| HBS-1 | 0.10 |
| Gelatin | 0.87 |
| Fourth Layer (medium-sensitivity red-sensitive emulsion layer) | |
| Silver Iodobromide Emulsion C | as silver 0.70 |
| ExS-1 | $3.5 \times 10^{-4}$ |
| ExS-2 | $1.6 \times 10^{-5}$ |
| ExS-3 | $5.1 \times 10^{-4}$ |
| ExC-1 | 0.13 |
| ExC-2 | 0.060 |
| ExC-3 | 0.0070 |
| ExC-4 | 0.090 |
| ExC-5 | 0.015 |
| ExC-6 | 0.0070 |
| Cpd-2 | 0.023 |
| HBS-1 | 0.10 |
| Gelatin | 0.75 |
| Fifth Layer (high-sensitivity red-sensitive emulsion layer) | |
| Silver Iodobromide Emulsion D | as silver 1.40 |
| ExS-1 | $2.4 \times 10^{-4}$ |
| ExS-2 | $1.0 \times 10^{-4}$ |
| ExS-3 | $3.4 \times 10^{-4}$ |
| ExC-1 | 0.10 |
| ExC-3 | 0.045 |
| ExC-6 | 0.020 |
| ExC-7 | 0.010 |
| Cpd-2 | 0.050 |
| HBS-1 | 0.22 |
| HBS-2 | 0.050 |
| Gelatin | 1.10 |
| Sixth Layer (interlayer) | |
| Cpd-1 | 0.090 |
| Solid Disperse Dye ExF-4 | 0.030 |
| HBS-1 | 0.050 |
| Polyethylacrylate latex | 0.15 |
| Gelatin | 1.10 |
| Seventh Layer (low-sensitivity green-sensitive emulsion layer) | |
| Silver Iodobromide Emulsion E | as silver 0.15 |
| Silver Iodobromide Emulsion F | as silver 0.10 |
| Silver Iodobromide Emulsion G | as silver 0.10 |
| ExS-4 | $3.0 \times 10^{-5}$ |
| ExS-5 | $2.1 \times 10^{-4}$ |
| ExS-6 | $8.0 \times 10^{-4}$ |
| ExM-2 | 0.33 |
| ExM-3 | 0.086 |
| ExY-1 | 0.015 |
| HBS-1 | 0.30 |
| HBS-3 | 0.010 |
| Gelatin | 0.73 |
| Eighth Layer (medium-sensitivity green-sensitive emulsion layer) | |
| Silver Iodobromide Emulsion H | as silver 0.80 |
| ExS-4 | $3.2 \times 10^{-5}$ |
| ExS-5 | $2.2 \times 10^{-4}$ |
| ExS-6 | $8.4 \times 10^{-4}$ |
| ExC-8 | 0.010 |
| ExM-2 | 0.10 |
| ExM-3 | 0.025 |
| ExY-1 | 0.018 |
| ExY-4 | 0.010 |
| ExY-5 | 0.040 |
| HBS-1 | 0.13 |
| HBS-3 | $4.0 \times 10^{-3}$ |
| Gelatin | 0.80 |
| Ninth Layer (high-sensitivity green-sensitive emulsion layer) | |
| Silver Iodobromide Emulsion I | as silver 1.25 |
| ExS-4 | $3.7 \times 10^{-5}$ |
| ExS-5 | $8.1 \times 10^{-5}$ |
| ExS-6 | $3.2 \times 10^{-4}$ |
| ExC-1 | 0.010 |
| ExM-1 | 0.020 |
| ExM-4 | 0.025 |
| ExM-5 | 0.040 |
| Cpd-3 | 0.040 |
| HBS-1 | 0.25 |
| Polyethylacrylate latex | 0.15 |
| Gelatin | 1.33 |
| Tenth Layer (yellow filter layer) | |
| Yellow colloidal silver | as silver 0.015 |
| Cpd-1 | 0.16 |
| Solid Disperse Dye ExF-5 | 0.060 |
| Solid Disperse Dye ExF-6 | 0.060 |
| Oil-Soluble Dye ExF-7 | 0.010 |
| HBS-1 | 0.60 |
| Gelatin | 0.60 |

-continued

| Eleventh Layer (low-sensitivity blue-sensitive emulsion layer) | |
| --- | --- |
| Silver Iodobromide Emulsion J | as silver 0.09 |
| Silver Iodobromide Emulsion K | as silver 0.09 |
| ExS-7 | $8.6 \times 10^{-4}$ |
| ExC-8 | $7.0 \times 10^{-4}$ |
| ExY-1 | 0.050 |
| ExY-2 | 0.22 |
| ExY-3 | 0.50 |
| ExY-4 | 0.020 |
| Cpd-2 | 0.10 |
| Cpd-3 | $4.0 \times 10^{-3}$ |
| HBS-1 | 0.28 |
| Gelatin | 1.20 |
| Twelfth Layer (high-sensitivity blue-sensitive emulsion layer) | |
| Silver Iodobromide Emulsion L | as silver 1.00 |
| ExS-7 | $4.0 \times 10^{-4}$ |
| ExY-2 | 0.10 |
| ExY-3 | 0.10 |
| ExY-4 | 0.010 |
| Cpd-2 | 0.10 |
| Cpd-3 | $1.0 \times 10^{-3}$ |
| HBS-1 | 0.070 |
| Gelatin | 0.70 |
| Thirteenth Layer (first protective layer) | |
| UV-1 | 0.19 |
| UV-2 | 0.075 |
| UV-3 | 0.065 |
| HBS-1 | $5.0 \times 10^{-2}$ |
| HBS-4 | $5.0 \times 10^{-2}$ |
| Gelatin | 1.8 |
| Fourteenth Layer (second protective layer) | |
| Silver Iodobromide Emulsion M | as silver 0.10 |
| H-1 | 0.40 |
| B'-1 (diameter: 1.7 μm) | $5.0 \times 10^{-2}$ |
| B'-2 (diameter: 1.7 μm) | 0.15 |
| B'-3 | 0.05 |
| S-1 | 0.20 |
| Gelatin | 0.70 |

Further, in order to provide good preservability, processability, pressure durability, antimold/bactericidal property, antistatic property and coatability, W-1, W-2, W-3, B'-4, B'-5, B'-6, F-1, F-2, F-3, F-4, F-5, F-6, F-7, F-8, F-9, F-10, F-11, F-12, F-13, F-14, F-15, F-16, F-17, iron salt, lead salt, gold salt, platinum salt, palladium salt, iridium salt or rhodium salt was appropriately added to each layer.

In Table 3:

(1) Emulsions J to L were subjected to reduction sensitization at the grain preparation using thiourea dioxide and thiosulfonic acid according to the example of JP-A-2-191938 (corresponding to U.S. Pat. No. 5,061, 614);

(2) Emulsions A to I were subjected to gold sensitization, sulfur sensitization and selenium sensitization in the presence of the spectral sensitizing dyes described in each light-sensitive layer and sodium thiocyanate according to the example of JP-A-3-237450 (corresponding to EP-A-4434S3);

(3) in the preparation of tabular grains, low molecular weight gelatin was used according to the example of JP-A-1-158426;

(4) in tabular grains, dislocation lines were observed through a high-pressure electron microscope as described in JP-A-3-237450 (corresponding to EP-A-443453); and (5) Emulsion L is a double structure grain containing an inner high iodide core described in JP-A-60-143331.

Preparation of Dispersion Product of Organic Solid Disperse Dye

Solid Disperse Dye ExF-2 was dispersed as follows. That is, 21.7 ml of water, 3 ml of a 5% aqueous solution of sodium p-octylphenoxyethoxyethoxyethanesulfonate and 0.5 g of a 5% aqueous solution of p-octylphenoxypolyoxyethylene ether (polymerization degree: 10) were poured into a 700 ml-volume pot mill, then thereto 5.0 g of Dye ExF-2 and 500 ml of zirconium oxide beads (diameter: 1 mm) were added and the content was dispersed for 2 hours. In this dispersion, a BO-type vibration ball mill manufactured by Chuo Koki KK was used. After the dispersion, the content was taken out and added to 8 g of a 12.5% aqueous gelatin solution and the beads were removed by filtration to obtain a gelatin dispersion of the dye. The dye fine particles had an average particle size of 0.44 μm.

Solid dispersion products of ExF-3, ExF-4 and ExF-6 each was obtained in the same manner. The average particle size of dye fine particles was 0.24, 0.45 or 0.52 μm, respectively. ExF-5 was dispersed by the microprecipitation dispersion method described in Example 1 of EP-A-549489. The average particle size was 0.06 μm.

TABLE 3

| | Average AgI Content (%) | Coefficient of Variation in AgI Content among Grains (%) | Average Grain Size, Sphere-Corresponding Diameter (μm) | Coefficient of Variation in Grain Size (%) | Projected Area, Circle-Corresponding Diameter (μm) | Diameter/Thickness Ratio |
| --- | --- | --- | --- | --- | --- | --- |
| Emulsion A | 1.7 | 10 | 0.46 | 15 | 0.56 | 5.5 |
| Emulsion B | 3.5 | 15 | 0.57 | 20 | 0.78 | 4.0 |
| Emulsion C | 8.9 | 25 | 0.66 | 25 | 0.87 | 5.8 |
| Emulsion D | 8.9 | 18 | 0.84 | 26 | 1.03 | 3.7 |
| Emulsion E | 1.7 | 10 | 0.46 | 15 | 0.56 | 5.5 |
| Emulsion F | 3.5 | 15 | 0.57 | 20 | 0.78 | 4.0 |
| Emulsion G | 8.8 | 25 | 0.61 | 23 | 0.77 | 4.4 |
| Emulsion H | 8.8 | 25 | 0.61 | 23 | 0.77 | 4.4 |
| Emulsion I | 8.9 | 18 | 0.84 | 26 | 1.03 | 3.7 |
| Emulsion J | 1.7 | 10 | 0.46 | 15 | 0.50 | 4.2 |
| Emulsion K | 8.8 | 18 | 0.64 | 23 | 0.85 | 5.2 |
| Emulsion L | 14.0 | 25 | 1.28 | 26 | 1.46 | 3.5 |
| Emulsion M | 1.0 | — | 0.07 | 15 | — | 1 |

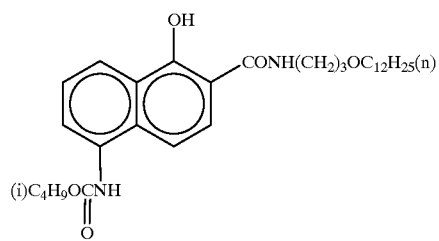
ExC-1
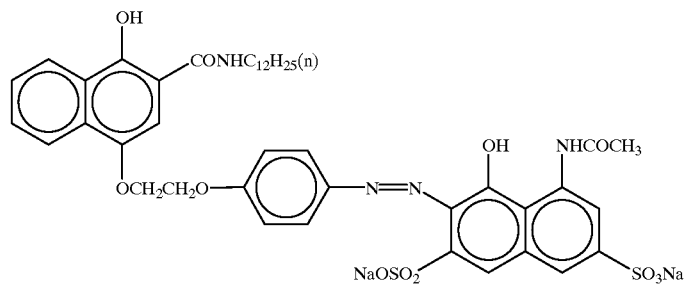
ExC-2
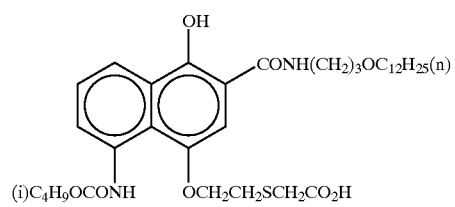
ExC-3
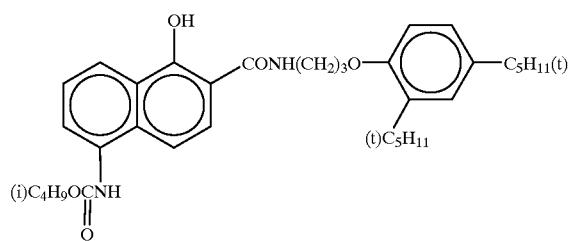
ExC-4
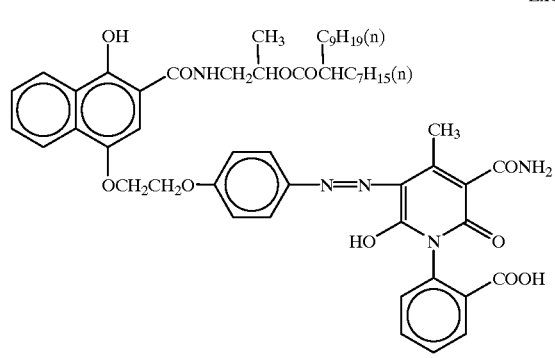
ExC-5
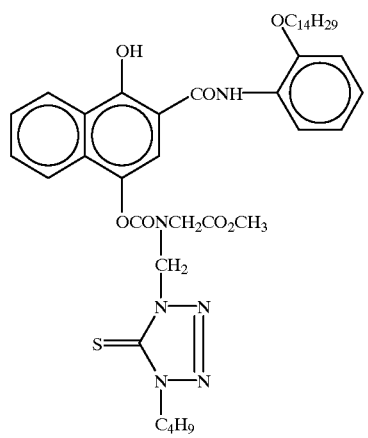
ExC-6

-continued
ExC-7
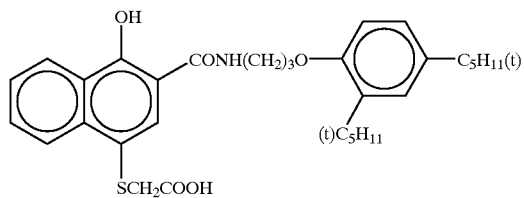
ExC-8
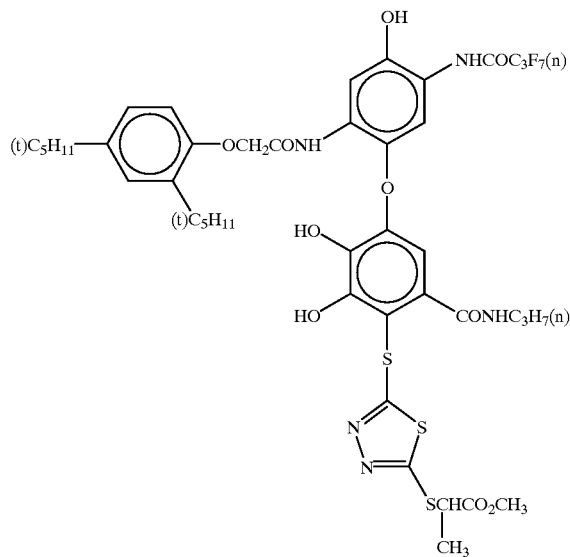
ExM-1
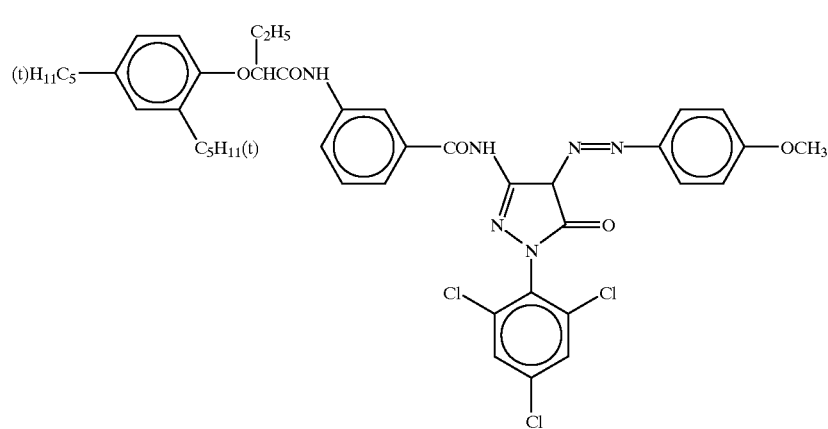
ExM-2
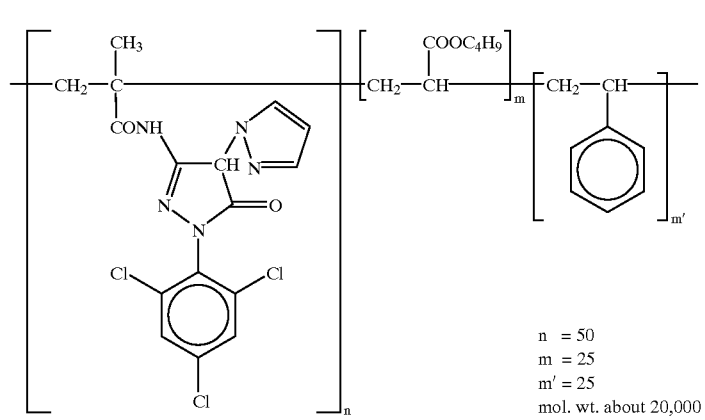
n = 50
m = 25
m' = 25
mol. wt. about 20,000

ExM-3
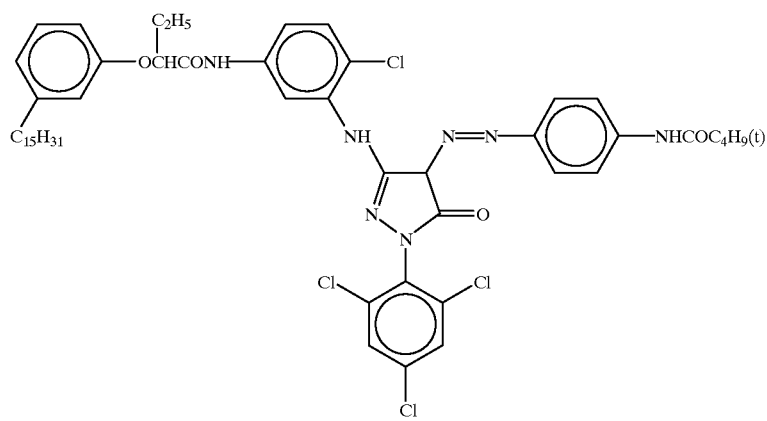
ExM-4
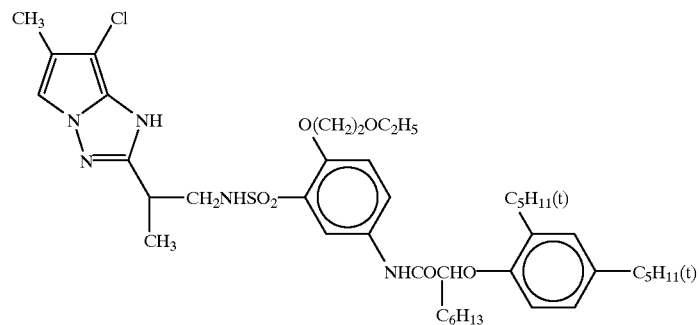
ExM-5
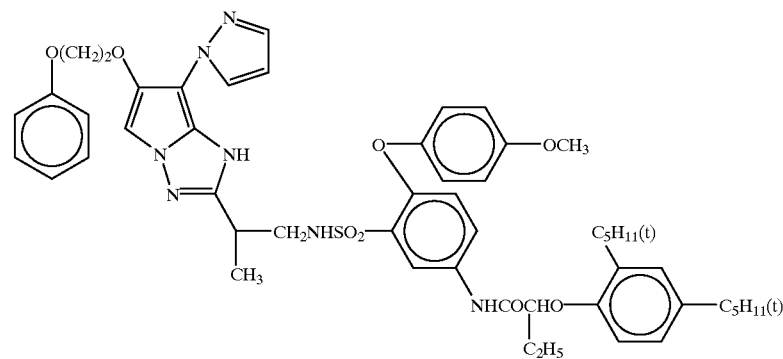
ExY-1
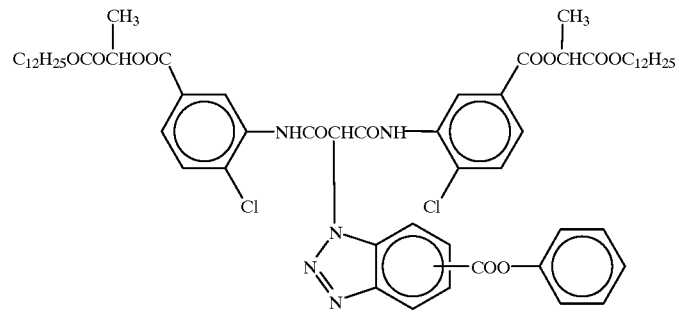

-continued
ExY-2
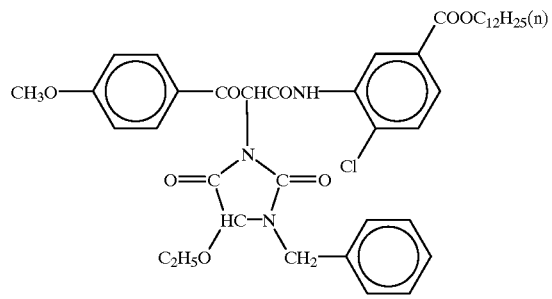
ExY-3
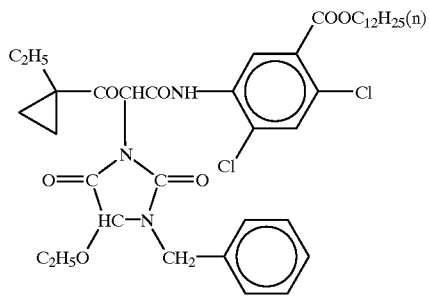
ExY-4
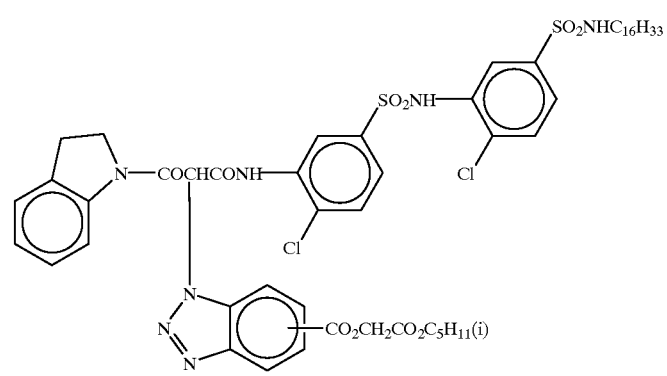
ExY-5
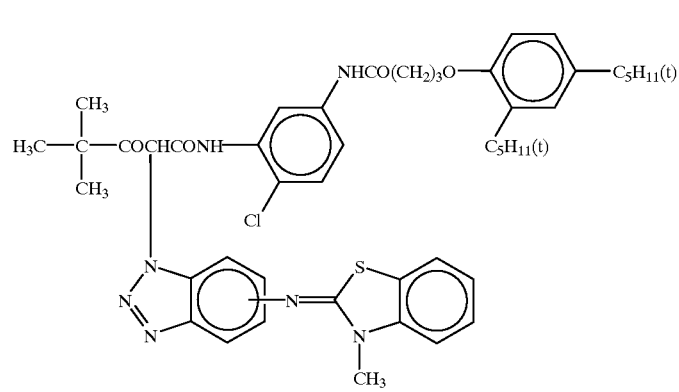
ExF-1
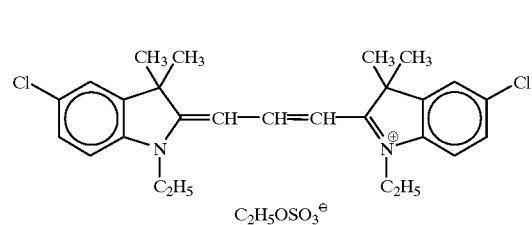
ExF-2
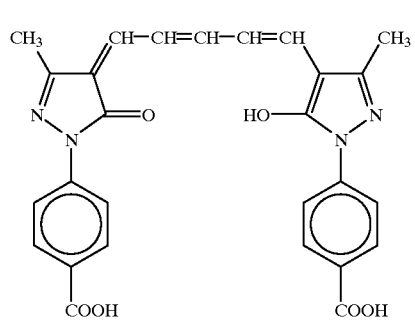

-continued
ExF-3
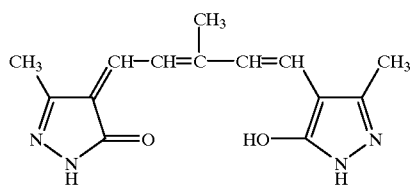
ExF-4
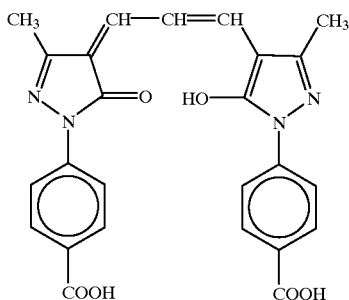
ExF-5
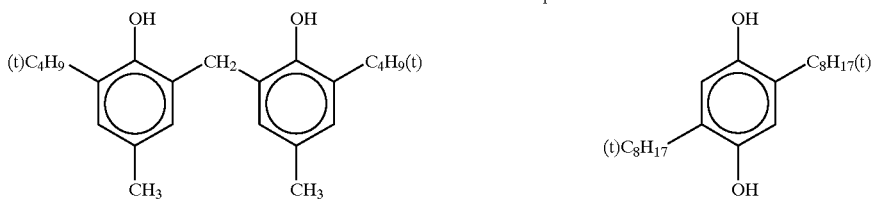
ExF-6
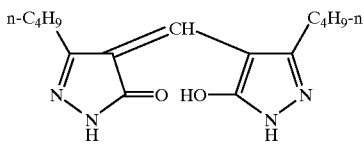
ExF-7
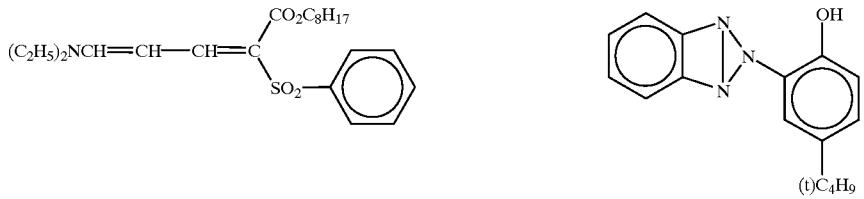
Cpd-1
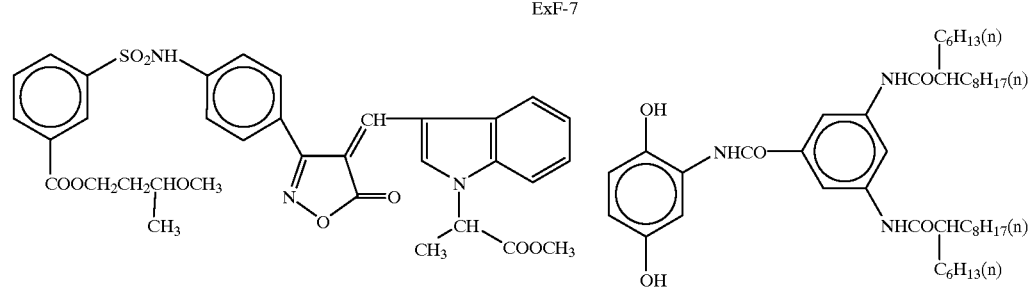
Cpd-2
Cpd-3
UV-1
UV-2
UV-3
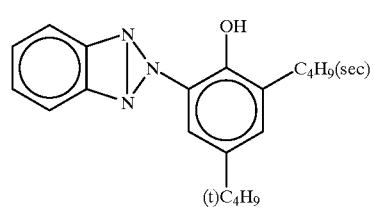
HBS-1
Tricresyl phosphate
HBS-2
Di-n-butyl phthalate

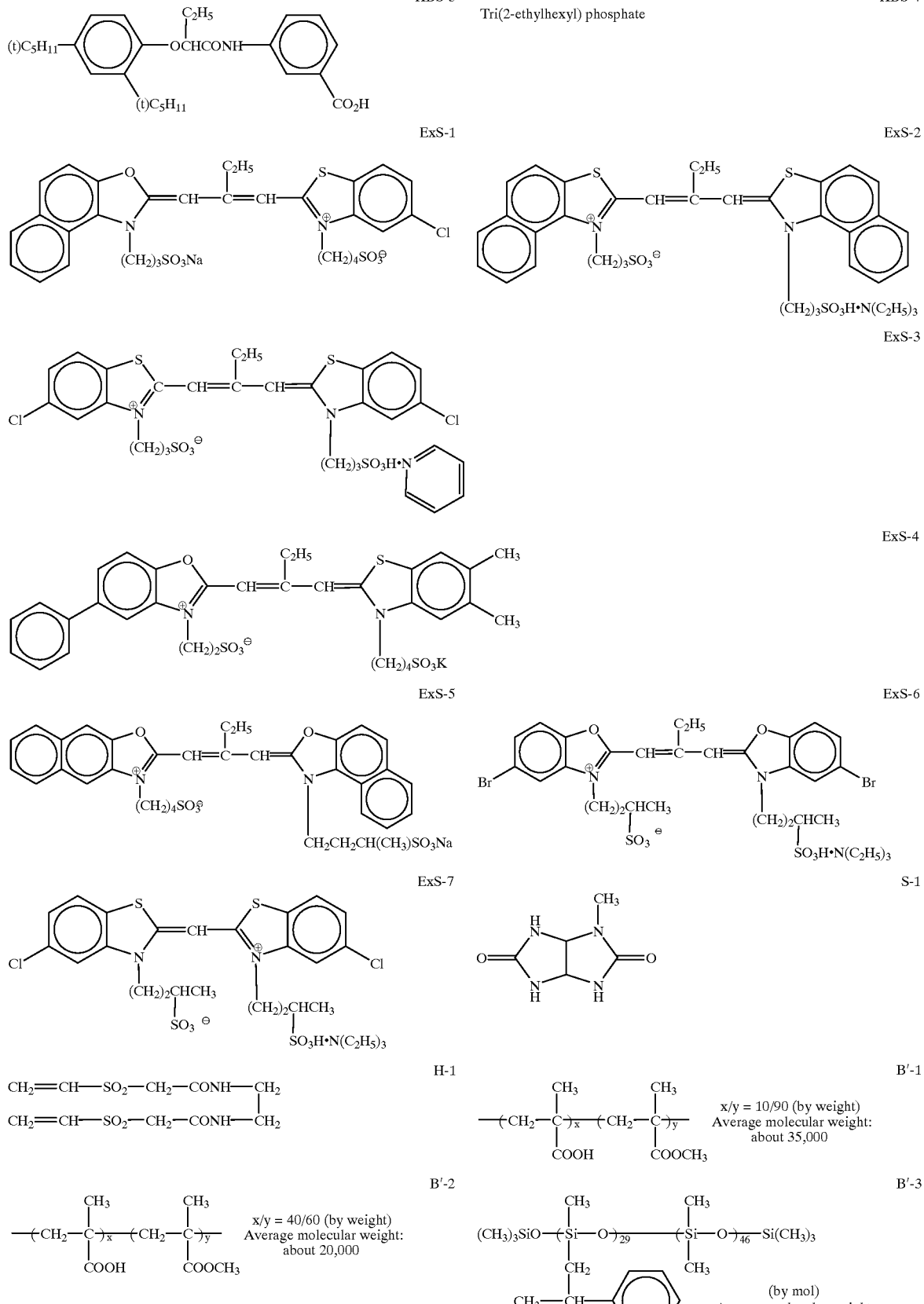

-continued
B'-4
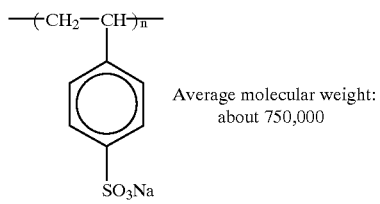
Average molecular weight: about 750,000
B'-5
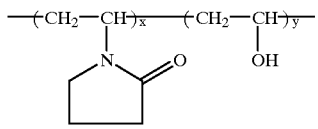
x/y = 70/30 (by weight)
Average molecular weight: about 17,000
B'-6
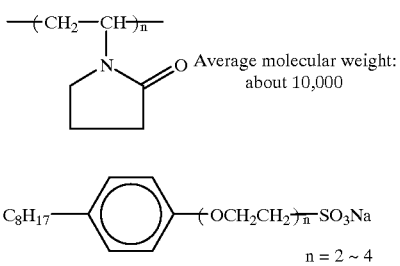
Average molecular weight: about 10,000
W-1
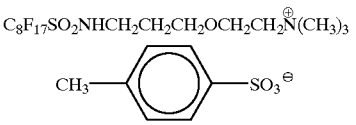
$C_8F_{17}SO_2NHCH_2CH_2CH_2OCH_2CH_2\overset{\oplus}{N}(CH_3)_3$
W-2
$C_8H_{17}$—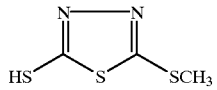—$(OCH_2CH_2)_n$—$SO_3Na$
n = 2 ~ 4
W-3
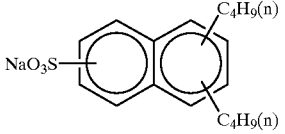
F-1
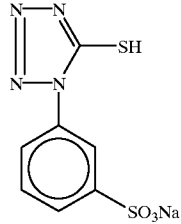
F-2
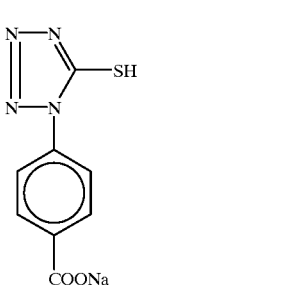
F-3
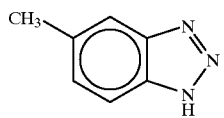
F-4
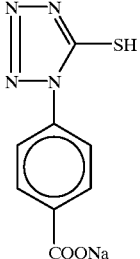
F-5
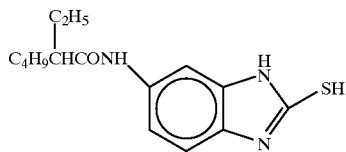
F-6
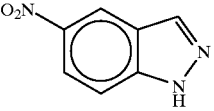
F-7
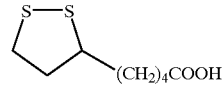
F-8
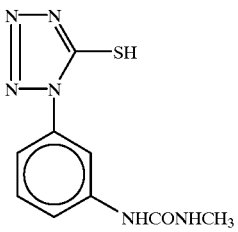
F-9
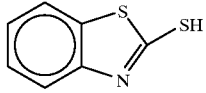
F-10
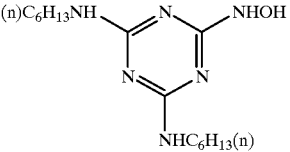

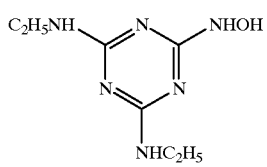
F-11

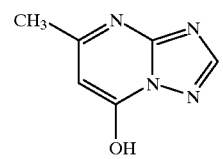
F-12

F-13

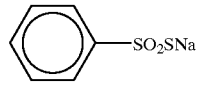
F-14

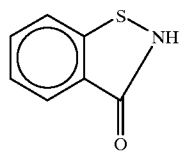
F-15

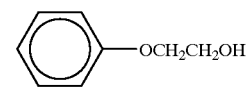
F-16

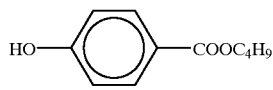
F-17

Each of the thus-prepared photographic material was cut into a size of 24 mm (width)×160 cm. At the portion 0.7 mm distant from one side width direction in the length direction of the photographic material, two perforations of 2 mm square were provided at a distance of 5.8 mm. A pair of two perforations was provided at a distance of 32 mm. Then, each film was housed in a plastic-made film cartridge described in FIGS. 1 to 7 of U.S. Pat. No. 5,296,887.

On each of these samples, FM signals were recorded from the magnetic recording layer-coated surface side between perforations at a feeding rate of 1,000/s using a head having a head gap of 5 μm and a turn number of 2,000 and capable of inputting/outputting.

After recording of FM signals, each sample was exposed to light of 1,000 cms uniformly throughout the emulsion surface and then processed by the following method. Thereafter, each sample was again housed in the film cartridge where it had been housed.

Sample 401 was cut into a width of 35 mm, used for photographing by a camera and processed in the following manner at a processing rate of 1 m²/day over 15 days (running processing).

Each processing was conducted as follows using an automatic developing machine FP-360B manufactured by Fuji Photo Film Co., Ltd. The machine was modified so that the overflow solution of the bleaching bath did not flow into the post-bath but all was discharged to the waste water tank. On this FP-360B, an evaporation correcting means described in *JIII Journal of Technical Disclosure*, No. 94-4992 was mounted.

The processing steps and the composition of each processing solution are described below.

| | (Processing Step) | | | |
|---|---|---|---|---|
| Step | Process-ing Time | Processing Temperature (° C.) | Replenish-ing Amount* (ml) | Tank Volume (l) |
| Color development | 3 min 5 sec | 38.0 | 20 | 17 |
| Bleaching | 50 sec | 38.0 | 5 | 5 |
| Fixing (1) | 50 sec | 38.0 | — | 5 |
| Fixing (2) | 50 sec | 38.0 | 8 | 5 |
| Water washing | 30 sec | 38.0 | 17 | 3.5 |
| Stabilization (1) | 20 sec | 38.0 | — | 3 |
| Stabilization (2) | 20 sec | 38.0 | 15 | 3 |
| Drying | 1 min 30 sec | 60 | | |

*Replenishing amount was per 1.1 m of the 35 mm-width photographic material (corresponding to 1 roll of 2 Ex.).

The stabilizing solution was in a countercurrent system of from (2) to (1) and the overflow solution of washing water was all introduced into the fixing (2). The fixing solution was also flown from (2) to (1) connected by countercurrent piping. The carried-over amounts of developer into the bleaching step, of bleaching solution into the fixing step, of fixing solution into the water washing step were 2.5 ml, 2.0 ml and 2.0 ml, respectively, per 1.1 m of the 35 mm-width photographic material. The cross-over time was 6 seconds in each interval and this time is included in the processing time of the previous step.

The open area of the above-described processing machine was 100 cm² for the color developer, 120 cm² for the bleaching solution and about 100 cm² for other processing solutions.

The composition of each processing solution is shown below.

| | Tank Solution (g) | Replenisher (g) |
|---|---|---|
| (Color Developer) | | |
| Diethylenetriaminepentaacetic acid | 2.0 | 2.0 |

-continued

|  | Tank Solution (g) | Replenisher (g) |
|---|---|---|
| 1-Hydroxyethylidene-1,1-diphosphonic acid | 2.0 | 2.0 |
| Sodium sulfite | 3.9 | 5.3 |
| Potassium carbonate | 37.5 | 39.0 |
| Potassium bromide | 1.4 | 0.4 |
| Potassium iodide | 1.3 mg | — |
| Disodium N,N-bis(2-sulfonato-ethyl)hydroxylamine | 2.0 | 2.0 |
| Hydroxylamine sulfate | 2.4 | 3.3 |
| 2-Methyl-4-[N-ethyl-N-(β-hydroxyethyl)amino]aniline sulfate | 4.5 | 6.4 |
| Water to make | 1.0 l | 1.0 l |
| pH (adjusted by potassium hydroxide and sulfuric acid) | 10.05 | 10.18 |
| (Bleaching Solution) | | |
| Ammonium 1,3-diamino-propanetetraacetato ferrate monohydrate | 118 | 180 |
| Ammonium bromide | 80 | 115 |
| Ammonium nitrate | 14 | 21 |
| Succinic acid | 40 | 60 |
| Maleic acid | 33 | 50 |
| Water to make | 1.0 l | 1.0 l |
| pH (adjusted by aqueous ammonia) | 4.4 | 4.0 |
| (Fixing Solution) | | |
| Ammonium methanesulfinate | 10 | 30 |
| Ammonium methanethiosulfonate | 4 | 12 |
| Aqueous solution of ammonium thiosulfate (700 g/l) | 280 ml | 840 ml |
| Imidazole | 7 | 20 |
| Ethylenediaminetetraacetic acid | 15 | 45 |
| Water to make | 1.0 l | 1.0 l |
| pH (adjusted by aqueous ammonia and acetic acid) | 7.4 | 7.45 |

Washing Water

Tap water was passed through a mixed bed column filled with an H-type strongly acidic cation exchange resin (Amberlite IR-120B, produced by Rhom and Haas) and an OH-type strongly basic anion exchange resin (Amberlite IR-400, produced by the same company) to reduce the calcium and magnesium ion concentrations each to 3 mg/l or less and then thereto 20 mg/l of sodium isocyanurate dichloride and 150 mg/l of sodium sulfate were added. The resulting solution had a pH of from 6.5 to 7.5.
Stabilizing Solution The tank solution and the replenisher were common.

|  | (unit: g) |
|---|---|
| Sodium p-toluenesulfinate | 0.03 |
| Polyoxyethylene-p-monononylphenyl ether (average polymerization degree: 10) | 0.2 |
| Disodium ethylenediaminetetraacetate | 0.05 |
| 1,2,4-Triazole | 1.3 |
| 1,4-Bis(1,2,4-triazol-1-ylmethyl)-piperazine | 0.75 |
| 1,2-Benzoisothiazolin-3-one | 0.10 |
| Water to make | 1.0 l |
| pH | 8.5 |

EXAMPLE 5

Samples were prepared by adding Compound A-1, A-4, A-16, A-23 or A-33 for use in the present invention in an amount of $1.5 \times 10^{-2}$ mol/mol-Ag to the fourth, fifth and sixth layers of Sample 101 in Example 1 of JP-A-6-118533. Each sample was exposed and then allowed to stand under forcedly deteriorating conditions of 50° C. and 60% for 7 days. Thereafter, each sample was subjected to color reversal processing described in JP-A-6-118533 (pages 37 and 38) and evaluated. As a result, the photographic materials to which the compound for use in the present invention was added, exhibited advantageous capability such that the increase in the sensitivity upon leaving after exposure was small and the reduction in the maximum color density was small, as compared with the photographic material to which the compound was not added.

EXAMPLE 6

Preparation of Emulsion A

To 1 l of water, 25 g of potassium bromide, 15 g of potassium iodide, 1.9 g of potassium thiocyanate and 24 g of gelatin were added. The vessel containing the mixture was kept at a temperature of 60° C. and thereto, an aqueous silver nitrate solution and an aqueous potassium bromide solution were added by a double jet method according to a usual ammonia method while vigorously stirring to thereby prepare a thick platy silver iodobromide emulsion having an iodide content of 10 mol % and an average grain size of 1.0 μm and relatively close to amorphous grain. Thereafter, the temperature was lowered to 35° C. and soluble salts were removed by a coagulation-flocculation method. Then, the temperature was elevated to 40° C., 82 g of gelatin was added and the pH and the pAg were adjusted to 6.40 and 8.80, respectively, by caustic soda and sodium bromide.

After elevating the temperature to 61° C., 0.95 g of 2-phenoxyethanol was added and further 213 mg of Sensitizing Dye-A shown below was added. After 10 minutes, 1.2 mg of sodium thiosulfate pentahydrate, 28 mg of potassium thiocyanate and 0.4 mg of chloroauric acid were added and after 65 minutes, the mixture was rapidly cooled and solidified.

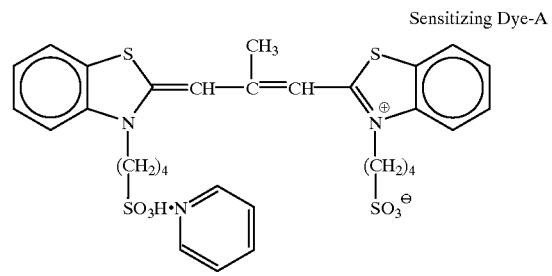

Sensitizing Dye-A

Preparation of Emulsion B

To 1 l of water, 25 g of potassium bromide, 9 g of potassium iodide, 7.6 g of potassium thiocyanate and 24 g of gelatin were added. The vessel containing the mixture was kept at a temperature of 40° C. and thereto, an aqueous silver nitrate solution and an aqueous potassium bromide solution were added by a double jet method according to a usual ammonia method while vigorously stirring to thereby prepare a thick platy silver iodobromide emulsion having an iodide content of 6 mol % and an average grain size of 0.6 μm and relatively close to amorphous grain. Thereafter, the temperature was lowered to 35° C. and soluble salts were removed by a coagulation-flocculation method. Then, the temperature was elevated to 40° C., 110 g of gelatin was added and the pH and the pAg were adjusted to 6.60 and 8.90, respectively, by caustic soda and sodium bromide. After elevating the temperature to 56° C., 0.8 mg of chloroauric acid, 9 mg of potassium thiocyanate and 4 mg of sodium thiosulfate were added. After 55 minutes, 180 mg of Dye-A was added. After 10 minutes, the mixture was rapidly cooled and solidified.

Preparation of Coated Samples

Coated Sample 601 was prepared according to the production method described in JP-A-62-115035 by coating the following layers on a triacetyl cellulose support of which emulsion coating surface was previously subbed and back surface was coated by:

| | |
|---|---|
| Compound-I | 60 mg/m² |
| Diacetyl cellulose | 143 mg/m² |
| Silicon oxide | 5 mg/m² |

Compound-I

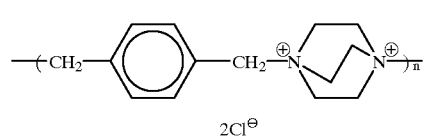

First Layer (antihalation layer)

| | |
|---|---|
| Gelatin | 1.0 g/m² |
| Compound-II | 140 mg/m² |
| Compound-III | 15 mg/m² |
| Dye-I | 26 mg/m² |
| Dye-II | 16 mg/m² |

Compound-II

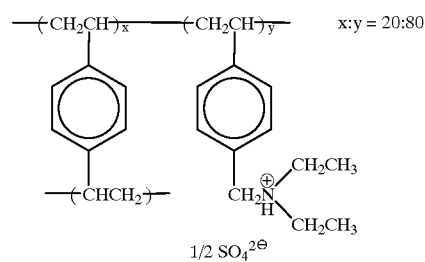

Compound-III

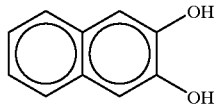

Dye-I

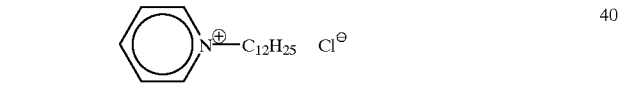

Dye-II

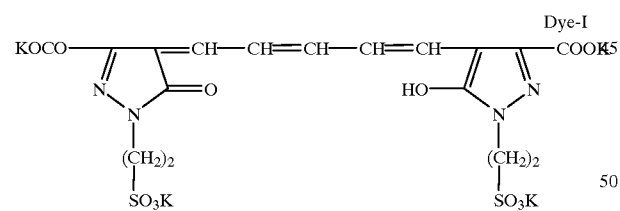

Second Layer (interlayer)

| | |
|---|---|
| Gelatin | 0.4 g/m² |
| Polypotassium-p-vinylbenzene sulfonate | 5 mg/m² |

Third Layer (emulsion layer)

| | |
|---|---|
| Emulsion B as silver | 1.36 g/m² |

-continued

| | |
|---|---|
| Gelatin | 2.0 g/m² |
| 4-Hydroxy-6-methyl-1,3,3a,7-tetraazaindene | 15 mg/m² |
| $C_{18}H_{35}O(CH_2CH_2O)_{25}H$ | 10 mg/m² |
| Compound-IV | 1.5 mg/m² |
| Polypotassium-p-vinylbenzene sulfonate | 50 mg/m² |
| Bis(vinylsulfonylacetamido)ethane | 65 mg/m² |

Compound-IV

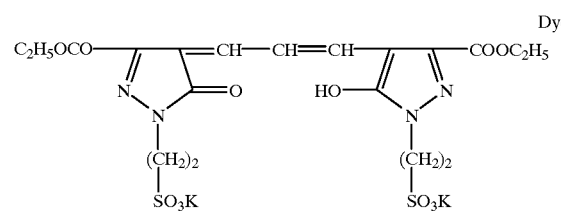

Fourth Layer (emulsion layer)

| | |
|---|---|
| Emulsion A as silver | 4.2 g/m² |
| Gelatin | 6.5 g/m² |
| Dextran (average molecular weight: 150,000) | 1.2 g/m² |
| 4-Hydroxy-6-methyl-1,3,3a,7-tetraazaindene | 41 mg/m² |
| $C_{18}H_{35}O(CH_2CH_2O)_{25}H$ | 23 mg/m² |
| Trimethylolpropane | 500 mg/m² |
| Polypotassium-p-vinylbenzene sulfonate | 88 mg/m² |
| Polyacrylic acid | 54 mg/m² |

Fifth Layer (surface protective layer)

| | |
|---|---|
| Gelatin | 0.8 g/m² |
| Compound-V | 13 mg/m² |
| Compound-VI | 50 mg/m² |
| Compound-VII | 1.8 mg/m² |
| Polypotassium-p-vinylbenzene sulfonate | 6 mg/m² |
| Polymethyl methacrylate fine particles (average particle size: 3 μm) | 24 mg/m² |
| Compound-VIII | 50 mg/m² |

Compound-V

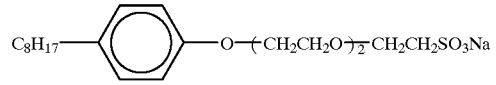

Compound-VI

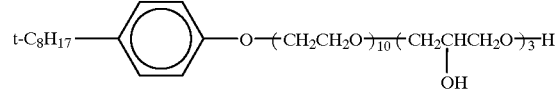

Compound-VII

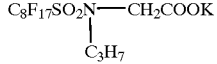

Compound-VIII

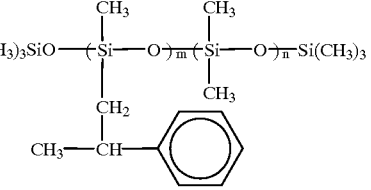

W-1

Solv-1

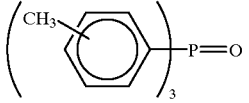

To 300 ml of ethyl acetate, 18.9 g of Compound A-1 for use in the present invention, 19.0 g of poly-t-butylacrylamido (molecular weight: 100,000), 9.5 g of high boiling point organic solvent (Solv-1) and 38.0 g of surface active agent (W-1) were added and dissolved under heating. The resulting solution was added to a 10% aqueous gelatin solution and emulsion-dispersed in a house-use mixer for 10 minutes.

The emulsified product obtained was added to the third and fourth layers of Sample 601 so that the coverage of Compound A-1 for use in the present invention could be 0.1 mol/mol-Ag, to thereby prepare Sample 603. Sample 602 was prepared by removing only Compound A-1 for use in the present invention from the emulsified product of Sample 603 and Sample 604 was prepared by using Compound A-33 in place of Compound A-1 for use in the present invention in Sample 603.

These samples were stored under temperature and humidity conditions of 30° C. and 65% RH for 14 days after the coating. Each sample was tested according to the following method.

(1) Measurement of Sensitivity

Each sample was exposed through an optical wedge for $1/100$ second using a tungsten light source having a color temperature of 2854 K of which color temperature was increased through a color temperature variation filter to 5400 K.

Then, each sample was subjected to development, fixing, water washing and drying in an automatic developing machine. The sensitivity of each sample is shown by a logarithm of the reciprocal of an exposure amount required to give an optical density 0.5 higher than the fog.

The development conditions are as follows.

| | Processing Solution | Temperature | Time |
|---|---|---|---|
| Development | HPD | 26.5° C. | 55 sec. |
| Fixing | Super Fujix DP2 | 26.5° C. | 76 sec. |
| Water washing | Flowing water | 20° C. | 95 sec. |
| Drying | | 50° C. | 69 sec. |

The aging stability of photographic property when the photographic material was allowed to stand after photographing was evaluated according to the following method.

Samples 601 to 604 were exposed by the above-described method and then allowed to stand under conditions of 50° C. and a 60% RH for 7 days. Then, each sample was processed and measured according to the method described above. The results are shown in Table 4 as a relative value to that of the sample processed immediately after exposure. The nearer to 0 the value is, the smaller the change due to aging is.

TABLE 4

| | | Aging Stability after Photographing | |
|---|---|---|---|
| Sample | Compound | Change in Sensitivity | Increase of Fog |
| 601 (Comparison) | — | +0.06 | 0.04 |
| 602 (Comparison) | — | +0.06 | 0.04 |
| 603 (Invention) | A-1 | +0.01 | 0.01 |
| 604 (Invention) | A-33 | +0.01 | 0.01 |

It is clearly seen from Table 4 that the photographic materials containing the compound for use in the present invention were outstandingly improved in the aging stability of the photographic property when they were left after photographing.

EXAMPLE 7

Sample 701 as a multi-layer color photographic material was prepared to have layers each having the following composition, on a cellulose triacetate film support subjected to undercoating.

Composition of Light-Sensitive Layer

The coating amounts are expressed, in the case of silver halide and colloid silver, by the unit of $g/m^2$ of silver, in the case of couplers, additives and gelatin, by the unit of $g/m^2$ and, in the case of sensitizing dyes, by molar number per mol of silver halide in the same layer. The symbols used for additives have the following meanings. When the additive has a plurality of effects, one of the effects is used as a representative.

| | |
|---|---|
| UV | ultraviolet absorbent, |
| Solv | high boiling point organic solvent |
| ExF | dye |
| ExS | sensitizing dye |
| ExC | cyan coupler |
| ExM | magenta coupler |
| ExY | yellow coupler |
| Cpd | additive |

First Layer (antihalation layer)

| | |
|---|---|
| Black colloidal silver | 0.15 |
| Gelatin | 2.33 |
| UV-1 | $1.9 \times 10^{-2}$ |
| UV-2 | $4.7 \times 10^{-2}$ |
| UV-3 | $8.6 \times 10^{-2}$ |
| ExF-3 | $5.0 \times 10^{-3}$ |
| ExM-3 | $2.3 \times 10^{-2}$ |
| Solv-1 | 0.16 |
| Solv-2 | 0.10 |

Second Layer (interlayer)

| | |
|---|---|
| Gelatin | 0.88 |
| Polyethylacrylate latex | $2.6 \times 10^{-1}$ |
| ExC-7 | $5.0 \times 10^{-2}$ |

Third Layer (low-sensitivity red-sensitive emulsion layer)

| | |
|---|---|
| Silver Iodobromide Emulsion A | as silver 0.24 |
| Silver Iodobromide Emulsion B | as silver 0.65 |
| Gelatin | 1.75 |
| ExS-1 | $6.9 \times 10^{-4}$ |
| ExS-2 | $4.0 \times 10^{-4}$ |
| ExS-5 | $6.7 \times 10^{-4}$ |
| ExS-7 | $1.4 \times 10^{-5}$ |
| ExC-1 | $3.0 \times 10^{-1}$ |
| ExC-5 | $2.0 \times 10^{-1}$ |
| ExC-9 | $2.2 \times 10^{-2}$ |
| Cpd-4 | $5.3 \times 10^{-2}$ |
| ExC-4 | $6.1 \times 10^{-2}$ |

Fourth Layer (medium-sensitivity red-sensitive emulsion layer)

| | |
|---|---|
| Silver Iodobromide Emulsion C | as silver 0.67 |
| Gelatin | 0.94 |
| ExS-1 | $3.5 \times 10^{-4}$ |
| ExS-2 | $2.0 \times 10^{-4}$ |
| ExS-5 | $3.4 \times 10^{-4}$ |
| ExS-7 | $6.9 \times 10^{-6}$ |
| ExC-1 | $1.3 \times 10^{-1}$ |
| ExC-4 | $4.6 \times 10^{-2}$ |
| ExC-5 | $8.6 \times 10^{-2}$ |
| ExC-6 | $1.1 \times 10^{-2}$ |
| ExC-7 | $4.6 \times 10^{-2}$ |
| Cpd-4 | $2.1 \times 10^{-2}$ |

Fifth Layer (high-sensitivity red-sensitive emulsion layer)

| | |
|---|---|
| Silver Iodobromide Emulsion D | as silver 0.67 |
| Gelatin | 0.68 |
| ExS-1 | $3.2 \times 10^{-4}$ |
| ExS-2 | $1.8 \times 10^{-4}$ |
| ExS-5 | $3.1 \times 10^{-4}$ |
| ExS-7 | $4.8 \times 10^{-5}$ |
| ExC-1 | $5.1 \times 10^{-2}$ |
| ExC-6 | $9.0 \times 10^{-3}$ |
| ExC-4 | $2.0 \times 10^{-2}$ |
| ExC-9 | $1.0 \times 10^{-2}$ |
| Cpd-4 | $2.1 \times 10^{-3}$ |
| Solv-1 | 0.08 |
| Solv-2 | 0.04 |

Sixth Layer (interlayer)

| | |
|---|---|
| Gelatin | 0.62 |
| Cpd-1 | 0.08 |
| Polyethylacrylate latex | $4.1 \times 10^{-2}$ |
| Solv-1 | $4.0 \times 10^{-2}$ |

Seventh Layer (low-sensitivity green-sensitive emulsion layer)

| | |
|---|---|
| Silver Iodobromide Emulsion E | as silver 0.14 |
| Gelatin | 0.49 |
| ExS-8 | $5.7 \times 10^{-5}$ |
| ExS-4 | $9.0 \times 10^{-4}$ |
| ExS-5 | $1.8 \times 10^{-4}$ |
| ExM-1 | 0.26 |
| Solv-1 | 0.15 |
| Solv-3 | $7.0 \times 10^{-3}$ |

Eighth Layer (medium-sensitivity green-sensitive emulsion layer)

| | |
|---|---|
| Silver Iodobromide Emulsion F | as silver 0.08 |
| Silver Iodobromide Emulsion E | as silver 0.01 |
| Gelatin | 0.14 |
| ExS-8 | $4.3 \times 10^{-5}$ |
| ExS-4 | $6.8 \times 10^{-4}$ |
| ExS-5 | $1.3 \times 10^{-4}$ |
| ExM-1 | $4.9 \times 10^{-2}$ |
| ExM-7 | $1.0 \times 10^{-2}$ |
| ExY-1 | $5.0 \times 10^{-3}$ |
| Solv-1 | $3.3 \times 10^{-2}$ |
| Solv-3 | $1.5 \times 10^{-3}$ |

Ninth Layer (high-sensitivity green-sensitive emulsion layer)

| | |
|---|---|
| Silver Iodobromide Emulsion G | as silver 0.60 |
| Gelatin | 0.60 |
| EXS-4 | $5.0 \times 10^{-4}$ |
| ExS-5 | $9.9 \times 10^{-5}$ |
| ExS-8 | $3.2 \times 10^{-5}$ |
| ExM-7 | $2.4 \times 10^{-2}$ |
| ExM-1 | $8.4 \times 10^{-2}$ |
| ExY-1 | $6.7 \times 10^{-2}$ |
| ExC-1 | $6.0 \times 10^{-3}$ |
| ExC-4 | $8.0 \times 10^{-3}$ |
| Cpd-6 | $8.0 \times 10^{-3}$ |
| Solv-1 | 0.12 |
| Solv-2 | 0.06 |
| Solv-3 | $6.0 \times 10^{-3}$ |

Tenth Layer (interlayer)

| | |
|---|---|
| Gelatin | 0.39 |
| UV-2 | $1.4 \times 10^{-2}$ |
| UV-3 | $1.6 \times 10^{-2}$ |
| UV-5 | $4.2 \times 10^{-2}$ |
| Cpd-1 | $2.6 \times 10^{-2}$ |
| Polyethylacrylate latex | $1.4 \times 10^{-2}$ |
| Solv-1 | $2.8 \times 10^{-2}$ |

Eleventh Layer (donor layer having interlayer effect to red-sensitive layer)

| | |
|---|---|
| Silver Iodobromide Emulsion H | as silver 1.12 |
| Silver Iodobromide Emulsion I | as silver 0.26 |
| Gelatin | 1.61 |
| ExS-3 | $6.4 \times 10^{-4}$ |
| ExM-2 | $2.7 \times 10^{-2}$ |
| ExM-1 | $2.0 \times 10^{-1}$ |
| ExM-7 | $1.7 \times 10^{-1}$ |
| ExY-2 | $2.0 \times 10^{-1}$ |
| Solv-1 | 0.50 |

Twelfth Layer (yellow filter layer)

| | |
|---|---|
| Yellow colloidal silver | $3.3 \times 10^{-2}$ |
| Gelatin | 0.61 |
| Cpd-1 | $4.3 \times 10^{-2}$ |
| Cpd-2 | $7.9 \times 10^{-2}$ |
| Cpd-5 | $1.0 \times 10^{-3}$ |
| Solv-1 | $4.7 \times 10^{-2}$ |

Thirteenth Layer (low-sensitivity blue-sensitive emulsion layer)

| | |
|---|---|
| Silver Iodobromide Emulsion J | as silver 0.62 |
| Gelatin | 1.67 |
| ExS-9 | $8.8 \times 10^{-4}$ |
| ExY-2 | $1.2 \times 10^{-1}$ |
| ExY-3 | $5.5 \times 10^{-1}$ |
| ExC-9 | $6.3 \times 10^{-2}$ |
| ExY-7 | $2 \times 10^{-2}$ |
| ExY-8 | $1 \times 10^{-2}$ |
| ExC-1 | $3.0 \times 10^{-2}$ |
| ExC-10 | $8.4 \times 10^{-2}$ |
| Solv-1 | 0.33 |

Fourteenth Layer (high-sensitivity blue-sensitive emulsion layer)

| | |
|---|---|
| Silver Iodobromide Emulsion K | as silver 0.14 |
| Silver Iodobromide Emulsion L | as silver 0.10 |
| Silver Iodobromide Emulsion M | as silver 0.22 |
| Gelatin | 1.00 |
| ExS-6 | $4.4 \times 10^{-4}$ |
| ExY-2 | $7.6 \times 10^{-2}$ |
| ExY-3 | $1.1 \times 10^{-1}$ |
| ExY-6 | $3.1 \times 10^{-1}$ |
| ExY-8 | $4 \times 10^{-2}$ |
| ExC-1 | $1.8 \times 10^{-2}$ |
| ExC-10 | $2.3 \times 10^{-2}$ |
| Solv-1 | $1.7 \times 10^{-1}$ |

Fifteenth Layer (first protective layer)

| | |
|---|---|
| Fine Grain Silver Iodobromide Emulsion N | as silver 0.06 |
| Gelatin | 0.51 |
| UV-2 | $4.0 \times 10^{-2}$ |
| UV-3 | $4.9 \times 10^{-2}$ |
| UV-5 | 0.12 |
| Cpd-3 | 0.10 |
| ExF-4 | $2.1 \times 10^{-3}$ |
| ExF-5 | $6.3 \times 10^{-3}$ |
| Solv-4 | $2.0 \times 10^{-2}$ |
| Polyethylacrylate latex | $9.0 \times 10^{-2}$ |

Sixteenth Layer (second protective layer)

| | |
|---|---|
| Fine Grain Silver Iodobromide Emulsion N | as silver 0.18 |
| Gelatin | 0.84 |
| B'-1 (diameter: 2.0 μm) | $8.0 \times 10^{-2}$ |
| B'-2 (diameter: 2.0 μm) | $8.0 \times 10^{-2}$ |
| B'-3 | $3.5 \times 10^{-2}$ |
| W-5 | $1.8 \times 10^{-2}$ |
| H-1 | 0.18 |

To the thus-prepared sample, 1,2-benzoisothiazolin-3-one (200 ppm on average to gelatin), n-butyl-p-hydroxybenzoate (about 1,000 ppm on average to gelatin) and 2-phenoxyethanol (about 10,000 ppm on average to gelatin) were additionally added. Further, in order to provide good preservability, processability, pressure durability, antimold/ bactericidal property, antistatic property and coatability, W-1, W-2, W-3, W-4, W-5, W-6, B'-1, B'-2, B'-3, B'-4, B'-5, B'-6, F-1, F-2, F-3, F-4, F-5, F-6, F-7, F-8, F-9, F-10, F-11, F-12, F-13, F-14, F-15, F-16, F-17, iron salt, lead salt, gold salt, platinum salt, iridium salt or rhodium salt was appropriately added to each layer.

Emulsions A to N used in Sample 701 were the same as Emulsions A to N used in Sample 101 of Example 1.

The chemical formulae of additives used in Sample 701 were the same as the chemical formulae of additives used in Sample 101 of Example 1.

To the fourth layer of Sample 701, the compound represented by formula (IB) or a comparative compound, coemulsified with the coupler in this layer, was added to give the coated amount of $5\times10^{-2}$ mol per mol of Ag in this layer. With respect to other conditions, the preparation method of Sample 701 was followed to prepare other samples as shown in Table 6.

Evaluation on the fluctuation in the photographic property after photographing until processing was performed in the following manner.

Each photographic material sample was exposed for sensitometry, stored for 3 days under forcedly deteriorating conditions of 60° C. and 60% or of 50° C. and 80%, and then subjected to the following color development processing at 38° C. The processed samples were measured on the density through a red filter and a blue filter. The degree of difference in the sensitivity between these samples and the sample subjected to development processing immediately after exposure was evaluated.

Compound A

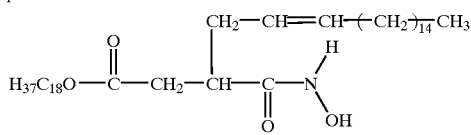

Compound B (compound described in U.S. Pat. No. 4,339,515)

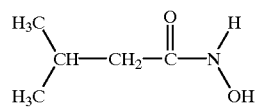

Compound C (Compound 38 described in U.S. Pat. No. 4,330,606)

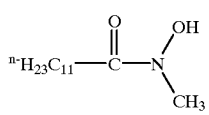

Compound D (compound described in JP-A-3-293666)

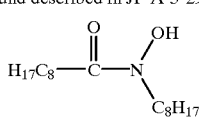

Compound E (compound described in JP-A-59-198453)

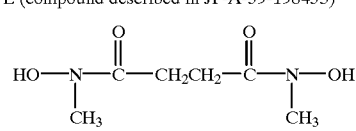

Each of the color photographic materials was exposed as above and then processed according to the following method.

| Processing Method | | |
|---|---|---|
| Step | Processing Time | Processing Temperature (° C.) |
| Color development | 3 min. 15 sec. | 38 |
| Bleaching | 3 min. 00 sec. | 38 |
| Water washing | 30 sec. | 24 |

| -continued | | |
|---|---|---|
| Processing Method | | |
| Fixing | 3 min. 00 sec. | 38 |
| Water washing (1) | 30 sec. | 24 |
| Water washing (2) | 30 sec. | 24 |
| Stabilization | 30 sec. | 38 |
| Drying | 4 min. 20 sec. | 55 |

The composition of each processing solution is shown below.

| | (unit: g) |
|---|---|
| (Color Developer) | |
| Diethylenetriaminepentaacetic acid | 1.0 |
| 1-Hydroxyethylidene-1,1-diphosphonic acid | 2.0 |
| Sodium sulfite | 4.0 |
| Potassium carbonate | 30.0 |
| Potassium bromide | 1.4 |
| Potassium iodide | 1.5 mg |
| Hydroxylamine sulfate | 2.4 |
| 4-[N-Ethyl-N-(β-hydroxyethyl)amino]-2-methylaniline sulfate | 4.5 |
| Water to make | 1.0 liter |
| pH (adjusted by potassium hydroxide and sulfuric acid) | 10.05 |
| (Bleaching Solution) | |
| N-(2-Carboxyphenyl)iminodiacetato ferrate pentahydrate | 25.0 |
| Ammonium 1,3-diaminopropanetetraacetato ferrate dihydrate | 25.0 |
| 1,3-Diaminopropanetetraacetic acid | 2.0 |
| Malonic acid | 7.0 |
| Succinic acid | 60.0 |
| Glutaric acid | 15.0 |
| Sodium bromide | 40.0 |
| Sodium nitrate | 30.0 |
| Sodium hydroxide | 30.0 |
| Diethanolamine | 20.0 |
| Water to make | 1.0 liter |
| pH (adjusted by sodium hydroxide and nitric acid) | 4.2 |
| (Fixing Solution) | |
| 1,3-Diaminopropanetetraacetic acid | 6.0 |
| Ammonium sulfite | 20.0 |
| Ammonium thiosulfate (aq. soln. 750 g/l) | 270.0 ml |
| Acetic acid (90%) | 5.0 |
| Water to make | 1.0 liter |
| pH (adjusted by aqueous ammonia and acetic acid) | 6.4 |
| (Stabilizing Solution) | |
| p-Nonylphenoxypolyglycidol (glycidol average polymerization degree: 10) | 0.2 |
| Ethylenediaminetetraacetic acid | 0.05 |
| 1,2,4-Triazole | 1.3 |
| 1,4-Bis(1,2,4-triazol-1-ylmethyl)-piperazine | 0.75 |
| Hydroxyacetic acid | 0.02 |
| Hydroxyethyl cellulose (HEC SP-2000, produced by Daicel Chemical KK) | 0.1 |
| 1,2-Benzoisothiazolin-3-one | 0.05 |
| Water to make | 1.0 liter |
| pH | 8.5 |

The sensitivity as a photographic property is shown by a logarithm of the reciprocal of an exposure amount required to give an optical density 1.0 higher than the fog. The fluctuation in the photographic property after photographing until processing is shown by a relative sensitivity (difference in logarithms) of the sensitivity of photographic materials stored after exposure under forcedly deteriorating conditions to the sensitivity of the photographic material processed immediately after exposure. The nearer to 0 the value is, the smaller the fluctuation in the photographic property is and the more preferable the material is.

Fluctuation in the photographic property both of the red-sensitive layer to which the compound of formula (IB) was added and of the blue-sensitive layer to which the compound was not added was evaluated. When the compound of formula (IB) or a comparative compound was added, the photographic property of the blue-sensitive layer changed as compared with the material Sample 701) to which, the compound was not added. This reveals that the compound disadvantageously diffused from the red-sensitive layer (layer to which the compound was added) to the blue-sensitive layer (layer to which the compound was not added).

The results are shown in Table 5.

TABLE 5

| Sample | Compound | Fluctuation in Photographic Property due to Aging after Photographing until Processing | |
|---|---|---|---|
| | | Red-Sensitive Layer 60° C., 60% | Blue-Sensitive Layer 60° C., 60% |
| 701 (Comparison) | — | 0.20 | −0.02 |
| 702 (Comparison) | A | 0.19 | −0.01 |
| 703 (Comparison) | B | 0.20 | −0.02 |
| 704 (Comparison) | C | 0.14 | −0.03 |
| 705 (Comparison) | D | 0.14 | −0.02 |
| 706 (Comparison) | E | 0.08 | −0.05 |
| 707 (Invention) | B-1 | 0.04 | −0.02 |
| 708 (Invention) | B-2 | 0.03 | −0.02 |
| 709 (Invention) | B-6 | 0.03 | −0.02 |
| 710 (Invention) | B-7 | 0.05 | −0.02 |
| 711 (Invention) | B-11 | 0.03 | −0.02 |
| 712 (Invention) | B-18 | 0.03 | −0.02 |
| 713 (Invention) | B-25 | 0.03 | −0.02 |
| 714 (Invention) | B-31 | 0.04 | −0.02 |
| 715 (Invention) | B-38 | 0.05 | −0.02 |
| 716 (Invention) | B-40 | 0.01 | −0.02 |
| 717 (Invention) | B-51 | 0.02 | −0.02 |
| 718 (Invention) | B-42 | 0.01 | −0.02 |
| 719 (Invention) | B-44 | 0.02 | −0.02 |

As clearly seen from Table 5, the photographic materials using the compound of formula (IB) for use in the present invention showed good results such that fluctuation in the photographic property due to aging after photographing until processing of the layer to which the compound was added (red-sensitive layer) was small and at the same time, fluctuation due to aging of the layer to which the compound was not added (blue-sensitive layer) was not worsened.

The compound of formula (IB) for use in the present invention affected neither other photographic properties nor storability of the layer to which the compound was not added.

EXAMPLE 8

Other than the compounds shown in Table 5 of Example 7, using Compound B-3, B-4, B-5, B-8, B-9, B-10, B-12, B-13, B-14, B-15, B-16, B-17, B-19, B-20, B-21, B-22, B-23, B-24, B-26, B-27, B-28, B-29, B-30, B-32, B-33, B-34, B-35, B-36 or B-37 for use in the present invention, evaluation was conducted. As a result, these compounds provided advantageous results such the the change in the photographic property due to aging was reduced when the materials were allowed to stand after photographing.

EXAMPLE 9

When the compound for use in the present invention was used in the green-sensitive layer or the blue-sensitive layer, similarly to Example 7, good results were provided such that the storability of the layer to which the compound was added was improved and the layer to which the compound was not added was not affected.

EXAMPLE 10

1) Support

The support used in this example was prepared in the same manner as in Example 4.

2) Coating of Undercoat Layer

The support obtained above was subjected to discharge treatments, coated by an undercoating solution and dried, in the same manner as in Example 4.

3) Coating of Back Layer

On one surface of the undercoated support, an antistatic layer, a magnetic recording layer and a slipping layer were coated as a back layer in the same manner as in Example 4. The slipping layer had the same property as that of Example 4.

4) Coating of Light-Sensitive Layer

The layers each having the following composition were coated to overlay one on another on the side of a support opposite to the back layer provided above to prepare a color negative film. This film was designated as Sample 1001.

Composition of Light-Sensitive Layer

The main materials used in each layer are classified as follows.

| | |
|---|---|
| ExC | cyan coupler |
| ExM | magenta coupler |
| ExY | yellow coupler |
| ExS | sensitizing dye |
| UV | ultraviolet absorbent |
| HBS | high-boiling point organic solvent |
| H | gelatin hardening agent |

Numerals corresponding to respective components show coating amounts expressed by the unit of $g/m^2$ and in case of silver halide, they show coating amounts in terms of silver. With respect to sensitizing dyes, the coating amount is shown by the unit mol per mol of silver halide in the same layer.

| First Layer (antihalation layer) | |
|---|---|
| Black colloidal silver | as silver 0.09 |
| Gelatin | 1.60 |
| ExM-1 | 0.12 |
| ExF-1 | $2.0 \times 10^{-3}$ |
| Solid Disperse Dye ExF-2 | 0.030 |
| Solid Disperse Dye ExF-3 | 0.040 |
| HBS-1 | 0.15 |
| HBS-2 | 0.02 |
| Second Layer (interlayer) | |
| Silver Iodobromide Emulsion M | as silver 0.065 |
| ExC-2 | 0.04 |
| Polyethylacrylate latex | 0.20 |
| Gelatin | 1.04 |
| Third Layer (low-sensitivity red-sensitive emulsion layer) | |
| Silver Iodobromide Emulsion A | as silver 0.30 |
| Silver Iodobromide Emulsion B | as silver 0.20 |
| ExS-1 | $6.9 \times 10^{-5}$ |
| ExS-2 | $1.8 \times 10^{-5}$ |
| ExS-3 | $3.1 \times 10^{-4}$ |
| ExC-1 | 0.17 |
| ExC-3 | 0.030 |

-continued

| | |
|---|---|
| ExC-4 | 0.10 |
| ExC-5 | 0.020 |
| ExC-6 | 0.010 |
| Cpd-2 | 0.025 |
| HBS-1 | 0.15 |
| Gelatin | 0.87 |

Fourth Layer (medium-sensitivity red-sensitive emulsion layer)

| | |
|---|---|
| Silver Iodobromide Emulsion C | as silver 0.70 |
| ExS-1 | $3.5 \times 10^{-4}$ |
| ExS-2 | $1.6 \times 10^{-5}$ |
| ExS-3 | $5.1 \times 10^{-4}$ |
| ExC-1 | 0.13 |
| ExC-2 | 0.060 |
| ExC-3 | 0.0070 |
| ExC-4 | 0.090 |
| ExC-5 | 0.015 |
| ExC-6 | 0.0070 |
| Cpd-2 | 0.023 |
| HBS-1 | 0.08 |
| Gelatin | 0.75 |

Fifth Layer (high-sensitivity red-sensitive emulsion layer)

| | |
|---|---|
| Silver Iodobromide Emulsion D | as silver 1.20 |
| ExS-1 | $2.4 \times 10^{-4}$ |
| ExS-2 | $1.0 \times 10^{-4}$ |
| ExS-3 | $3.4 \times 10^{-4}$ |
| ExC-1 | 0.10 |
| ExC-3 | 0.045 |
| ExC-6 | 0.020 |
| ExC-7 | 0.010 |
| Cpd-2 | 0.050 |
| HBS-1 | 0.22 |
| HBS-2 | 0 050 |
| Gelatin | 1.10 |

Sixth Layer (interlayer)

| | |
|---|---|
| Cpd-1 | 0.090 |
| Solid Disperse Dye ExF-4 | 0.030 |
| HBS-1 | 0.050 |
| Polyethylacrylate latex | 0.15 |
| Gelatin | 1.10 |

Seventh Layer (low-sensitivity green-sensitive emulsion layer)

| | |
|---|---|
| Silver Iodobromide Emulsion E | as silver 0.10 |
| Silver Iodobromide Emulsion F | as silver 0.15 |
| Silver Iodobromide Emulsion G | as silver 0.10 |
| ExS-4 | $3.0 \times 10^{-5}$ |
| ExS-5 | $2.1 \times 10^{-4}$ |
| ExS-6 | $8.0 \times 10^{-4}$ |
| ExM-2 | 0.33 |
| ExM-3 | 0.086 |
| ExY-1 | 0.015 |
| HBS-1 | 0.30 |
| HBS-3 | 0.010 |
| Gelatin | 0.73 |

Eighth Layer (medium-sensitivity green-sensitive emulsion layer)

| | |
|---|---|
| Silver Iodobromide Emulsion H | as silver 0.80 |
| ExS-4 | $3.2 \times 10^{-5}$ |
| ExS-5 | $2.2 \times 10^{-4}$ |
| ExS-6 | $8.4 \times 10^{-4}$ |
| ExC-8 | 0.010 |
| ExM-2 | 0.10 |
| ExM-3 | 0.025 |
| ExY-1 | 0.018 |
| ExY-4 | 0.010 |
| ExY-5 | 0.040 |
| HBS-1 | 0.10 |
| HBS-3 | $4.0 \times 10^{-3}$ |
| Gelatin | 0.80 |

Ninth Layer (high-sensitivity green-sensitive emulsion layer)

| | |
|---|---|
| Silver Iodobromide Emulsion I | as silver 1.25 |
| ExS-4 | $3.7 \times 10^{-5}$ |
| ExS-5 | $8.1 \times 10^{-5}$ |
| ExS-6 | $3.2 \times 10^{-4}$ |
| ExC-1 | 0.010 |
| ExM-1 | 0.020 |

-continued

| | |
|---|---|
| ExM-4 | 0.025 |
| ExM-5 | 0.040 |
| Cpd-3 | 0.040 |
| HBS-1 | 0.25 |
| Polyethylacrylate latex | 0.15 |
| Gelatin | 1.33 |

Tenth Layer (yellow filter layer)

| | |
|---|---|
| Yellow colloidal silver | as silver 0.015 |
| Cpd-1 | 0.16 |
| Solid Disperse Dye ExF-5 | 0.060 |
| Solid Disperse Dye ExF-6 | 0.060 |
| Oil-Soluble Dye ExF-7 | 0.010 |
| HBS-1 | 0.60 |
| Gelatin | 0.60 |

Eleventh Layer (low-sensitivity blue-sensitive emulsion layer)

| | |
|---|---|
| Silver Iodobromide Emulsion J | as silver 0.09 |
| Silver Iodobromide Emulsion K | as silver 0.09 |
| ExS-7 | $8.6 \times 10^{-4}$ |
| ExC-8 | $7.0 \times 10^{-3}$ |
| ExY-1 | 0.050 |
| ExY-2 | 0.12 |
| ExY-3 | 0.60 |
| ExY-4 | 0.020 |
| Cpd-2 | 0.10 |
| Cpd-3 | $4.0 \times 10^{-3}$ |
| HBS-1 | 0.20 |
| Gelatin | 1.20 |

Twelfth Layer (high-sensitivity blue-sensitive emulsion layer)

| | |
|---|---|
| Silver Iodobromide Emulsion L | as silver 1.00 |
| ExS-7 | $4.0 \times 10^{-4}$ |
| ExY-2 | 0.08 |
| ExY-3 | 0.12 |
| ExY-4 | 0.010 |
| Cpd-2 | 0.10 |
| Cpd-3 | $1.0 \times 10^{-3}$ |
| HBS-1 | 0.070 |
| Gelatin | 0.70 |

Thirteenth Layer (first protective layer)

| | |
|---|---|
| UV-1 | 0.19 |
| UV-2 | 0.075 |
| UV-3 | 0.065 |
| HBS-1 | $5.0 \times 10^{-2}$ |
| HBS-4 | $5.0 \times 10^{-2}$ |
| Gelatin | 1.8 |

Fourteenth Layer (second protective layer)

| | |
|---|---|
| Silver Iodobromide Emulsion M | as silver 0.10 |
| H-1 | 0.40 |
| B'-1 (diameter: 1.7 μm) | $5.0 \times 10^{-2}$ |
| B'-2 (diameter: 1.7 μm) | 0.15 |
| B'-3 | 0.05 |
| S-1 | 0.20 |
| Gelatin | 0.70 |

Further, in order to provide good preservability, processability, pressure durability, antimold/bactericidal property, antistatic property and coatability, W-1, W-2, W-3, B'-4, B'-5, B'-6, F-1, F-2, F-3, F-4, F-5, F-6, F-7, F-8, F-9, F-10, F-11, F-12, F-13, F-14, F-15, F-16, F-17, iron salt, lead salt, gold salt, platinum salt, palladium salt, iridium salt or rhodium salt was appropriately added to each layer.

Emulsions A to M used in Sample 1001 were the same as Emulsions A to M used in Sample 401 of Example 4.

Preparation of Dispersion Product of Organic Solid Disperse Dye

Solid Disperse Dye ExF-2 was dispersed in the same manner as in Example 4.

Solid dispersion products of ExF-3, ExF-4 and ExF-6 each was obtained in the same manner. The average particle size of dye fine particles was 0.24, 0.45 or 0.52 μm, respectively. ExF-5 was dispersed by the microprecipitation dispersion method described in Example 1 of EP-A-549489. The average particle size was 0.06 μm.

The chemical formulae of additives used in Sample 1001 were the same as the chemical formulae of additives used in Sample 401 of Example 4.

Each of the thus-prepared photographic material was cut into a size of 24 mm (width)×160 cm. At the portion 0.7 mm distant from one side width direction in the length direction of the photographic material, two perforations of 2 mm square were provided at a distance of 5.8 mm. A pair of two perforations was provided at a distance of 32 mm. Then, each film was housed in a plastic-made film cartridge described in FIGS. 1 to 7 of U.S. Pat. No. 5,296,887.

On each of these samples, FM signals were recorded from the magnetic recording layer-coated surface side between perforations at a feeding rate of 1,000/s using a head having head gap of 5 μm and a turn number of 2,000 and capable of inputting/outputting.

After recording of FM signals, each sample was exposed to light of 1,000 cms uniformly throughout the emulsion surface and then processed by the following method. Thereafter, each sample was again housed in the film cartridge where it had been housed.

Sample 1001 was cut into a width of 35 mm, used for photographing by a camera and processed in the following manner at a processing rate of 1 m²/day over 15 days (running processing).

Each processing was conducted as follows using an automatic developing machine FP-360B manufactured by Fuji Photo Film Co., Ltd. The machine was modified so that the overflow solution of the bleaching bath did not flow into the post-bath but all was discharged to the waste water tank. On this FP-360B, an evaporation correcting means described in *JIII Journal of Technical Disclosure*, No. 94-4992 was mounted.

The processing steps and the composition of each processing solution are described below.

| Step | (Processing Step) Processing Time | Processing Temperature (° C.) | Replenishing Amount* (ml) | Tank Volume (l) |
|---|---|---|---|---|
| Color development | 3 min 5 sec | 38.0 | 20 | 17 |
| Bleaching | 50 sec | 38.0 | 5 | 5 |
| Fixing (1) | 50 sec | 38.0 | — | 5 |
| Fixing (2) | 50 sec | 38.0 | 8 | 5 |
| Water washing | 30 sec | 38.0 | 17 | 3.5 |
| Stabilizing (1) | 20 sec | 38.0 | — | 3 |
| Stabilizing (2) | 20 sec | 38.0 | 15 | 3 |
| Drying | 1 min 30 sec | 60 | | |

*Replenishing amount was per 1.1 m of the 35 mm-width photographic material (corresponding to 1 roll of 24 Ex.).

The stabilizing solution was in a countercurrent system of from (2) to (1) and the overflow solution of washing water was all introduced into the fixing (2). The fixing solution was also flown from (2) to (1) connected by countercurrent piping. The carried-over amounts of developer into the bleaching step, of bleaching solution into the fixing step, of fixing solution into the water washing step were 2.5 ml, 2.0 ml and 2.0 ml, respectively, per 1.1 m of the 35 mm-width photographic material. The cross-over time was 6 seconds in each interval and this time is included in the processing time of the previous step.

The open area of the above-described processing machine was 100 cm² for the color developer, 120 cm² for the bleaching solution and about 100 cm² for other processing solutions.

The composition of each processing solution is shown below.

| | Tank Solution (g) | Replenisher (g) |
|---|---|---|
| (Color Developer) | | |
| Diethylenetriaminepentaacetic acid | 2.0 | 2.0 |
| 1-Hydroxyethylidene-1,1-diphosphonic acid | 2.0 | 2.0 |
| Sodium sulfite | 3.9 | 5.3 |
| Potassium carbonate | 37.5 | 39.0 |
| Potassium bromide | 1.4 | 0.4 |
| Potassium iodide | 1.3 mg | — |
| Disodium N,N-bis(2-sulfonato-ethyl)hydroxylamine | 2.0 | 2.0 |
| Hydroxylamine sulfate | 2.4 | 3.3 |
| 2-Methyl-4-[N-ethyl-N-(β-hydroxyethyl)amino]aniline sulfate | 4.5 | 6.4 |
| Water to make | 1.0 l | 1.0 l |
| pH (adjusted by potassium hydroxide and sulfuric acid) | 10.05 | 10.18 |
| (Bleaching Solution) | | |
| Ammonium 1,3-diamino-propanetetraacetato ferrate monohydrate | 118 | 180 |
| Ammonium bromide | 80 | 115 |
| Ammonium nitrate | 14 | 21 |
| Succinic acid | 40 | 60 |
| Maleic acid | 33 | 50 |
| Water to make | 1.0 l | 1.0 l |
| pH (adjusted by aqueous ammonia) | 4.4 | 4.0 |
| (Fixing Solution) | | |
| Ammonium methanesulfinate | 10 | 30 |
| Ammonium methanethiosulfonate | 4 | 12 |
| Aqueous solution of ammonium thiosulfate (700 g/l) | 280 ml | 840 ml |
| Imidazole | 7 | 20 |
| Ethylenediaminetetraacetic acid | 15 | 45 |
| Water to make | 1.0 l | 1.0 l |
| pH (adjusted by aqueous ammonia and acetic acid) | 7.4 | 7.45 |

Washing Water

Tap water was passed through a mixed bed column filled with an H-type strongly acidic cation exchange resin (Amberlite IR-120B, produced by Rhom and Haas) and an OH-type strongly basic anion exchange resin (Amberlite IR-400, produced by the same company) to reduce the calcium and magnesium ion concentrations each to 3 mg/l or less and then thereto 20 mg/l of sodium isocyanurate dichloride and 150 mg/l of sodium sulfate were added. The resulting solution had a pH of from 6.5 to 7.5.

| (Stabilizing Solution) The tank solution and the replenisher were common. | |
|---|---|
| | (unit: g) |
| Sodium p-toluenesulfinate | 0.03 |
| Polyoxyethylene-p-monononylphenyl ether (average polymerization degree: 10) | 0.2 |
| Disodium ethylenediaminetetraacetate | 0.05 |
| 1,2,4-Triazole | 1.3 |
| 1,4-Bis(1,2,4-triazol-1-ylmethyl)-piperazine | 0.75 |
| 1,2-Benzoisothiazolin-3-one | 0.10 |

-continued (Stabilizing Solution)
The tank solution and the replenisher were common.

|  | (unit: g) |
|---|---|
| Water to make | 1.0 l |
| pH | 8.5 |

Evaluation was conducted by adding Compound B-1, B-2, B-3, B-7, B-11, B-16 or B-40 for use in the present invention to the red-sensitive layer. In samples where the compound for use in the present invention was added, the fluctuation in the photographic property was small between the sample processed immediately after exposure and the samples stored under forcedly deteriorating conditions, as compared with the sample where the compound was not added (Sample 1001).

Further, there was no difference in the change in the photographic property of the red-sensitive layer between samples where the compound for use in the present invention was added and the sample where the compound for use in the present invention was not added.

Also, when the compound for use in the present invention was added to the green-sensitive layer, an excellent effect was provided on the improvement of storability after exposure.

EXAMPLE 11

Samples were prepared by adding Compound B-4, B-27 or B-28 for use in the present invention in an amount of $5 \times 10^{-2}$ mol/mol-Ag to the fourth, fifth and sixth layers of Sample 701 in Example 7 of JP-A-6-118533. Each sample was exposed and then allowed to stand under forcedly deteriorating conditions of 50° C. and 60% for 7 days. Thereafter, each sample was subjected to color reversal processing described in JP-A-6-118533 (pages 37 and 38) and evaluated. As a result, the photographic materials to which the compound for use in the present invention was added, exhibited advantageous capability such that the increase in the sensitivity upon leaving after exposure was small and the reduction in the maximum color density was small, as compared with the photographic material to which the compound was not added.

EXAMPLE 12

Preparation of Emulsion A

Emulsion A was prepared in the same manner as in Example 6.

Preparation of Emulsion B

Emulsion B was prepared in the same manner as in Example 6.

Preparation of Coated Samples

Coated Sample 1201 was prepared in the same manner as Coated Sample 601 in Example 6.

To 300 ml of ethyl acetate, 18.9 g of Compound B-4 for use in the present invention, 19.0 g of poly-t-butylacrylamido (molecular weight: 100,000), 9.5 g of high boiling point organic solvent (Solv-1) and 38.0 g of surface active agent (W-1) were added and dissolved under heating. The resulting solution was added to a 10% aqueous gelatin solution and emulsion-dispersed in a house-use mixer for 10 minutes.

The emulsified product obtained was added to the third and fourth layers of Sample 1201 so that the coverage of Compound B-4 for use in the present invention could be 0.1 mol/mol-Ag, to thereby prepare Sample 1203. Sample 1202 was prepared by removing only Compound B-4 for use in the present invention from the emulsified product of Sample 1203 and Sample 1204 was prepared by using Compound B-27 in place of Compound B-4 for use in the present invention in Sample 1203.

These samples were stored under temperature and humidity conditions of 30° C. and 65% RH for 14 days after the coating. Each sample was tested according to the following method.

(1) Measurement of Sensitivity

Each sample was exposed through an optical wedge for $\frac{1}{100}$ second using a tungsten light source having a color temperature of 2854 K of which color temperature was increased through a color temperature variation filter to 5400 K.

Then, each sample was subjected to development, fixing, water washing and drying in an automatic developing machine. The sensitivity of each sample is shown by a logarithm of the reciprocal of an exposure amount required to give an optical density 0.5 higher than the fog.

The development conditions are as follows.

|  | Processing Solution | Temperature | Time |
|---|---|---|---|
| Development | HPD | 26.5° C. | 55 sec. |
| Fixing | Super Fujix DP2 | 26.5° C. | 76 sec. |
| Water washing | Flowing water | 20° C. | 95 sec. |
| Drying |  | 50° C. | 69 sec. |

The aging stability of photographic property when the photographic material was allowed to stand after photographing was evaluated according to the following method.

Samples 1201 to 1204 were exposed by the above-described method and then allowed to stand under conditions of 50° C. and 60% for 7 days. Then, each sample was processed and measured according to the method described above. The results are shown in Table 6 as a relative value to that of the sample processed immediately after exposure. The nearer to 0 the value is, the smaller the change due to aging is.

TABLE 6

|  |  | Aging Stability after Photographing | |
|---|---|---|---|
| Sample | Compound | Change in Sensitivity | Increase of Fog |
| 1201 (Comparison) | — | +0.09 | 0.05 |
| 1202 (Comparison) | — | +0.08 | 0.06 |
| 1203 (Invention) | B-4 | +0.01 | 0.03 |
| 1204 (Invention) | B-27 | +0.02 | 0.02 |

It is clearly seen from Table 6 that the photographic materials containing the compound for use in the present invention were outstandingly improved in the aging stability of the photographic property when they were left after photographing.

While the invention has been described in detail and with reference to specific embodiments thereof, it will be apparent to one skilled in the art that various changes and modifications can be made therein without departing from the spirit and scope thereof.

What is claimed is:

1. A compound represented by formula (IVA):

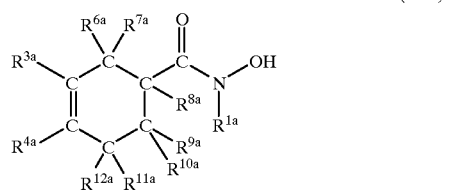

wherein $R^{1a}$ represents a hydrogen atom, a substituted or unsubstituted alkyl group having from 1 to 20 carbon atoms or a substituted or unsubstituted alkenyl group having from 2 to 20 carbon atoms;

$R^{3a}$ and $R^{4a}$, which may be the same or different, each represents an alkyl group having from 1 to 22 carbon atoms, an aryl group having from 6 to 20 carbon atoms, an alkenyl group having from 3 to 22 carbon atoms, a carboxyl group, a cyano group, an acyl group having from 2 to 20 carbon atoms, an aminocarbonyl group having from 1 to 37 carbon atoms, an alkoxycarbonyl group having from 2 to 20 carbon atoms, an aryloxycarbonyl group having from 7 to 20 carbon atoms or a heterocyclic group having from 3 to 20 carbon atoms;

$R^{6a}$, $R^{7a}$, $R^{8a}$, $R^{9a}$, $R^{10a}$, $R^{11a}$ and $R^{12a}$, which may be the same or different, each represents a hydrogen atom, an alkyl group having from 1 to 20 carbon atoms, an alkoxycarbonyl group having from 2 to 30 carbon atoms, an aminocarbonyl group having from 1 to 30 carbon atoms or an aryloxycarbonyl group having from 7 to 30 carbon atoms.

2. A compound represented by formula (VA):

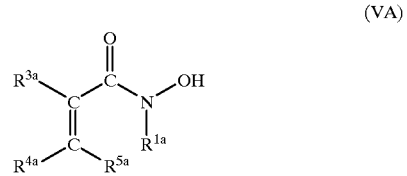

wherein $R^{1a}$ represents a hydrogen atom, a substituted or unsubstituted alkyl group having from 1 to 20 carbon atoms or a substituted or unsubstituted alkenyl group having from 2 to 20 carbon atoms;

$R^{3a}$, $R^{4a}$ and $R^{5a}$, which may be the same or different, each represents a hydrogen atom, an alkyl group having from 1 to 20 carbon atoms, an aryl group having from 6 to 22 carbon atoms, an alkoxycarbonyl group having from 2 to 30 carbon atoms, an aryloxycarbonyl group having from 7 to 30 carbon atoms or an aminocarbonyl group having from 1 to 30 carbon atoms, with the proviso that at least one of $R^{3a}$, $R^{4a}$ and $R^{5a}$ do not represent H; and when $R^{4a}$ is a phenyl group, $R^{1a}$ is a substituted or unsubstituted alkyl group having from 1 to 20 carbon atoms or a substituted or unsubstituted alkenyl group having from 2 to 20 carbon atoms.

3. The compound as claimed in claim 2, wherein $R^{1a}$ is a substituted or unsubstituted alkyl group having from 1 to 6 carbon atoms, $R^{3a}$ is a hydrogen atom, and one of $R^{4a}$ and $R^{5a}$ is an alkoxycarbonyl group having from 14 to 23 carbon atoms and the other is a hydrogen atom.

* * * * *